US012702592B2

(12) United States Patent
Gao et al.

(10) Patent No.: US 12,702,592 B2
(45) Date of Patent: Aug. 11, 2026

(54) THIN, FLEXIBLE WEARABLE IMMUNOSENSOR FOR DETECTION OF MULTIPLE BIOMARKERS/TARGETS IN BODILY FLUIDS

(71) Applicant: National University of Singapore, Singapore (SG)

(72) Inventors: Yuji Gao, Singapore (SG); Thanh Dat Nguyen, Singapore (SG); Ji Long Kenan Long, Singapore (SG); S. Y. John Ho, Singapore (SG); Chwee Teck Lim, Singapore (SG)

(73) Assignee: National University of Singapore, Singapore (SG)

( * ) Notice: Subject to any disclaimer, the term of this patent is extended or adjusted under 35 U.S.C. 154(b) by 834 days.

(21) Appl. No.: 17/928,127

(22) PCT Filed: May 5, 2021

(86) PCT No.: PCT/SG2021/050244
§ 371 (c)(1),
(2) Date: Nov. 28, 2022

(87) PCT Pub. No.: WO2021/242172
PCT Pub. Date: Dec. 2, 2021

(65) Prior Publication Data

US 2023/0210698 A1 Jul. 6, 2023

(30) Foreign Application Priority Data

May 28, 2020 (SG) ............................ 10202005000P

(51) Int. Cl.
*A61F 13/00* (2024.01)
*A61M 1/00* (2006.01)

(52) U.S. Cl.
CPC ......... *A61F 13/00051* (2013.01); *A61M 1/90* (2021.05)

(58) Field of Classification Search
CPC ........ A61J 1/2089; A61J 1/201; A61J 1/2027; B65D 1/46; B65D 51/002; B65D 81/3211
See application file for complete search history.

(56) References Cited

U.S. PATENT DOCUMENTS 8,246,592 B2 8/2012 Lockwood et al.
2007/0049888 A1* 3/2007 Soerens ................. A61F 13/53 604/372

(Continued)

FOREIGN PATENT DOCUMENTS

GB 2584899 A 12/2020
WO 2011/004165 A1 1/2011

(Continued)

OTHER PUBLICATIONS

International Preliminary Report on Patentability issued in International Application No. PCT/SG2021/050244 dated Nov. 17, 2022 (7 pages).

(Continued)

*Primary Examiner* — Andrew J Mensh
*Assistant Examiner* — Jihad Dakkak
(74) *Attorney, Agent, or Firm* — Osha Bergman Watanabe & Burton LLP

(57) ABSTRACT

A layered dressing includes: a permeable wound contact layer for placing in contact with a wound; a breathable barrier layer; a biosensor sensing array configured to detect one or more markers in wound fluid; and a fluid collection layer disposed between the wound contact layer and breathable barrier layer and configured to deliver wound fluid by capillary action from a wound in contact with the wound contact layer to the biosensor sensing array.

16 Claims, 46 Drawing Sheets a

(56) References Cited

U.S. PATENT DOCUMENTS

2008/0156646 A1* 7/2008 Wu .................... G01N 33/5438 204/450
2010/0022990 A1* 1/2010 Karpowicz ............ A61M 1/74 604/543
2013/0274629 A1* 10/2013 Duesterhoft ............ H04Q 9/00 600/573
2015/0018792 A1 1/2015 Marsiquet
2018/0267012 A1 9/2018 Scherer
2019/0137436 A1* 5/2019 Lillehoj ................ C12Q 1/006

FOREIGN PATENT DOCUMENTS

WO 2018223090 A1 12/2018
WO 2019/238181 A1 12/2019

OTHER PUBLICATIONS

International Search Report issued for corresponding international application PCT/SG2021/050244 issued Jul. 1, 2021 (5 pages).
Written Opinion issued for corresponding international patent application PCT/SG2021/050244 issued Jul. 1, 2021 (5 pages).
Yuji Gao, et al. "A flexible multiplexed immunosensor for point-of-care in situ wound monitoring;" Science Advances Research Article; 2021 (16 pages).
Philipp Comanns et al.; "Directional, passive liquid transport: the Texas horned lizard as a model for a biometric 'liquid diode';" rsif.royalsocietypublishing.org; Jun. 29, 2015 (8 pages).
F. Mannello, D. Ligi, M. Canale, J. D. Raffetto, Omics profiles in chronic venous ulcer wound fluid: innovative applications for translational medicine. Expert Review of Molecular Diagnostics 14, 737-762 (2014).
M. S. Brown, B. Ashley, A. Koh, Wearable Technology for Chronic Wound Monitoring: Current Dressings, Advancements, and Future Prospects. Frontiers in Bioengineering and Biotechnology 6, 47 (2018).
E. A. Nelson, U. Adderley, Venous leg ulcers. BMJ Clin Evid 2016, 1902 (2016).
L. P. F. Abbade, S. Lastoria, Venous ulcer: epidemiology, physiopathology, diagnosis and treatment. International Journal of Dermatology 44, 449-456 (2005).
S. L. Drinkwater, A. Smith, K. G. Burnand, What Can Wound Fluids Tell Us About the Venous Ulcer Microenvironment? The International Journal of Lower Extremity Wounds 1, 184-190 (2002).
N. J. Trengove et al., Analysis of the acute and chronic wound environments: the role of proteases and their inhibitors. Wound Repair and Regeneration 7, 442-452 (1999).
H. Derakhshandeh, S. S. Kashaf, F. Aghabaglou, I. O. Ghanavati, A. Tamayol, Smart Bandages: The Future of Wound Care. Trends in Biotechnology 36, 1259-1274 (2018).
Y. Yang, W. Gao, Wearable and flexible electronics for continuous molecular monitoring. Chemical Society Reviews 48, 1465-1491 (2019).
M. Ochoa, R. Rahimi, B. Ziaie, in Stretchable Bioelectronics for Medical Devices and Systems, J. A. Rogers, R. Ghaffari, D.-H. Kim, Eds. (Springer International Publishing, Cham, 2016), pp. 207-226.
T. Guinovart, G. Valdes-Ramirez, J. R. Windmiller, F. J. Andrade, J. Wang, Bandage- Based Wearable Potentiometric Sensor for Monitoring Wound pH. Electroanalysis 26, 1345-1353 (2014).
P. Mostafalu et al., Smart Bandage for Monitoring and Treatment of Chronic Wounds. Small 14, 1703509 (2018).
P. Mostafalu et al., Wireless Flexible Smart Bandage for Continuous Monitoring of Wound Oxygenation. IEEE Transactions on Biomedical Circuits and Systems 9, 670-677 (2015).
P. Kassal et al., Smart bandage with wireless connectivity for uric acid biosensing as an indicator of wound status. Electrochemistry Communications 56, 6-10 (2015).
S. L. Swisher et al., Impedance sensing device enables early detection of pressure ulcers in vivo. Nature Communications 6, 6575 (2015).
M. W. Lo ffler, H. Schuster, S. Bu hler, S. Beckert, Wound Fluid in Diabetic Foot Ulceration: More Than Just an Undefined Soup? The International Journal of Lower Extremity Wounds 12, 113-129 (2013).
H. J. Wallace, M. C. Stacey, Levels of Tumor Necrosis Factor-a (TNF-a ) and Soluble TNF Receptors in Chronic Venous Leg Ulcers—Correlations to Healing Status. Journal of Investigative Dermatology 110, 292-296 (1998).
N. J. Trengove, H. Bielefeldt-Ohmann, M. C. Stacey, Mitogenic activity and cytokine levels in non-healing and healing chronic leg ulcers. Wound Repair and Regeneration 8, 13-25 (2000).
L. E. Edsberg, J. T. Wyffels, M. S. Brogan, K. M. Fries, Analysis of the proteomic profile of chronic pressure ulcers. Wound Repair and Regeneration 20, 378-401 (2012).
M. S. Gohel, R. A. J. Windhaber, J. F. Tarlton, M. R. Whyman, K. R. Poskitt, The relationship between cytokine concentrations and wound healing in chronic venous ulceration. Journal of Vascular Surgery 48, 1272-1277 (2008).
G. Power, Z. Moore, T. O'Connor, Measurement of pH, exudate composition and temperature in wound healing: a systematic review. Journal of Wound Care 26, 381-397 (2017).
S. Ono et al., Increased wound pH as an indicator of local wound infection in second degree burns. Burns 41, 820-824 (2015).
S. L. Percival, S. McCarty, J. A. Hunt, E. J. Woods, The effects of pH on wound healing, biofilms, and antimicrobial efficacy. Wound Repair and Regeneration 22, 174-186 (2014).
L. A. Schneider, A. Korber, S. Grabbe, J. Dissemond, Influence of pH on wound-healing: a new perspective for wound-therapy? Archives of Dermatological Research 298, 413-420 (2007).
E. M. Jones, C. A. Cochrane, S. L. Percival, The Effect of pH on the Extracellular Matrix and Biofilms. Advances in Wound Care 4, 431-439 (2014).
R. D. Wolcott et al., Analysis of the chronic wound microbiota of 2,963 patients by 16S rDNA pyrosequencing. Wound Repair and Regeneration 24, 163-174 (2016).
J. Li et al., Designing biomimetic liquid diodes. Soft Matter 15, 1902-1915 (2019).
P. Comanns et al., Moisture harvesting and water transport through specialized microstructures on the integument of lizards. Beilstein Journal of Nanotechnology 2, 204-214 (2011).
Y. Liu, Q. Zhou, A. Revzin, An aptasensor for electrochemical detection of tumor necrosis factor in human blood. Analyst 138, 4321-4326 (2013).
V. A. Spiridonova, T. M. Novikova, O. V. Snigirev, Obtaining DNA aptamers to human interleukin-6 for biomagnetic immunoassay nanosensors. Moscow University Physics Bulletin 71, 135-138 (2016).
H. J. Sung et al., Inhibition of human neutrophil activity by an RNA aptamer bound to interleukin-8. Biomaterials 35, 578-589 (2014).
G. Liu, M. Qi, M. R. Hutchinson, G. Yang, E. M. Goldys, Recent advances in cytokine detection by immunosensing. Biosensors and Bioelectronics 79, 810-821 (2016).
S. Su et al., Dual-Target Electrochemical Biosensing Based on DNA Structural Switching on Gold Nanoparticle—Decorated MoS2 Nanosheets. ACS Applied Materials & Interfaces 8, 6826-6833 (2016).
Z. Matharu et al., Detecting Transforming Growth Factor-B Release from Liver Cells Using an Aptasensor Integrated with Microfluidics. Analytical Chemistry 86, 8865-8872 (2014).
R. Zillmer, H. Trøstrup, T. Karlsmark, P. Ifversen, M. S. Agren, Duration of wound fluid secretion from chronic venous leg ulcers is critical for interleukin-1a , interleukin-1 , interleukin-8 levels and fibroblast activation. Archives of Dermatological Research 303, 601 (2011).
P. G. Bowler, B. I. Duerden, D. G. Armstrong, Wound Microbiology and Associated Approaches to Wound Management. Clinical Microbiology Reviews 14, 244 (2001).
S. DeLeon et al., Synergistic Interactions of *Pseudomonas aeruginosa* and *Staphylococcus aureus* in an In Vitro Wound Model. Infection and Immunity 82, 4718 (2014).
S. Ranjbar, S. Shahrokhian, Design and fabrication of an electrochemical aptasensor using Au nanoparticles/carbon nanoparticles/

(56) References Cited

OTHER PUBLICATIONS cellulose nanofibers nanocomposite for rapid and sensitive detection of *Staphylococcus aureus*. Bioelectrochemistry 123, 70-76 (2018).
H. Y. Y. Nyein et al., A Wearable Electrochemical Platform for Noninvasive Simultaneous Monitoring of Ca2+ and pH. ACS Nano 10, 7216-7224 (2016).
W. Gao et al., Fully integrated wearable sensor arrays for multiplexed in situ perspiration analysis. Nature 529, 509-514 (2016).
O. S. Kwon et al., Flexible FET-Type VEGF Aptasensor Based on Nitrogen-Doped Graphene Converted from Conducting Polymer. ACS Nano 6, 1486-1493 (2012).
M. Ritsu et al., Critical role of tumor necrosis factor-a in the early process of wound healing in skin. Journal of Dermatology & Dermatologic Surgery 21, 14-19 (2017).
Y. Guo et al., In Vivo Bioluminescence Imaging to Evaluate Systemic and Topical Antibiotics against Community-Acquired Methicillin-Resistant *Staphylococcus aureus*—Infected Skin Wounds in Mice. Antimicrobial Agents and Chemotherapy 57, 855 (2013).
J. E. S. Sutcliffe et al., Abnormal connexin expression in human chronic wounds. British Journal of Dermatology 173, 1205-1215 (2015).
N. Arroyo-Curra s et al., Real-time measurement of small molecules directly in awake, ambulatory animals. Proceedings of the National Academy of Sciences 114, 645 (2017).
Z. Hao et al., Measurement of cytokine biomarkers using an aptamer-based affinity graphene nanosensor on a flexible substrate toward wearable applications. Nanoscale 10, 21681-21688 (2018).
C. Nedeva, J. Menassa, H. Puthalakath, Sepsis: Inflammation is a Necessary Evil. Frontiers in Cell and Developmental Biology 7, 108 (2019).
Q. Liu et al., Flexible Multiplexed In2O3 Nanoribbon Aptamer-Field-Effect Transistors for Biosensing. iScience 23, 101469 (2020).
H. P. Ehrlich, T. K. Hunt, Collagen Organization Critical Role in Wound Contraction. Advances in Wound Care 1, 3-9 (2012).
A. Tankersley, M. B. Frank, M. Bebak, R. Brennan, Early effects of *Staphylococcus aureus* biofilm secreted products on inflammatory responses of human epithelial keratinocytes. Journal of Inflammation 11, 17 (2014).
Z. Wang et al., A Flexible and Regenerative Aptameric Graphene-Nafion Biosensor for Cytokine Storm Biomarker Monitoring in Undiluted Biofluids toward Wearable Applications. Advanced Functional Materials 31, 2005958 (2021).
Office Action issued in Chinese Patent Application No. 202180038758.2, mailed on Jan. 26, 2026 (26 pages).
O. Parlak, A. I ncel, L. Uzun, A. P. F. Turner, A. Tiwari, Structuring Au nanoparticles on two-dimensional MoS2 nanosheets for electrochemical glucose biosensors. Biosensors and Bioelectronics 89, 545-550 (2017).
S. Verma et al., Anti-IL8/AuNPs-rGO/ITO as an Immunosensing Platform for Noninvasive Electrochemical Detection of Oral Cancer. ACS Applied Materials & Interfaces 9, 27462-27474 (2017).
L. Wu, X. Lu, X. Fu, L. Wu, H. Liu, Gold Nanoparticles dotted Reduction Graphene Oxide Nanocomposite Based Electrochemical Aptasensor for Selective, Rapid, Sensitive and Congener-Specific PCB77 Detection. Scientific Reports 7, 5191 (2017).
C. Cao, F. Zhang, E. M. Goldys, F. Gao, G. Liu, Advances in structure-switching aptasensing towards real time detection of cytokines. TrAC Trends in Analytical Chemistry 102, 379-396 (2018).
L. Farzin, M. Shamsipur, L. Samandari, S. Sheibani, Advances in the design of nanomaterial-based electrochemical affinity and enzymatic biosensors for metabolic biomarkers: A review. Microchimica Acta 185, 276 (2018).
A. Tamayol et al., Flexible pH-Sensing Hydrogel Fibers for Epidermal Applications. Advanced Healthcare Materials 5, 711-719 (2016).
W.-Y. Lai, J.-W. Wang, B.-T. Huang, E. P.-Y. Lin, P.-C. Yang, A Novel TNF-a—Targeting Aptamer for TNF-a-Mediated Acute Lung Injury and Acute Liver Failure. Theranostics 9, 1741-1751 (2019).
A. Ainla et al., Open-Source Potentiostat for Wireless Electrochemical Detection with Smartphones. Analytical Chemistry 90, 6240-6246 (2018).
Wickham H. Ggplot2: elegant graphics for data analysis. New York, NY, USA: Springer; 2009.
V. Sridhar, K. Takahata, A hydrogel-based passive wireless sensor using a flex-circuit inductive transducer. Sensors and Actuators A: Physical 155, 58-65 (2009).
M. F. Farooqui, A. Shamim, Low Cost Inkjet Printed Smart Bandage for Wireless Monitoring of Chronic Wounds. Scientific Reports 6, 28949 (2016).
J. Escandon, A. C. Vivas, R. Perez, R. Kirsner, S 939 . Davis, A prospective pilot study of ultrasound therapy effectiveness in refractory venous leg ulcers. International Wound Journal 9, 570-578 (2012).
M. Punjiya, H. Rezaei, M. A. Zeeshan, S. Sonkusale, in 2017 19th International Conference on Solid-State Sensors, Actuators and Microsystems (Transducers). (2017), pp. 1700-1702.
B. Mirani et al., An Advanced Multifunctional Hydrogel-Based Dressing for Wound Monitoring and Drug Delivery. Advanced Healthcare Materials 6, 1700718 (2017).
R. Rahimi et al., Laser-enabled fabrication of flexible and transparent pH sensor with near-field communication for in-situ monitoring of wound infection. Sensors and Actuators B: Chemical 267, 198-207 (2018).
A. H. Najafabadi et al., Biodegradable Nanofibrous Polymeric Substrates for Generating Elastic and Flexible Electronics. Advanced Materials 26, 5823-5830 (2014).
Y. Hattori et al., Multifunctional Skin-Like Electronics for Quantitative, Clinical Monitoring of Cutaneous Wound Healing. Advanced Healthcare Materials 3, 1597-1607 (2014).
Z. Li et al., Non-invasive transdermal two-dimensional mapping of cutaneous oxygenation with a rapid-drying liquid bandage. Biomed. Opt. Express 5, 3748-3764 (2014).
S. RoyChoudhury et al., Continuous Monitoring of Wound Healing Using a Wearable Enzymatic Uric Acid Biosensor. Journal of The Electrochemical Society 165, B3168- B3175 (2018).
K. Moore, E. Huddleston, M. C. Stacey, K. G. Harding, Venous leg ulcers—the search for a prognostic indicator. International Wound Journal 4, 163-172 (2007).
A. N. Moor, D. J. Vachon, L. J. Gould, Proteolytic activity in wound fluids and tissues derived from chronic venous leg ulcers. Wound Repair and Regeneration 17, 832-839 (2009).
M. Pakyari, A. Farrokhi, M. K. Maharlooei, A. Ghahary, Critical Role of Transforming Growth Factor Beta in Different Phases of Wound Healing. Advances in Wound Care 2, 215-224 (2013).
S. K. Beidler et al., Inflammatory cytokine levels in chronic venous insufficiency ulcer tissue before and after compression therapy. Journal of Vascular Surgery 49, 1013-1020 (2009).
D. L. Gillespie, Venous ulcer diagnosis, treatment, and prevention of recurrences. Journal of Vascular Surgery 52, 8S-14S (2010).
A. R. Parker, C. R. Lawrence, Water capture by a desert beetle. Nature 414, 33-34 (2001).
M. Prakash, D. Que re , J. W. M. Bush, Surface Tension Transport of Prey by Feeding Shorebirds: The Capillary Ratchet. Science 320, 931 (2008).
Y. Zheng et al., Directional water collection on wetted spider silk. Nature 463, 640-643 (2010).
J. Ju et al., A multi-structural and multi-functional integrated fog collection system in cactus. Nature Communications 3, 1247 (2012).
H. Chen et al., Continuous directional water transport on the peristome surface of Nepenthes alata. Nature 532, 85-89 (2016).
S. Liu, J. Zhang, W. Tu, J. Bao, Z. Dai, Using ruthenium polypyridyl functionalized ZnO mesocrystals and gold nanoparticle dotted graphene composite for biological recognition and electrochemiluminescence biosensing. Nanoscale 6, 2419-2425 (2014).
J. Song et al., Synthesis of Au/Graphene Oxide Composites for Selective and Sensitive Electrochemical Detection of Ascorbic Acid. Scientific Reports 4, 7515 (2014).
A. K. Yagati, M.-H. Lee, J. Min, Electrochemical immunosensor for highly sensitive and quantitative detection of tumor necrosis factor—in human serum. Bioelectrochemistry 122, 93-102 (2018).

(56) References Cited

OTHER PUBLICATIONS

Y. Xiao, A. A. Lubin, A. J. Heeger, K. W. Plaxco, Label-Free Electronic Detection of Thrombin in Blood Serum by Using an Aptamer-Based Sensor. Angewandte Chemie International Edition 44, 5456-5459 (2005).
A. J. Singer, R. A. F. Clark, Cutaneous Wound Healing. New England Journal of Medicine 341, 738-746 (1999).
D. L. Coleman, R. N. King, J. D. Andrade, The foreign body reaction: A chronic inflammatory response. Journal of Biomedical Materials Research 8, 199-211 (1974).
I. A. Darby, T. D. Hewitson, Fibroblast Differentiation in Wound Healing and Fibrosis, International Review of Cytology. (Academic Press, 2007), vol. 257, pp. 143-179.
Rahimi, R. et al. A low-cost flexible pH sensor array for wound assessment. Sensors and Actuators B: Chemical 229, 609-617 (2016).
Nakagami, G. et al. Predicting delayed pressure ulcer healing using thermography: a prospective cohort study. Journal of Wound Care 19, 465-472 (2010).
Anastasova Salzitsa et al: A Wearable Multisensing Patch for Continuous Sweat Monitoring, Biosensors and Bioelectronics, vol. 93, Jul. 1, 2017, pp. 139-145.
Jungil Choi et al: Thin, Soft, Skin-Mounted Microfluidic Networks with Capillary Bursting Valves for Chrono-Sampling of Sweat, Advanced Healthcare Materials, Wiley—V C H Verlag Gmbh & Co. KGAA, DE, vol. 6, No. 5, Jan. 20, 2017.
Extended European Search Report of Related EP Application No. 21813252.0 dated Jun. 10, 2024.
Hadley Wickham, Romain Franc ois, Lionel Henry and Kirill Mu ller (2019). dplyr: A Grammar of Data Manipulation. R package version 0.8.3. https://CRAN.Rproject.org/package=dplyr.
Barret Schloerke, Jason Crowley, Di Cook, Francois Briatte, Moritz Marbach, Edwin Thoen, Amos Elberg and Joseph Larmarange (2018). GGally: Extension to 'ggplot2'. R package version 1.4.0. https://CRAN.R-project.org/package=GGally.
Ricardo Bion (2020). ggradar: Create radar charts using ggplot2. R package version 0.2.
Hadley Wickham and Dana Seidel (2019). scales: Scale Functions for Visualization. R package version 1.1.0. https://CRAN.R-project.org/package=scales.

* cited by examiner

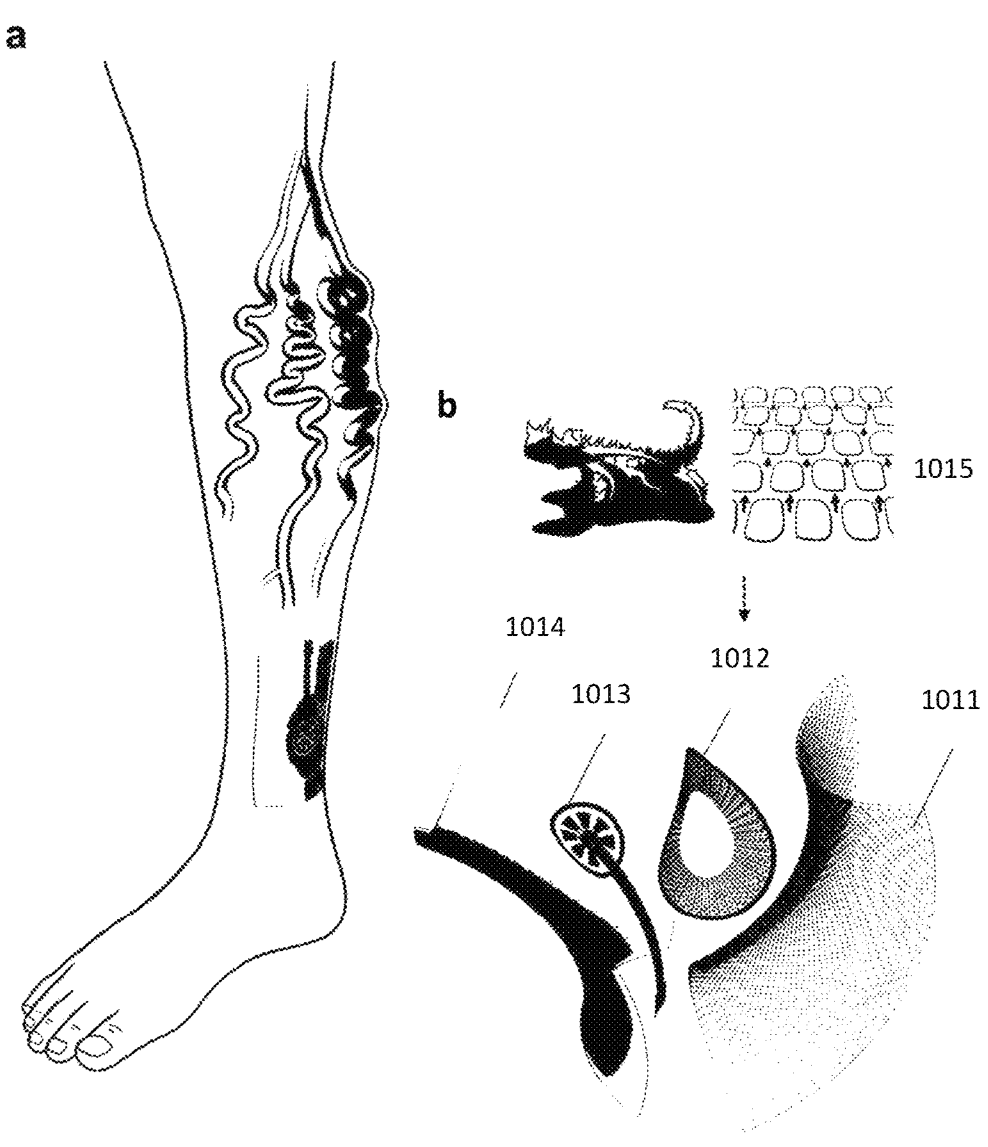
Figure 1A-B

C

D a

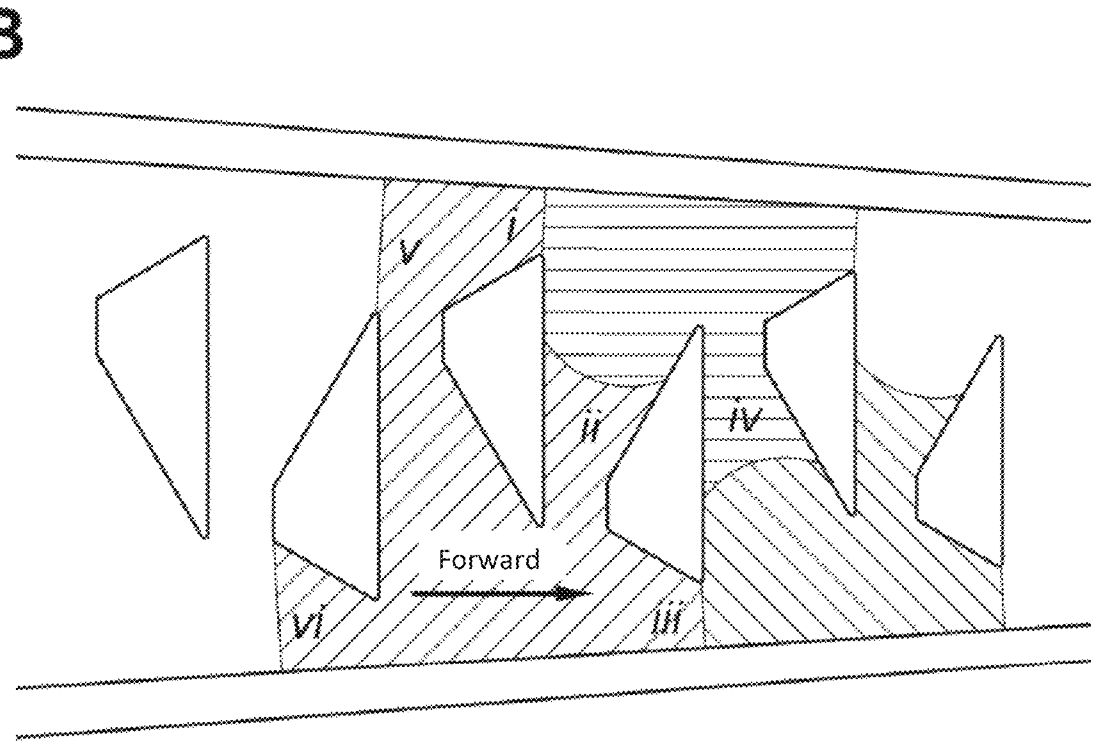
Figure 2B
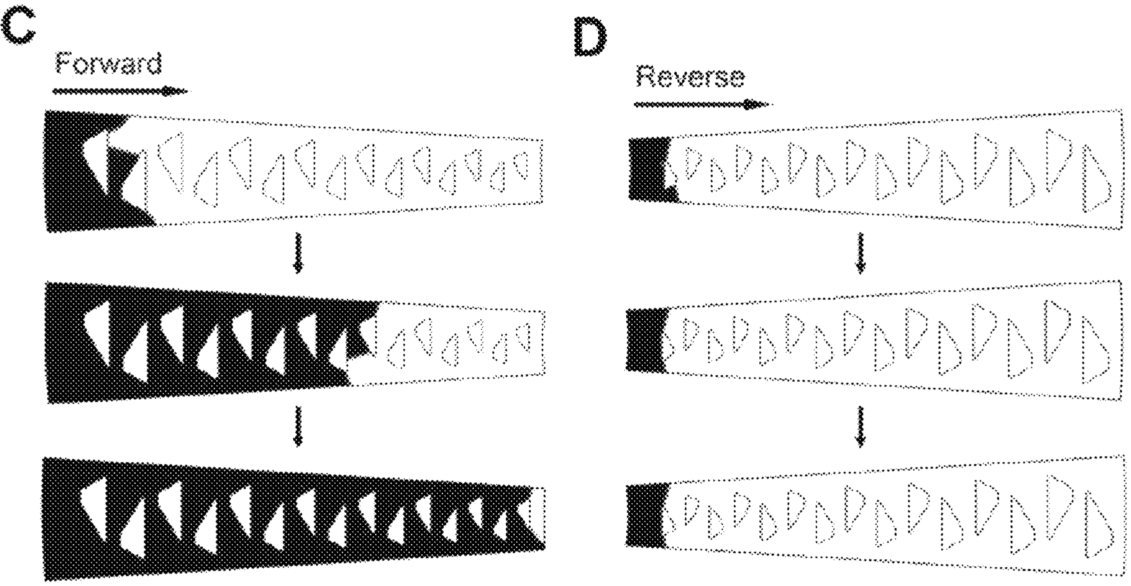
Figure 2C-D

E a b

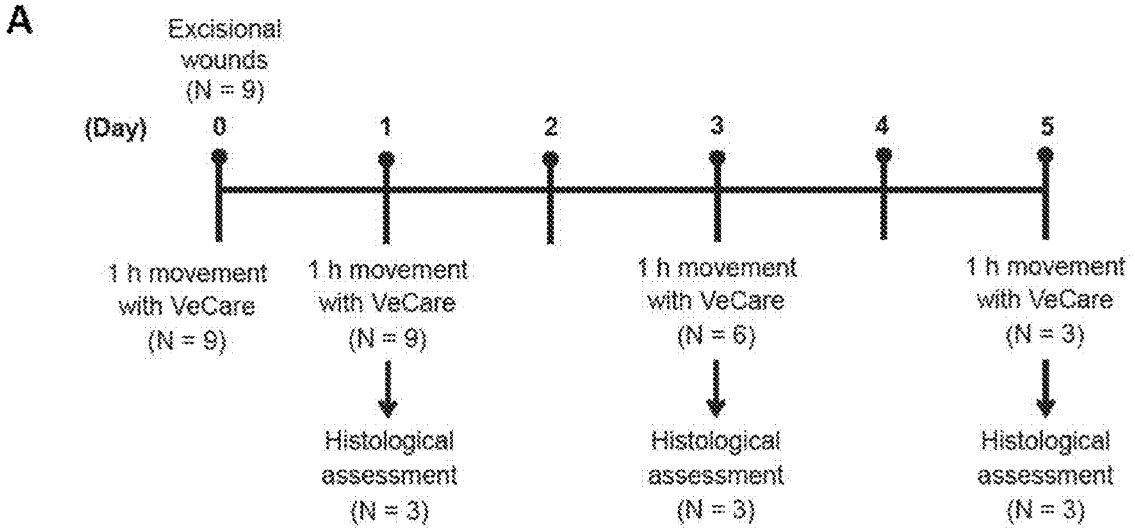
Figure 4A
b
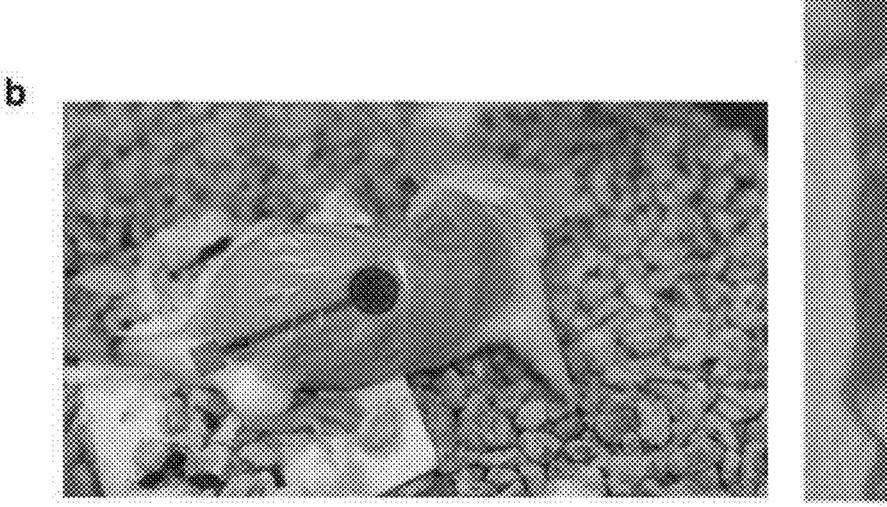
c
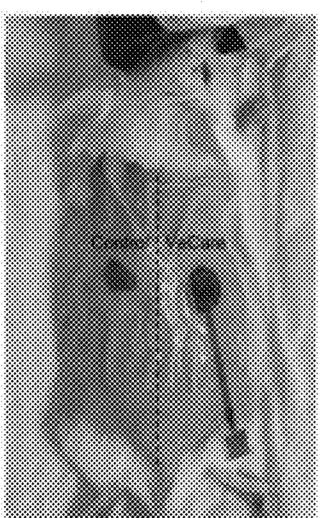
Figure 4B-C

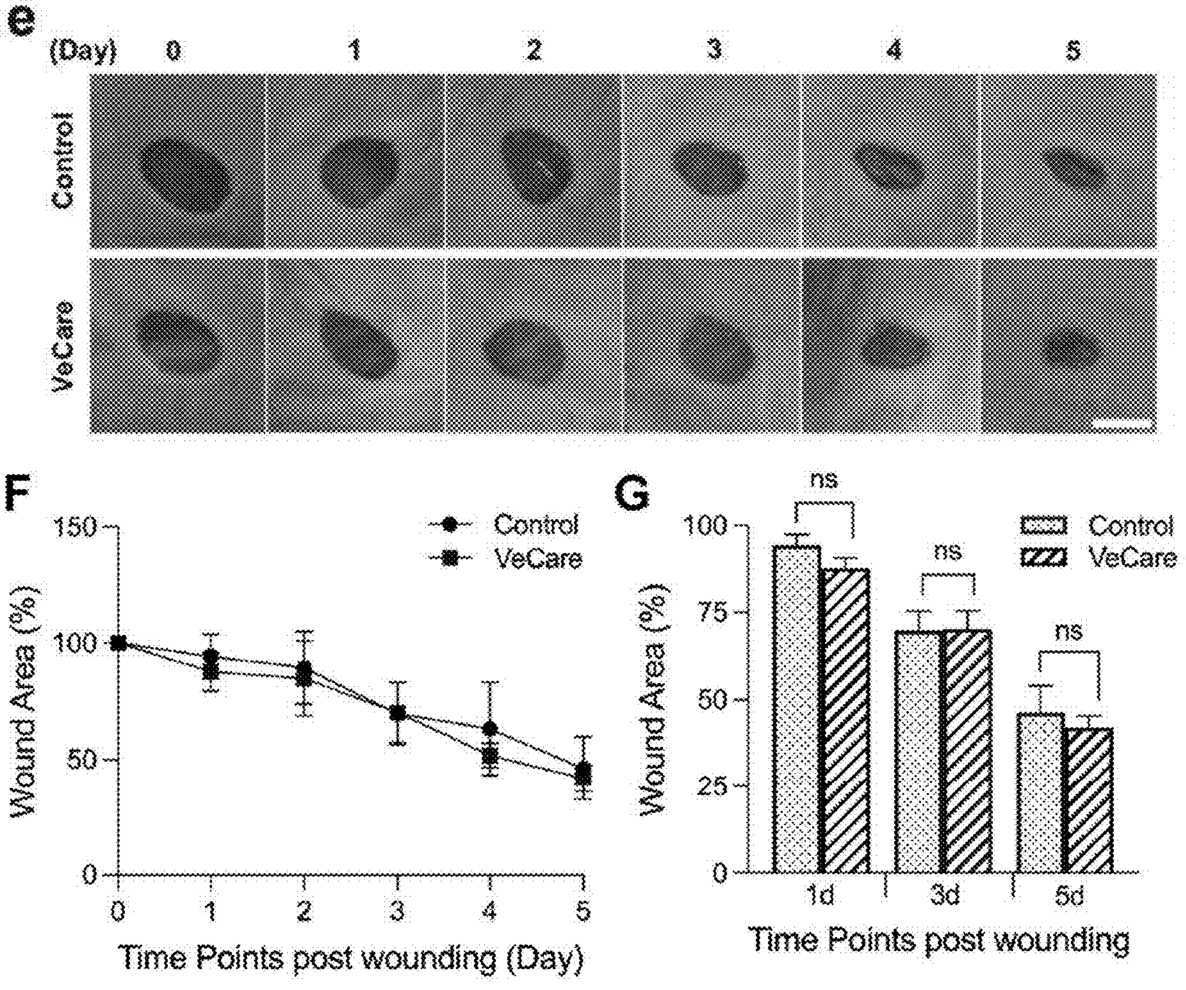
Figure 4E-G

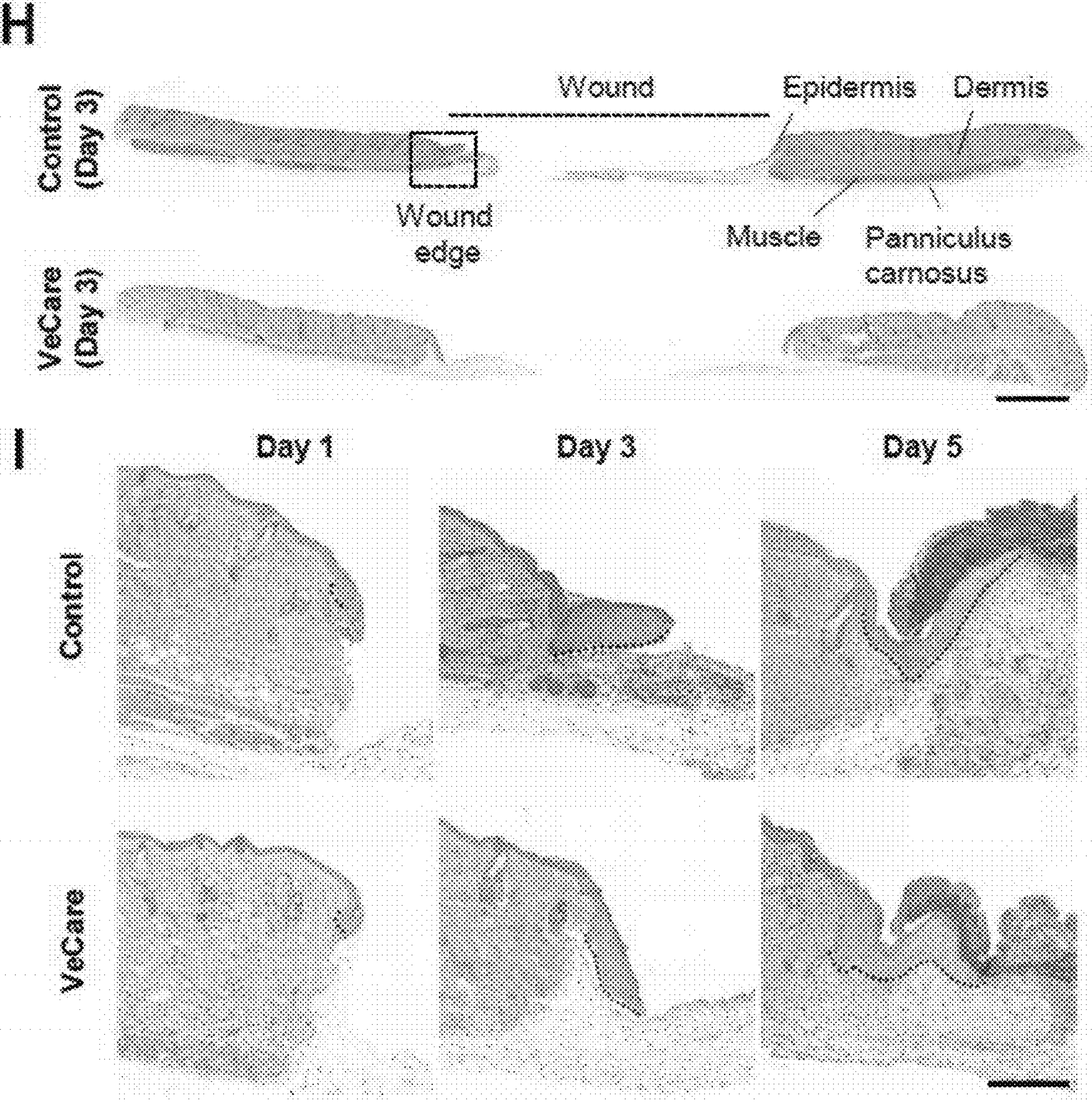
Figure 4H-I

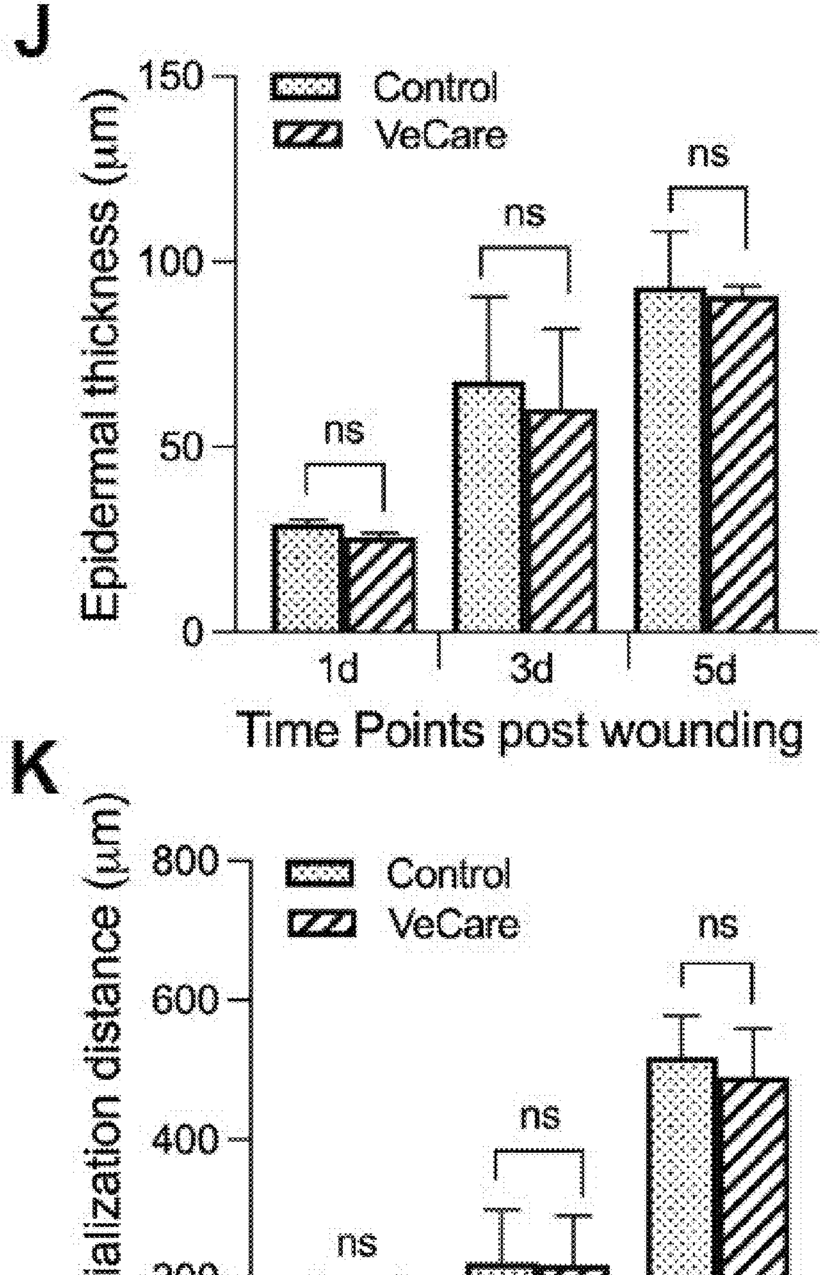
Figure 4J-K

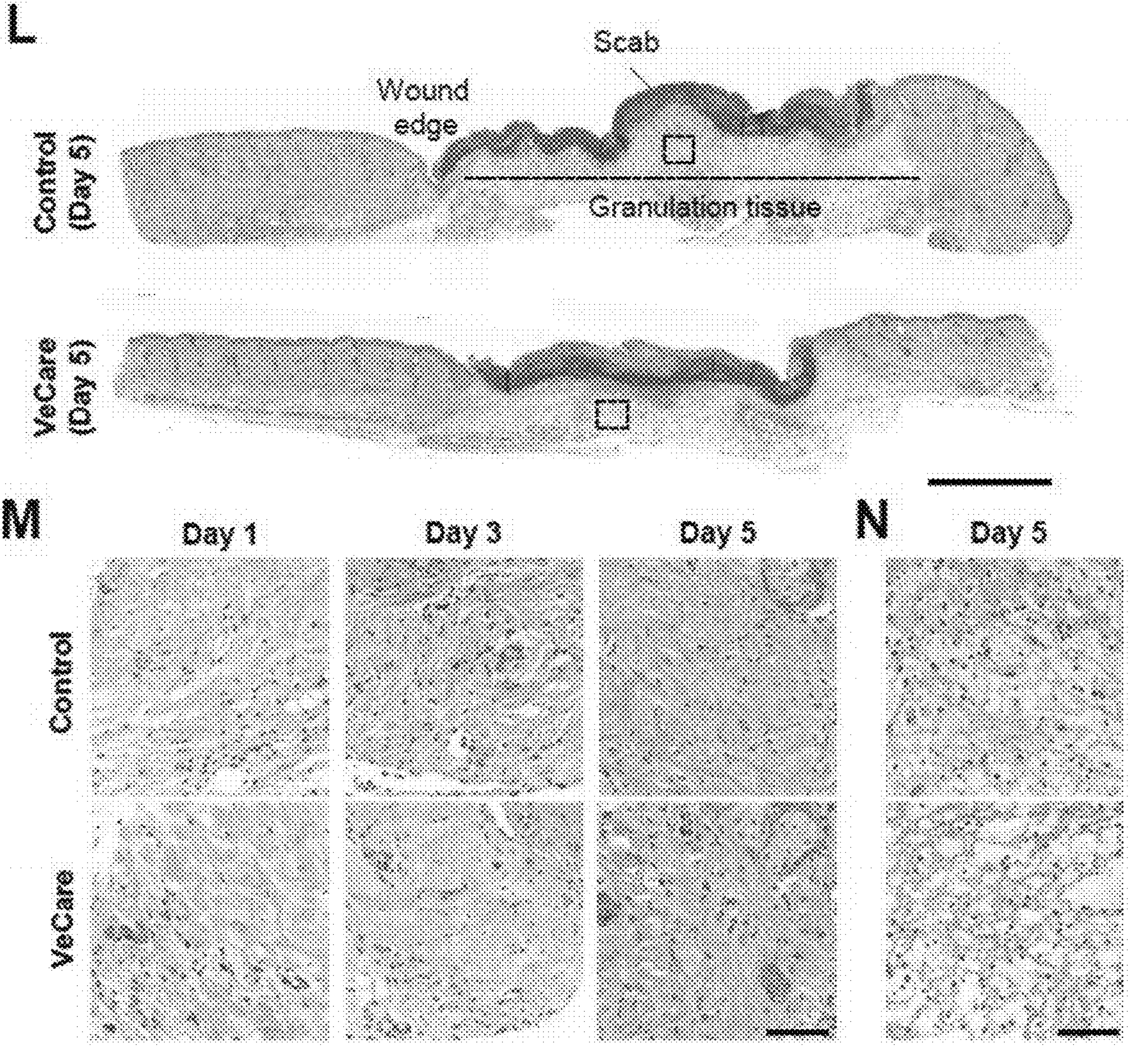
Figure 4L-N

B

① Left leg

| No. of wounds | 3 |
| --- | --- |
| Duration of wounds (month) | 12 |

| | pH | TNF-α | TGF-β1 | IL-8 | IL-6 | *S. aureus* |
| --- | --- | --- | --- | --- | --- | --- |
| IL-6 | | | | | | 0.9 |
| IL-8 | | | | | 1 | 0.9 |
| TGF-β1 | | | | 1 | 0.9 | 0.7 |
| TNF-α | | | -0.4 | -0.3 | -0.3 | -0.1 |
| pH | | -0.2 | 0.2 | 0.3 | 0.4 | 0.6 |
| Wound Size | 0.3 | -0.5 | 0.9 | 1 | 0.9 | 0.8 |

② Right leg

| No. of wounds | 1 |
| --- | --- |
| Duration of wounds (month) | 12 |

| | pH | TNF-α | TGF-β1 | IL-8 | IL-6 | *S. aureus* |
| --- | --- | --- | --- | --- | --- | --- |
| IL-6 | | | | | | 0.8 |
| IL-8 | | | | | 0.9 | 1 |
| TGF-β1 | | | | -0.2 | -0.5 | 0 |
| TNF-α | | | -1 | 0.2 | 0.5 | 0 |
| pH | | 0.1 | -0.1 | -0.9 | -0.8 | -1 |
| Wound Size | 0.7 | 0.3 | -0.4 | -0.3 | -0.3 | -0.4 |

③ Left leg

| No. of wounds | 9 |
| --- | --- |
| Duration of wounds (month) | 3 |

| | pH | TNF-α | TGF-β1 | IL-8 | IL-6 | *S. aureus* |
| --- | --- | --- | --- | --- | --- | --- |
| IL-6 | | | | | | 0.2 |
| IL-8 | | | | | 1 | 0.1 |
| TGF-β1 | | | | 1 | 1 | 0 |
| TNF-α | | | 0.8 | 0.9 | 0.9 | 0.4 |
| pH | | -0.5 | 0.1 | -0.1 | -0.1 | -0.8 |
| Wound Size | 0.6 | -0.8 | -0.6 | -0.7 | -0.8 | -0.7 |

④ Left leg

| No. of wounds | 2 |
| --- | --- |
| Duration of wounds (month) | 36 |

| | pH | TNF-α | TGF-β1 | IL-8 | IL-6 | *S. aureus* |
| --- | --- | --- | --- | --- | --- | --- |
| IL-6 | | | | | | 0.3 |
| IL-8 | | | | | 0.4 | 1 |
| TGF-β1 | | | | 1 | 0.4 | 1 |
| TNF-α | | | 1 | 1 | 0.5 | 1 |
| pH | | -0.8 | -0.6 | -0.7 | -0.3 | -0.7 |
| Wound Size | 0 | 0.5 | 0.5 | 0.5 | 0.5 | 0.5 |

⑤ Right leg

| No. of wounds | 3 |
| --- | --- |
| Duration of wounds (month) | 8 |

| | pH | TNF-α | TGF-β1 | IL-8 | IL-6 | *S. aureus* |
| --- | --- | --- | --- | --- | --- | --- |
| IL-6 | | | | | | 0.9 |
| IL-8 | | | | | 1 | 0.9 |
| TGF-β1 | | | | 0.9 | 0.9 | 1 |
| TNF-α | | | 0.7 | 0.6 | 0.5 | 0.5 |
| pH | | -0.6 | -0.8 | -0.7 | -0.8 | -0.8 |
| Wound Size | -0.3 | 0.4 | -0.2 | -0.2 | -0.2 | -0.3 |

Figure 5B

A
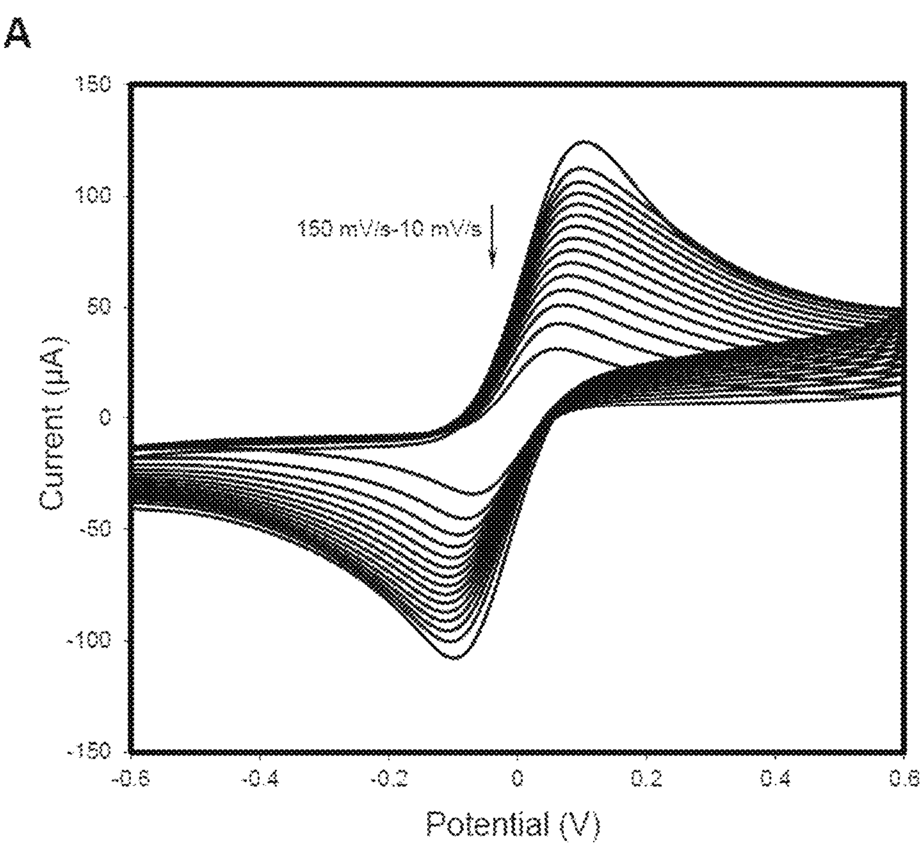
B
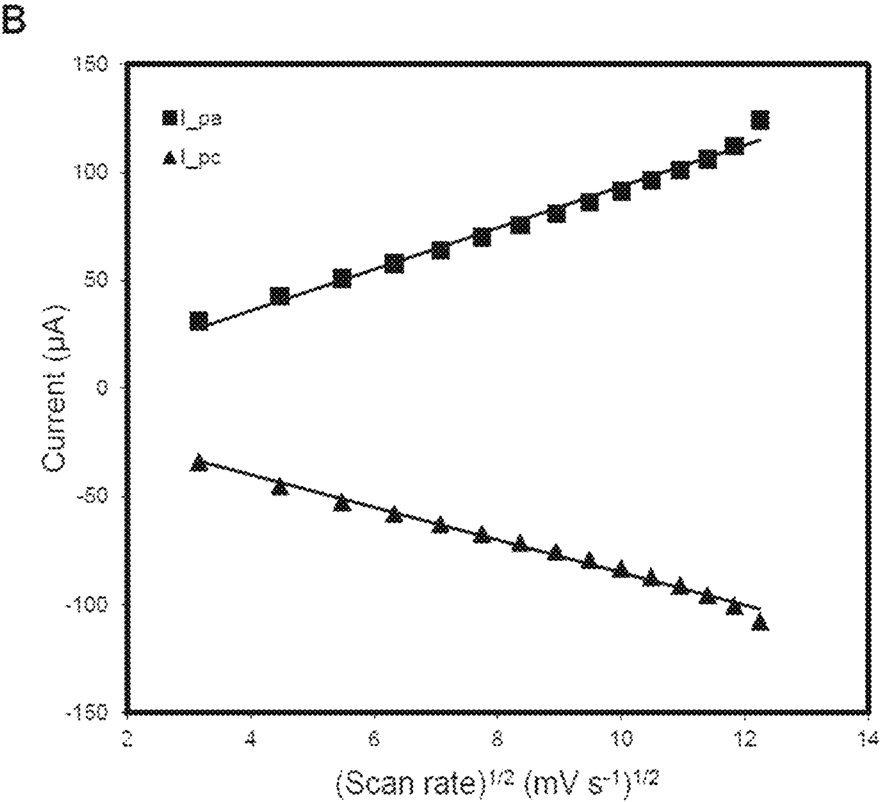
Figure 8A-B

C
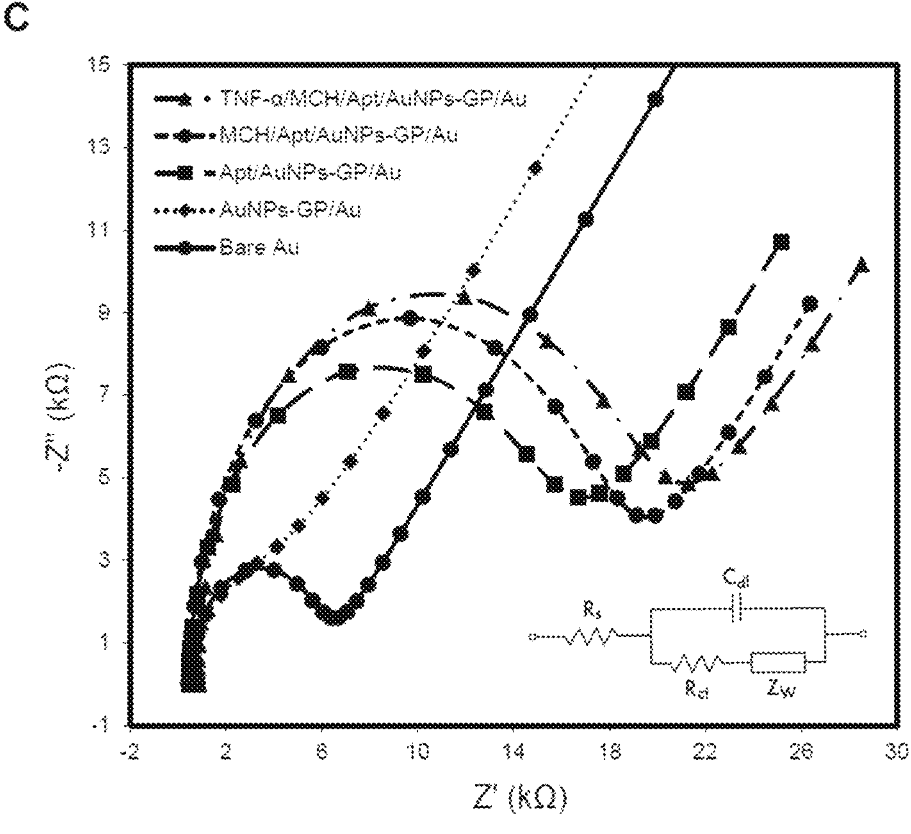
D
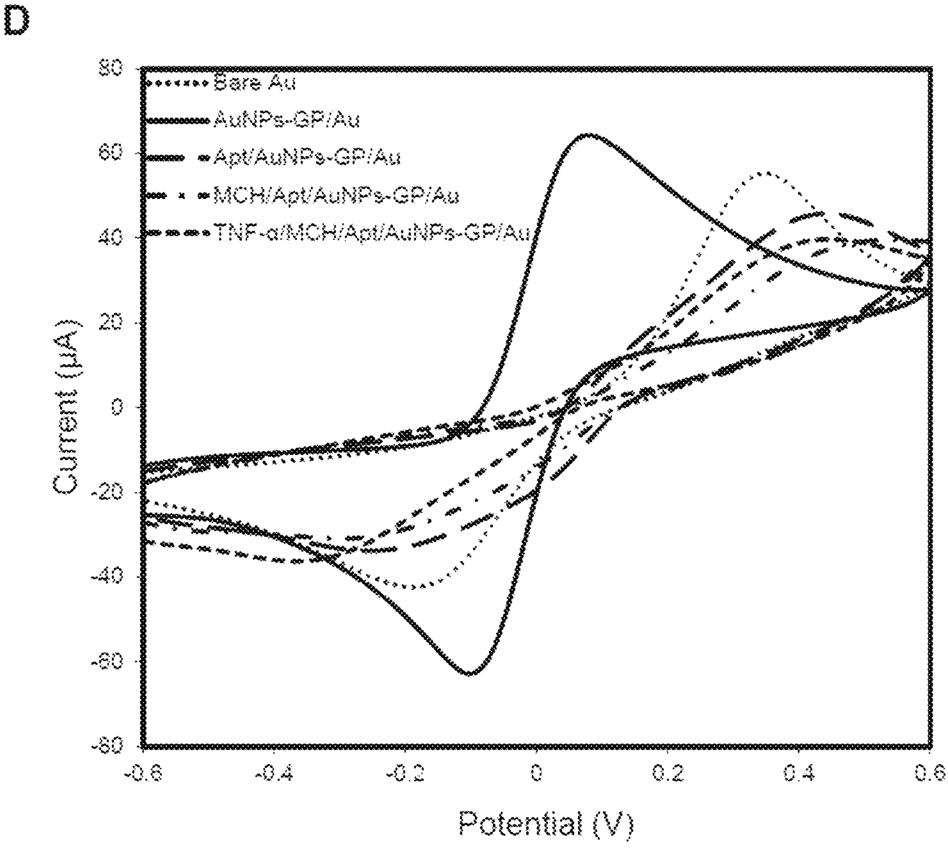
Figure 8C-D

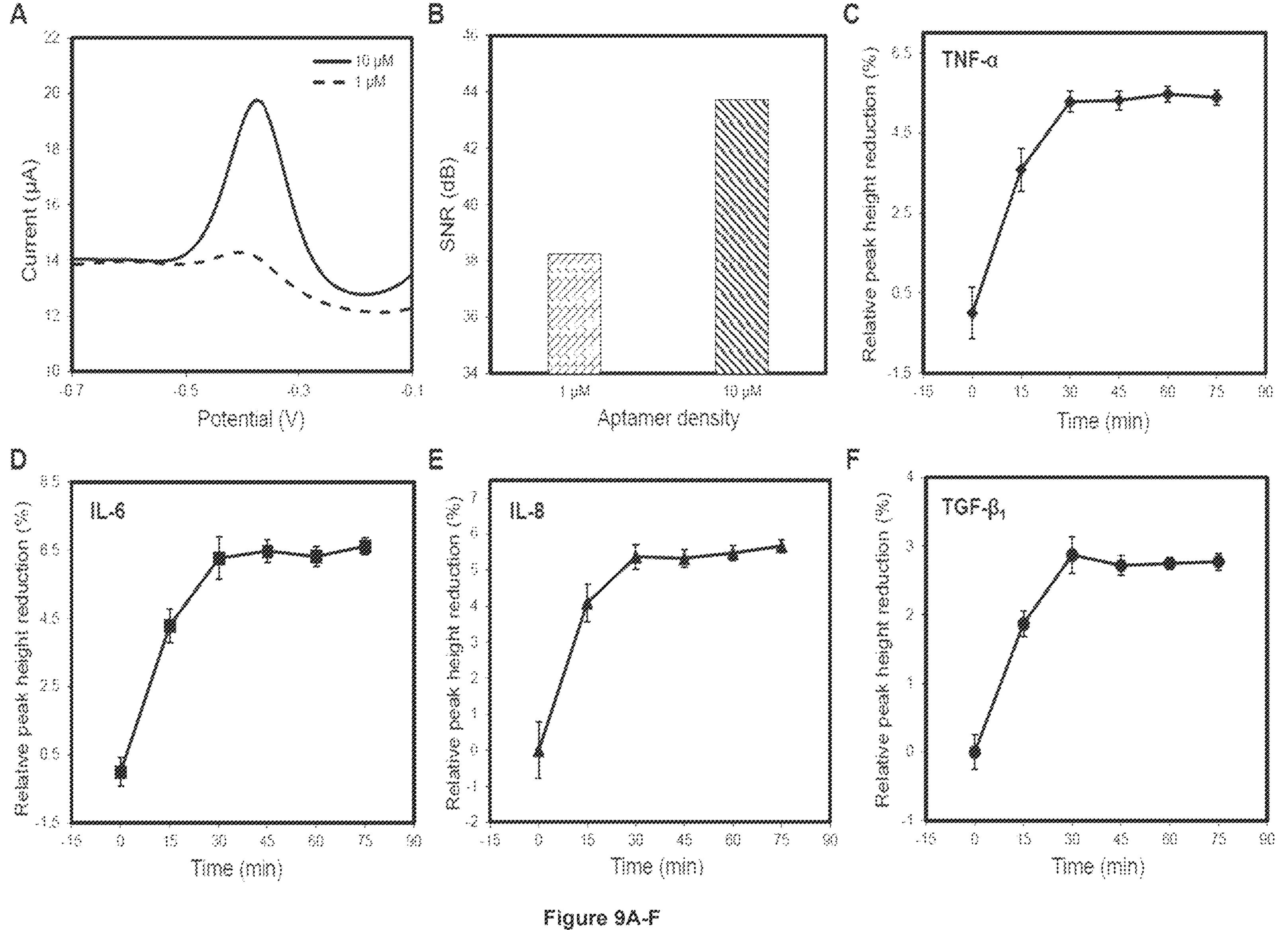
Figure 9A-F

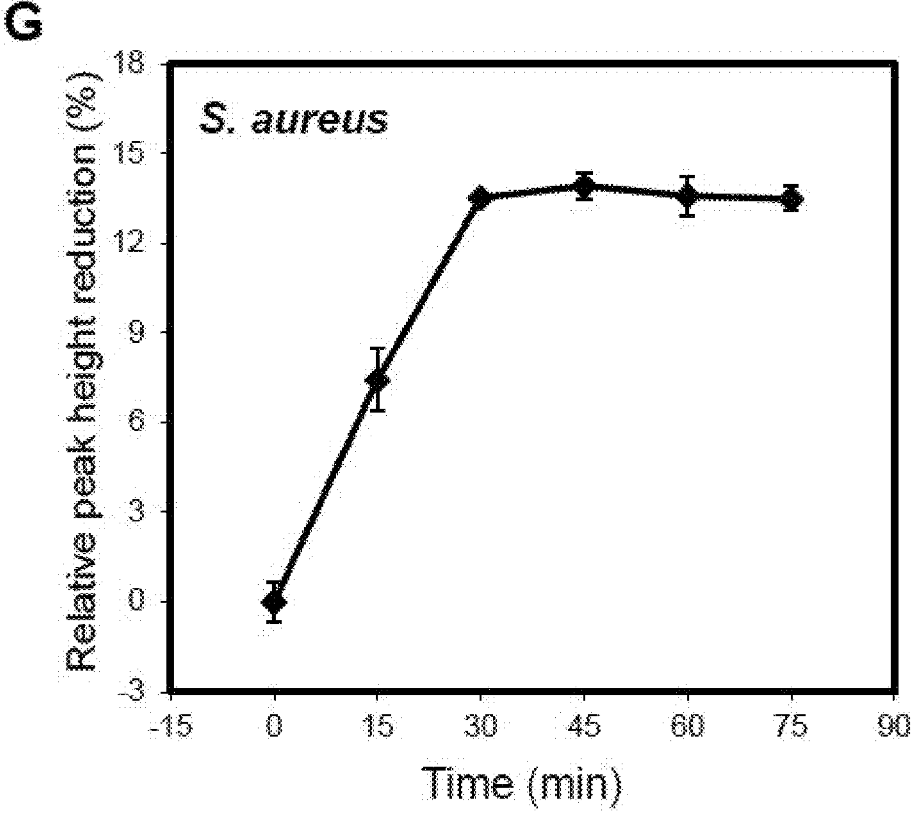
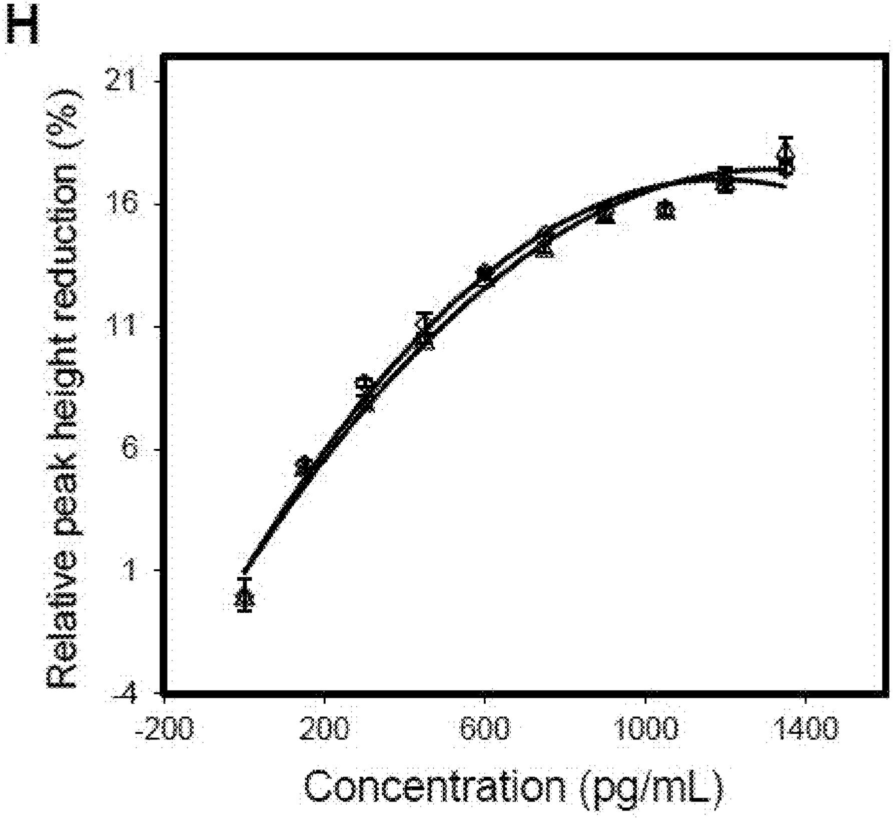
Figure 9G-H

A
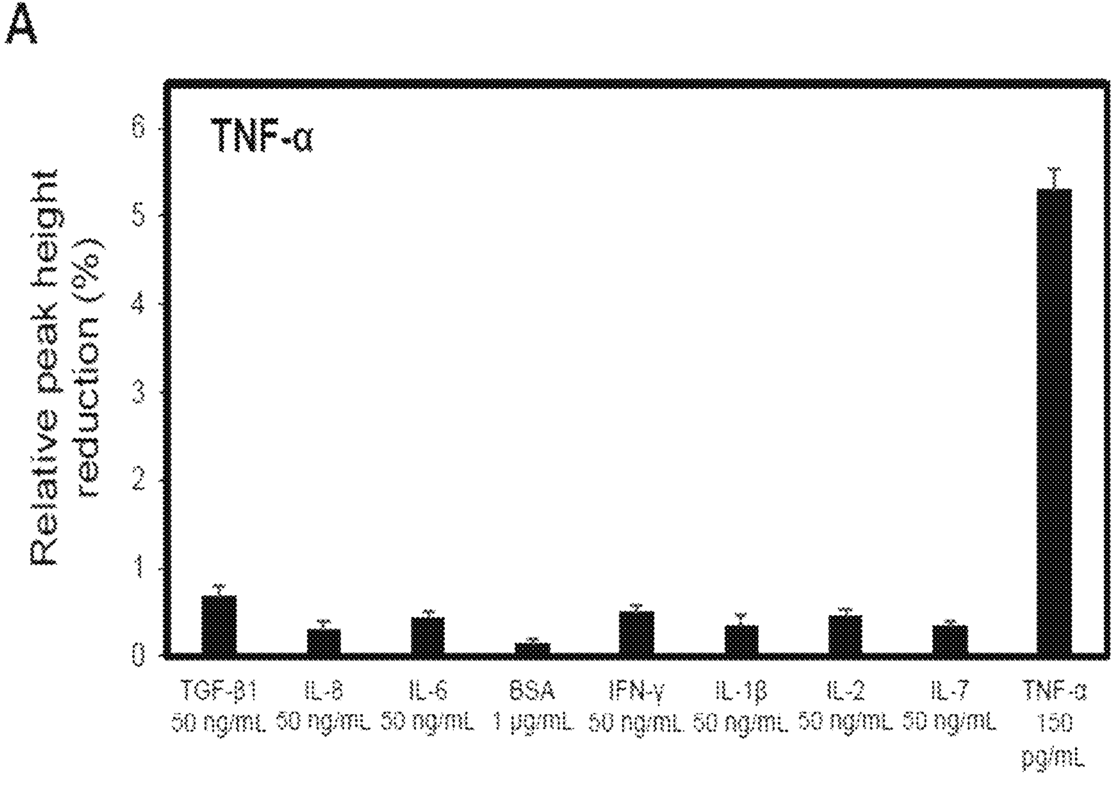
B
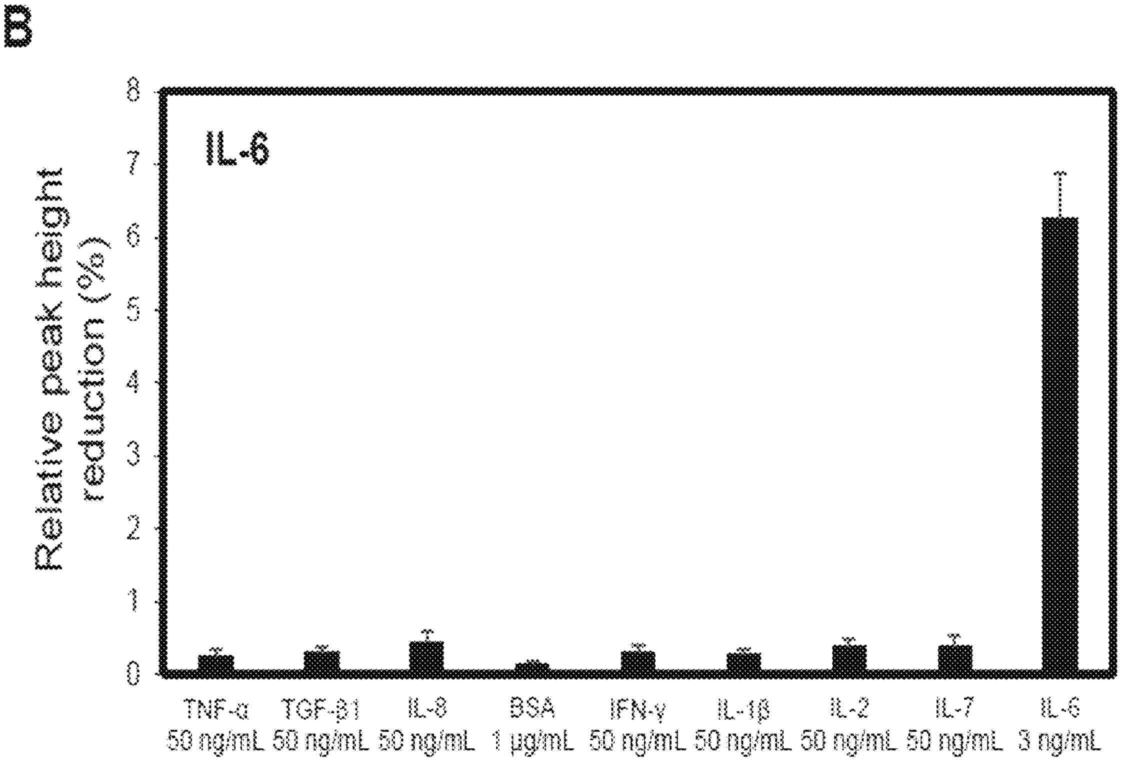
Figure 10A-B

C
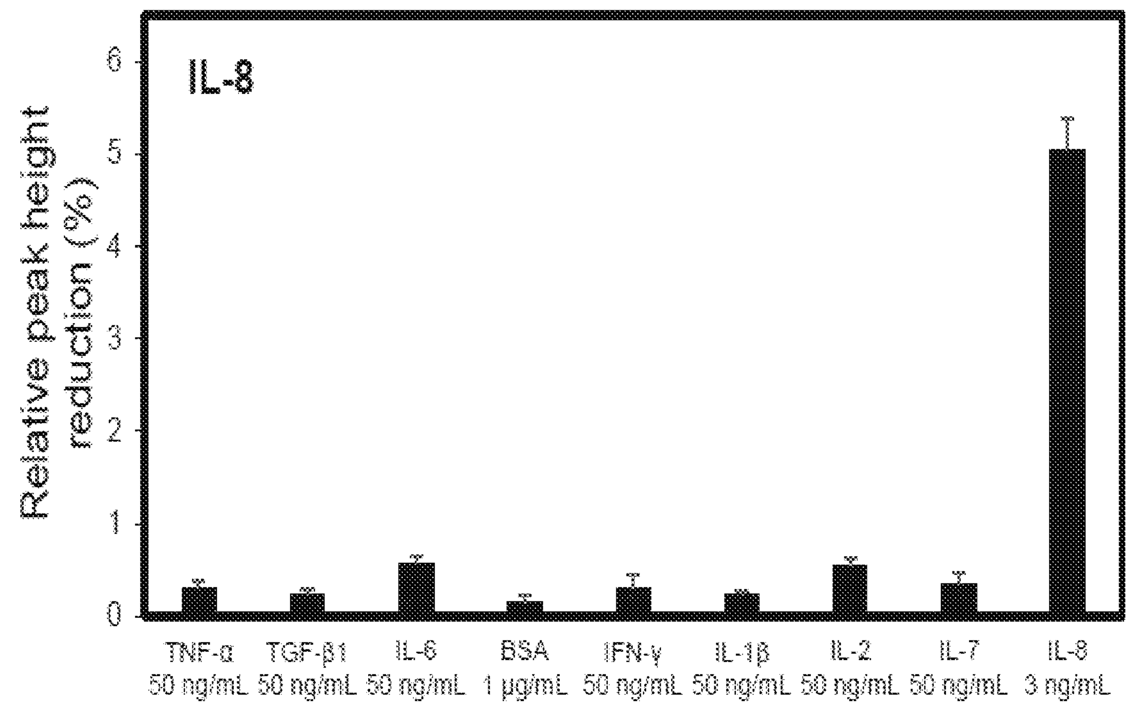
D
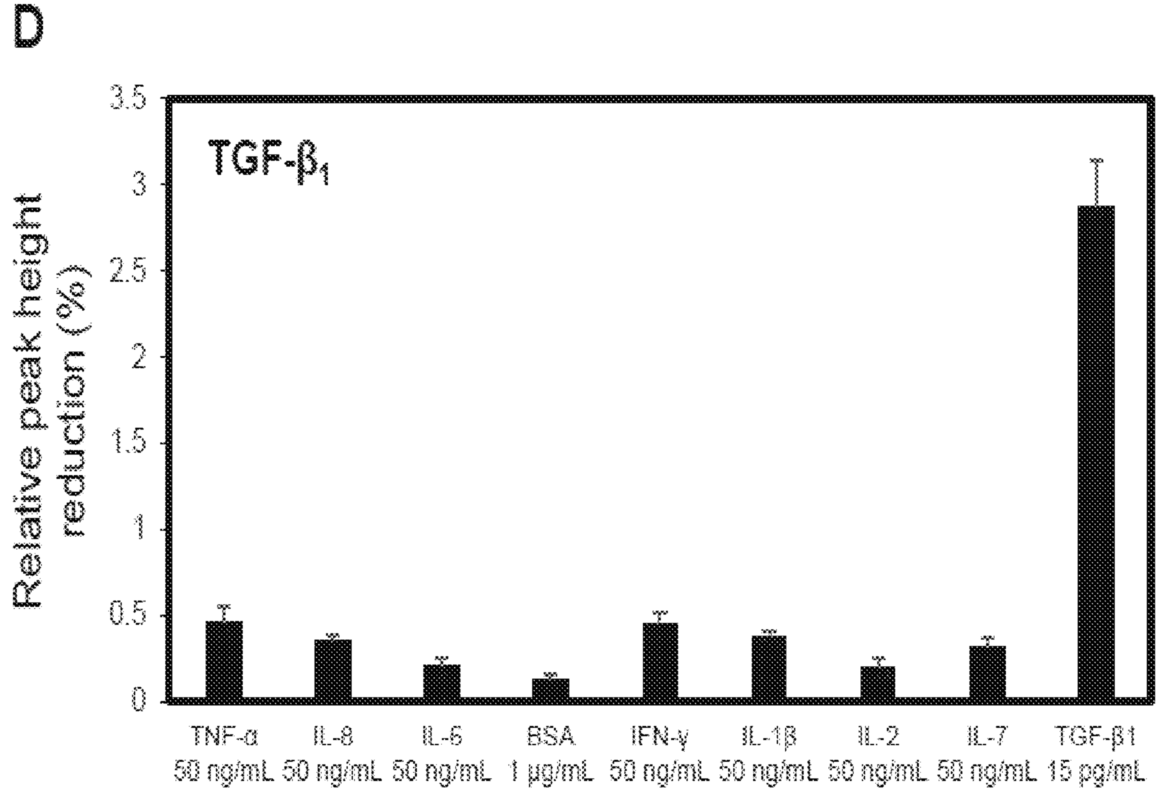
Figure 10C-D

A
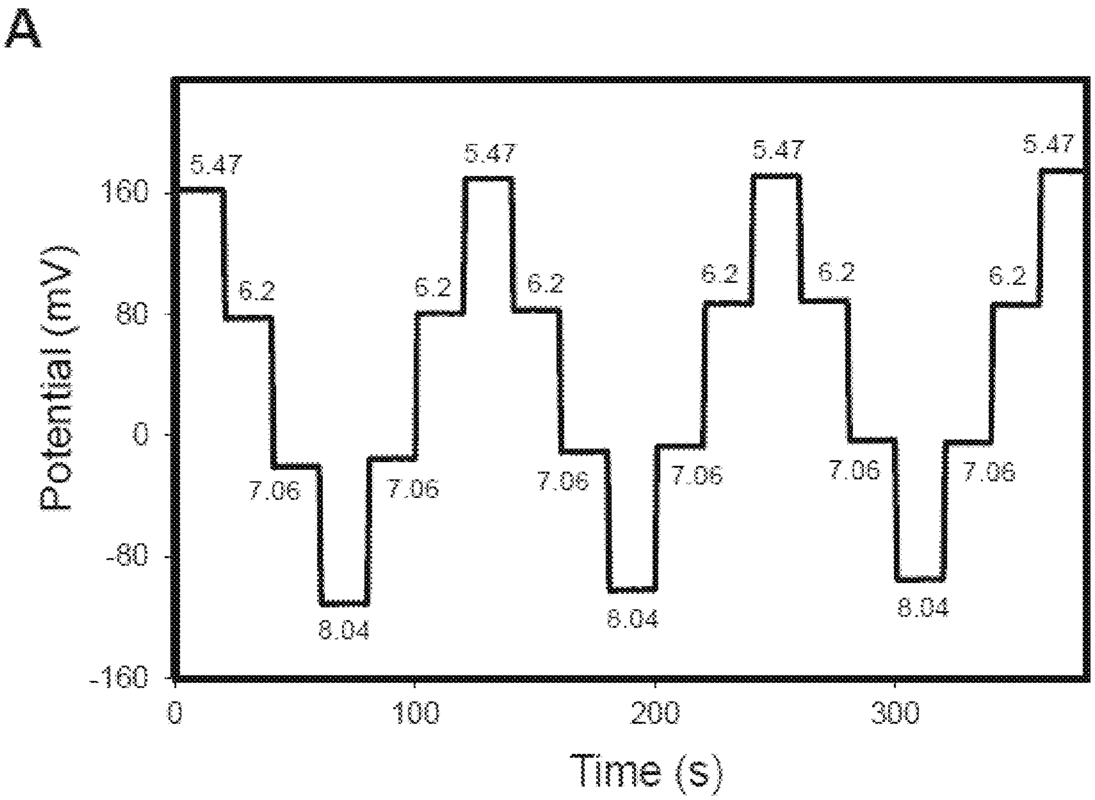
B
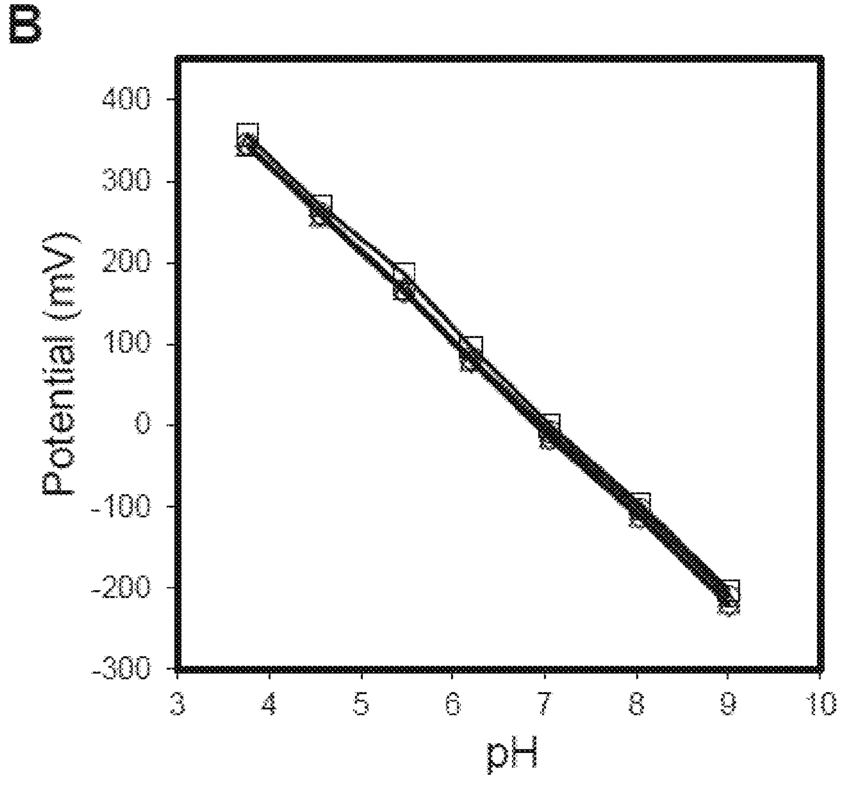
Figure 11A-B

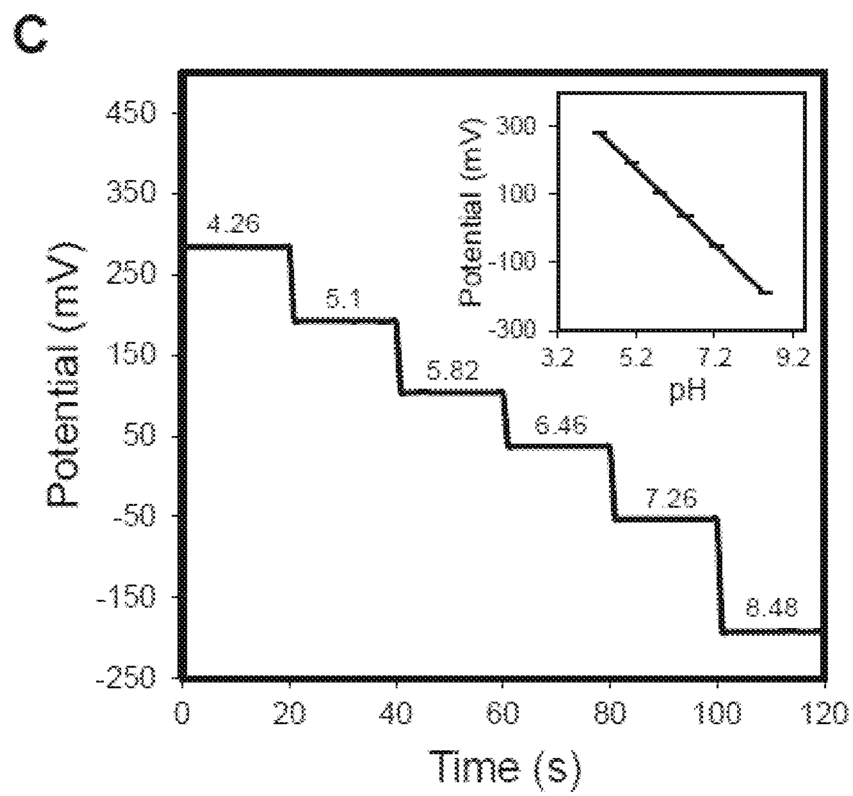
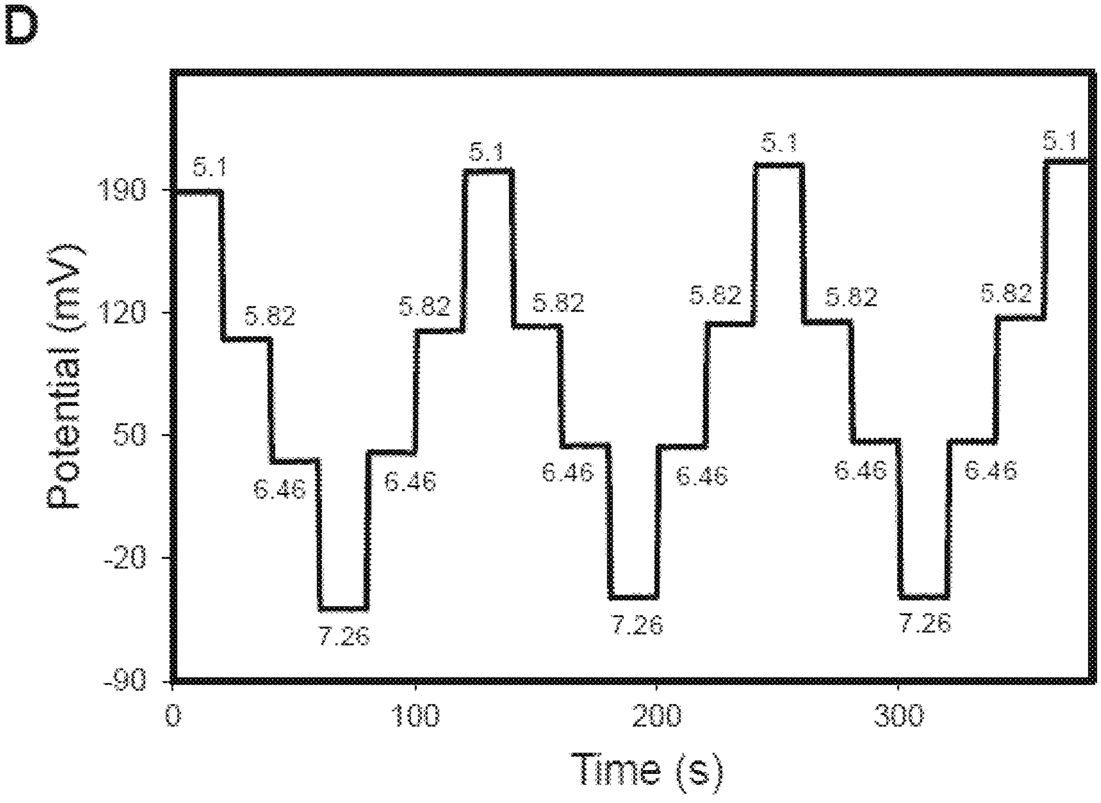
Figure 11C-D

E
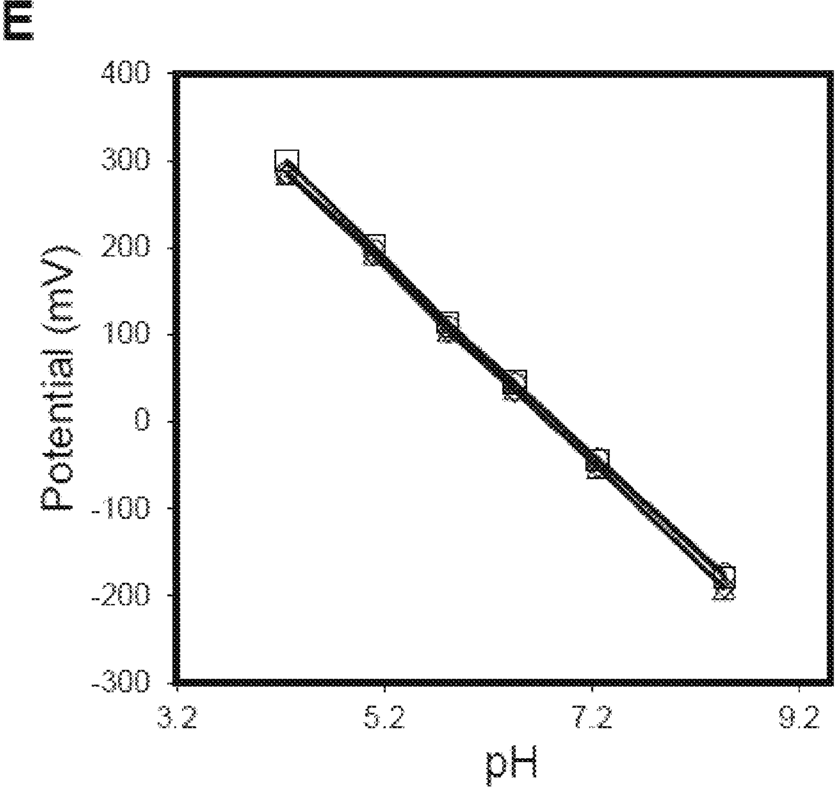
F
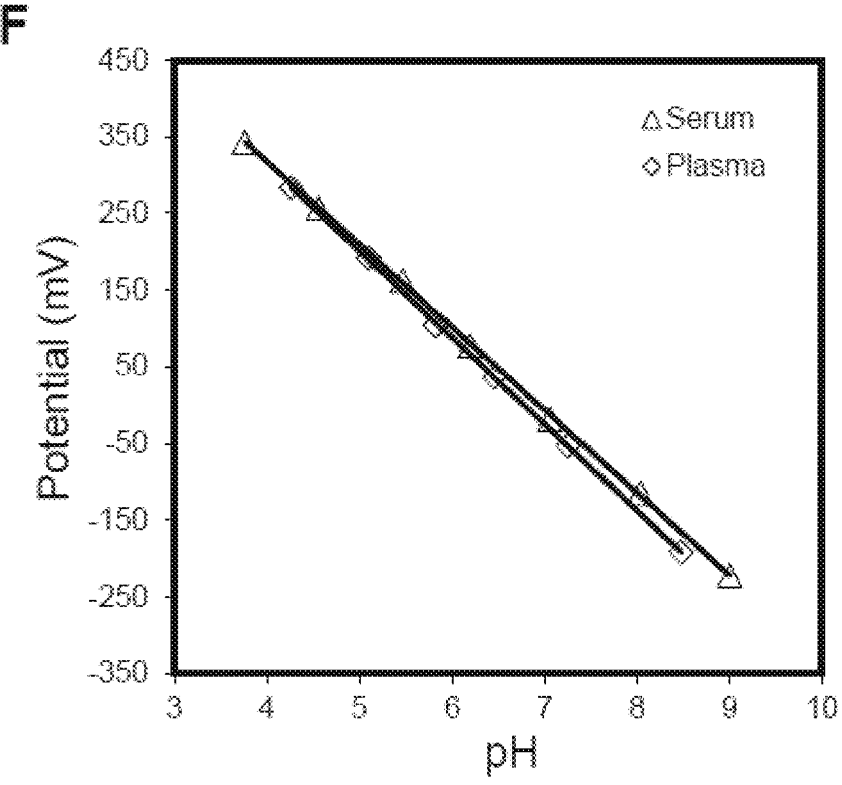
Figure 11E-F a
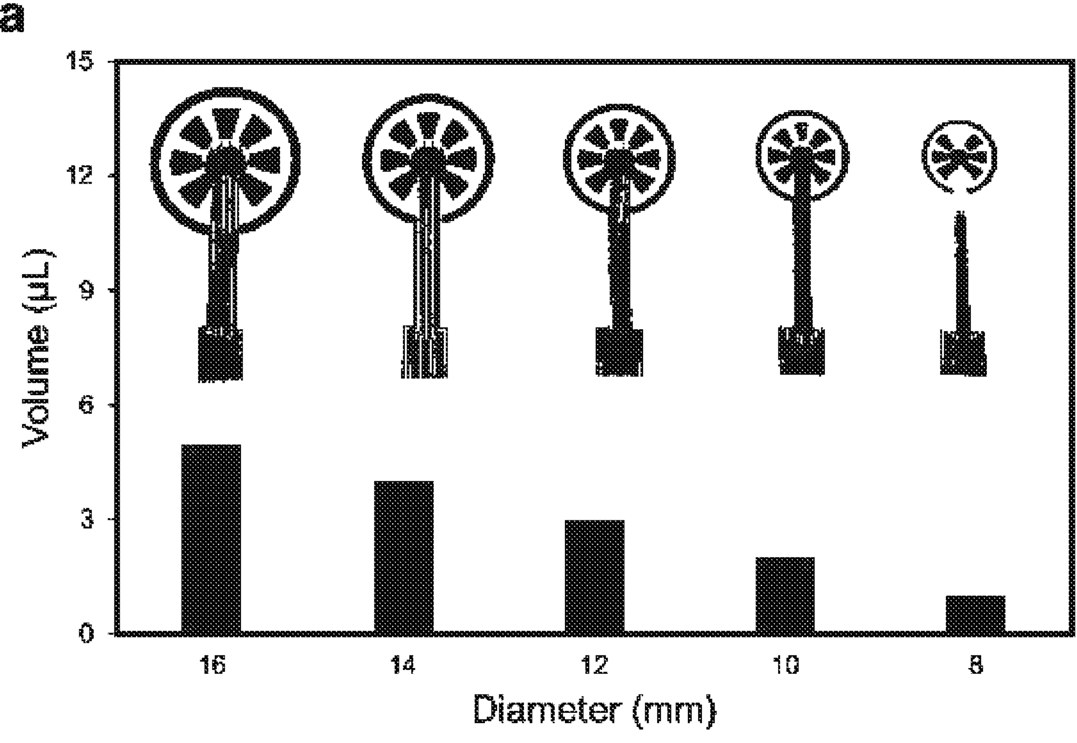
b
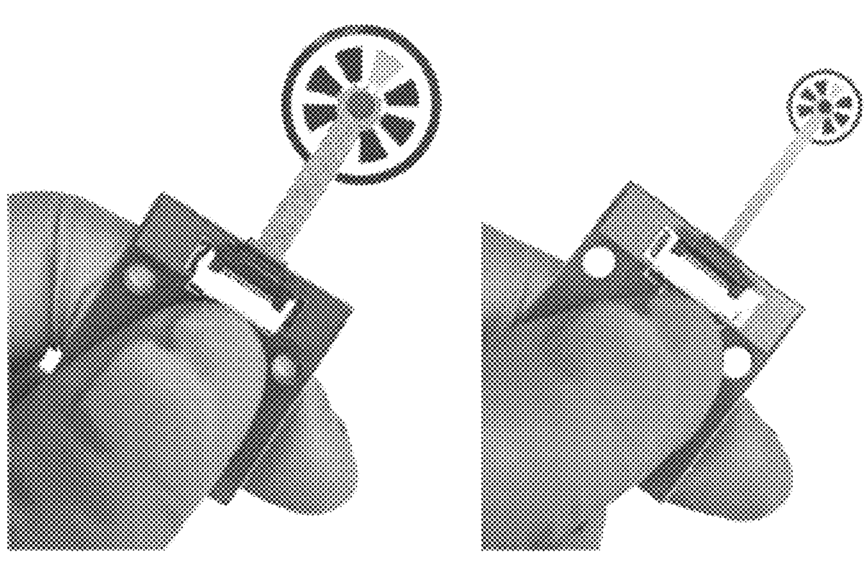
Figure 12A-B

A
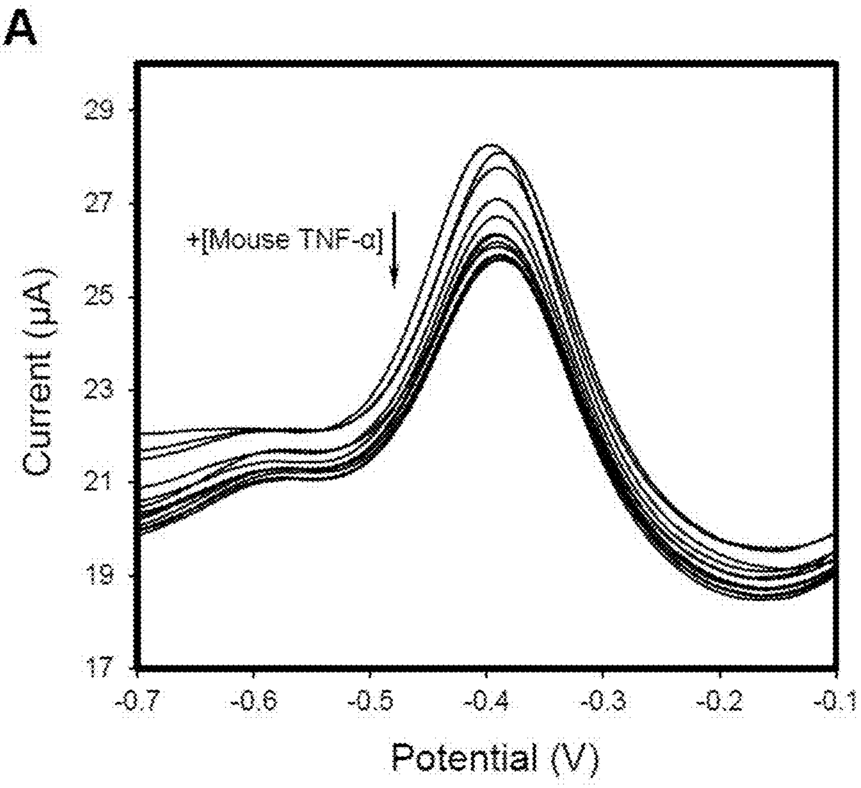
B
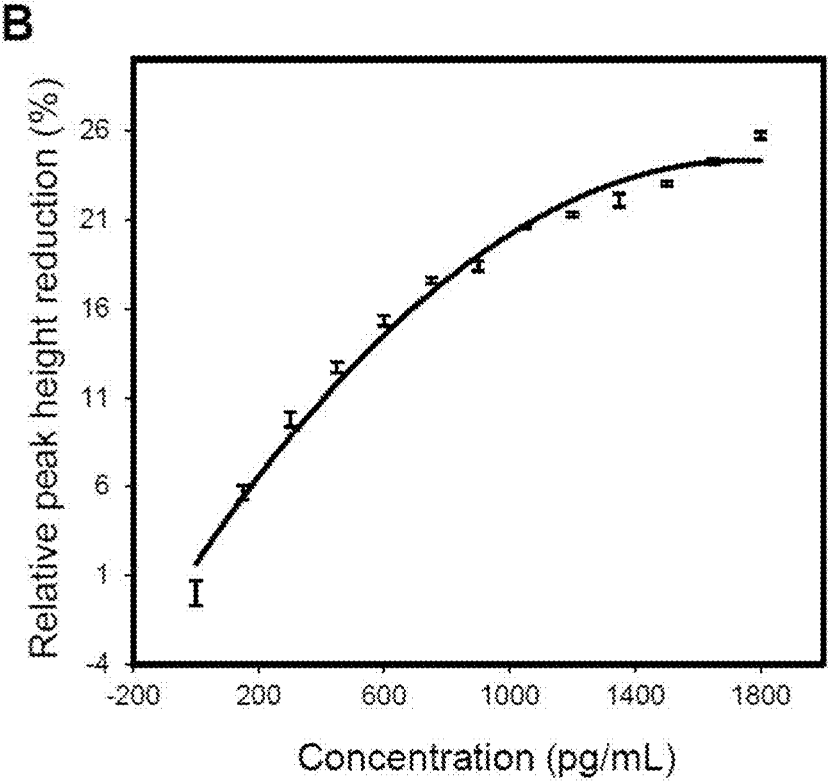
Figure 14

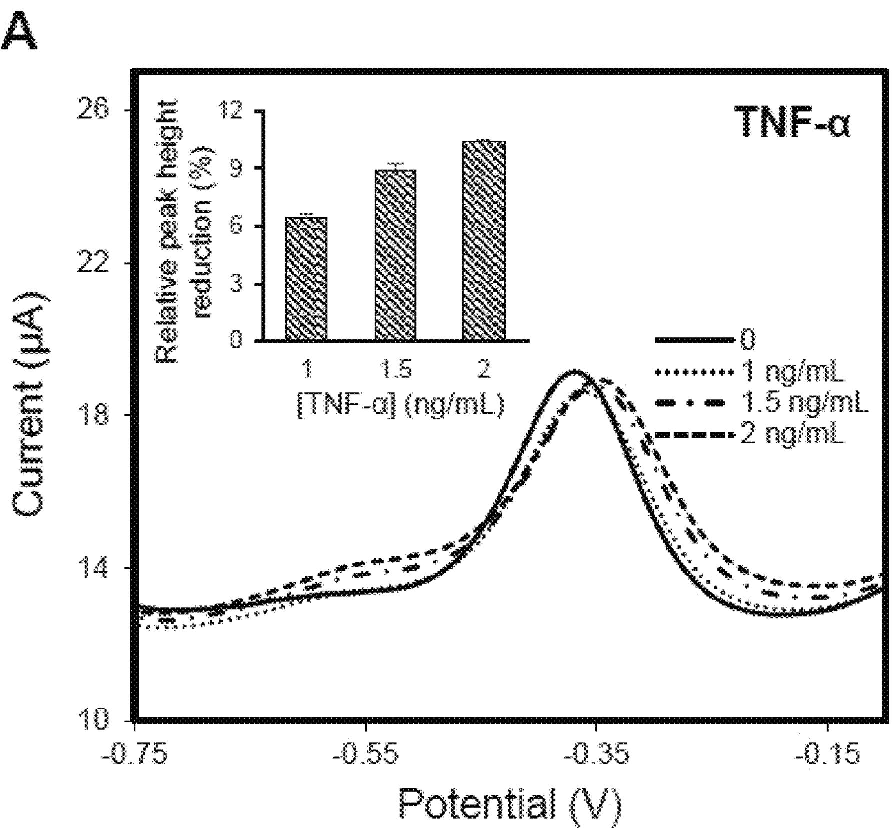
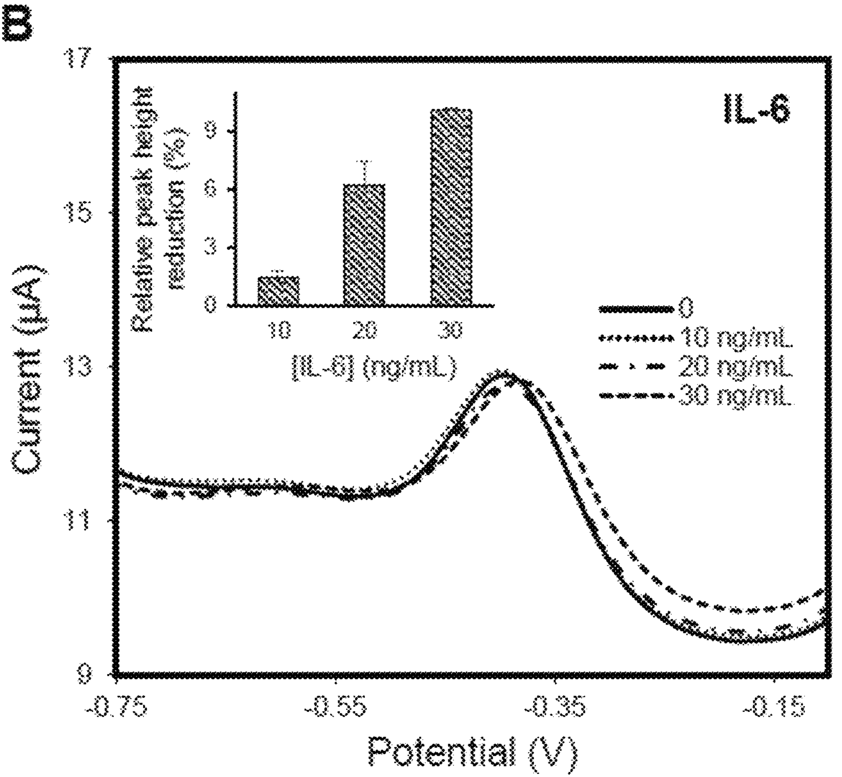
Figure 17A-B

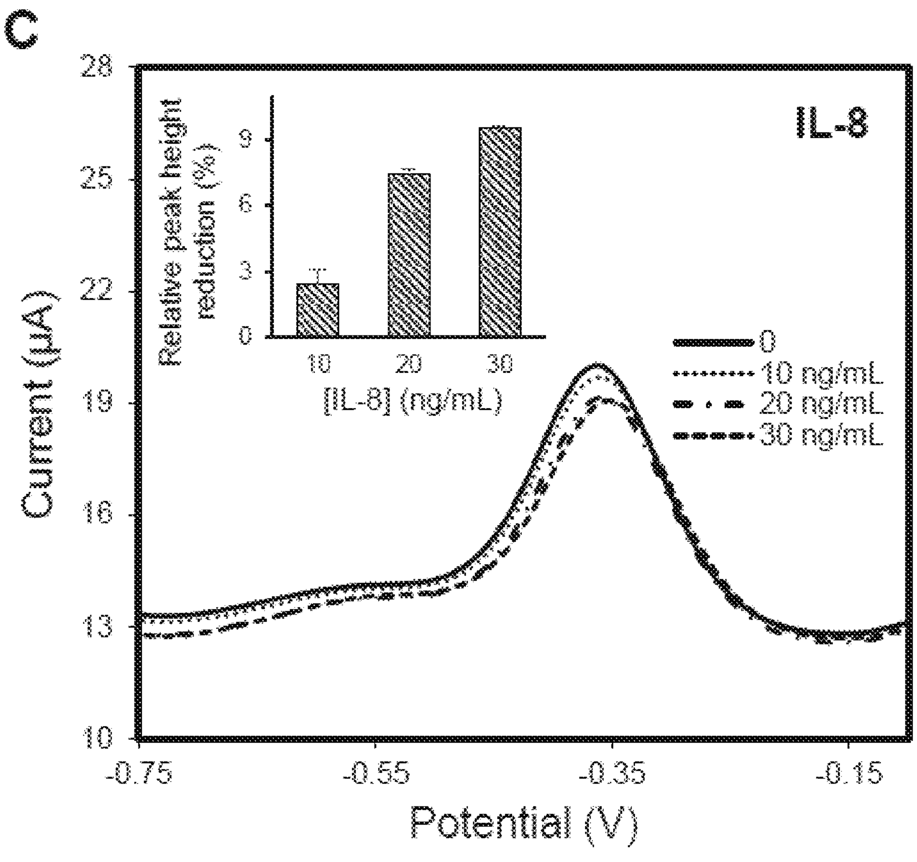
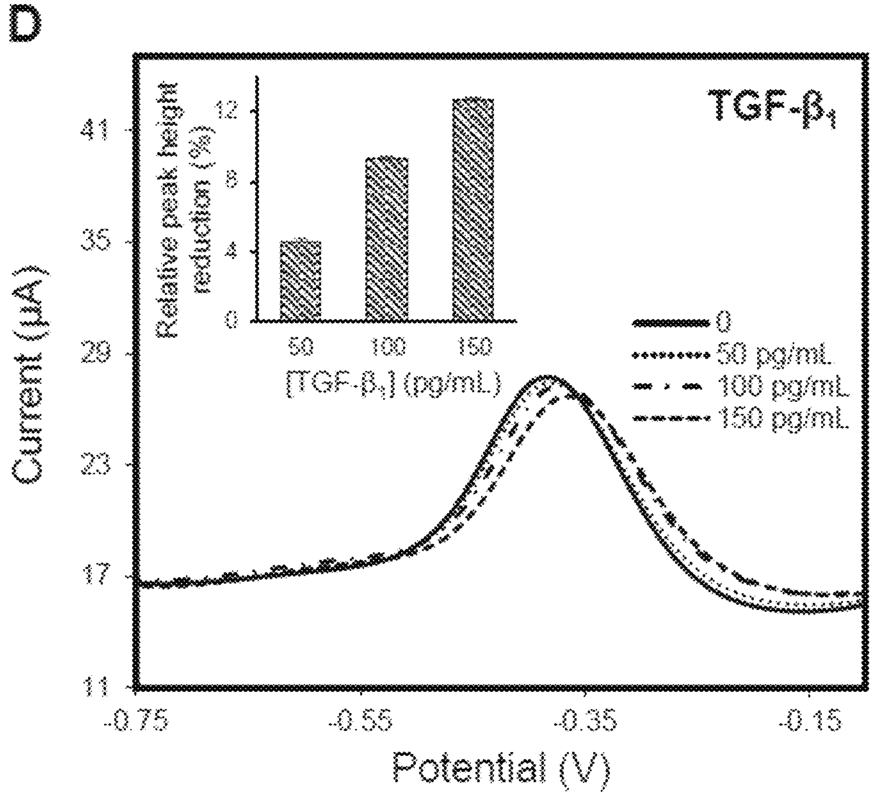
Figure 17C-D

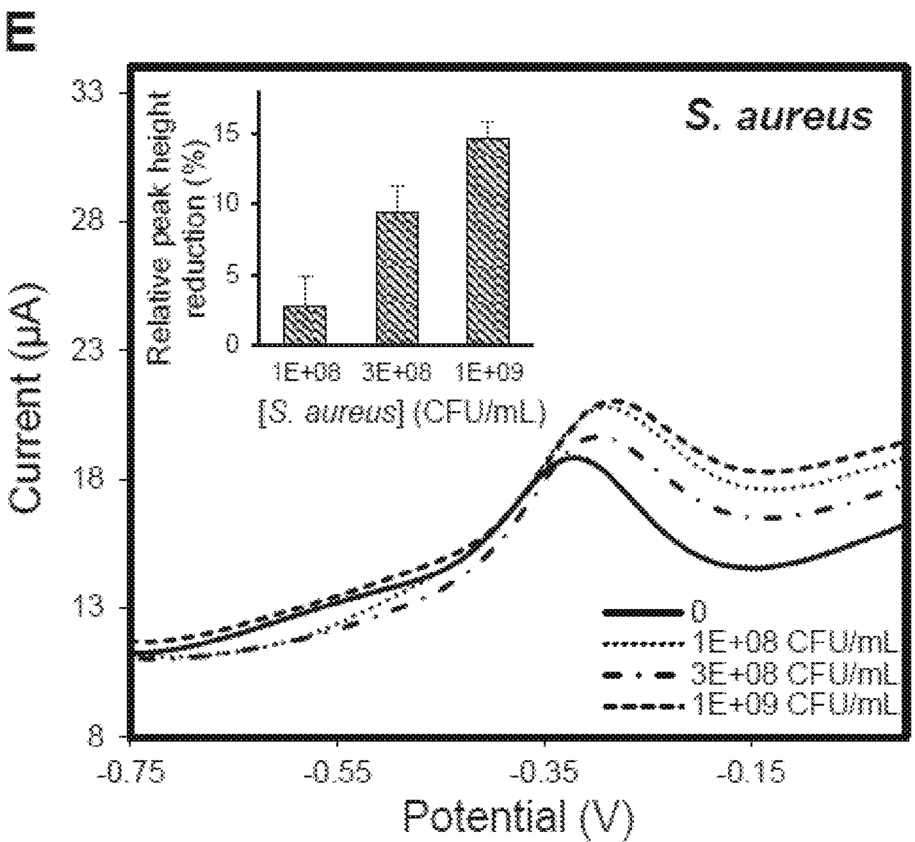
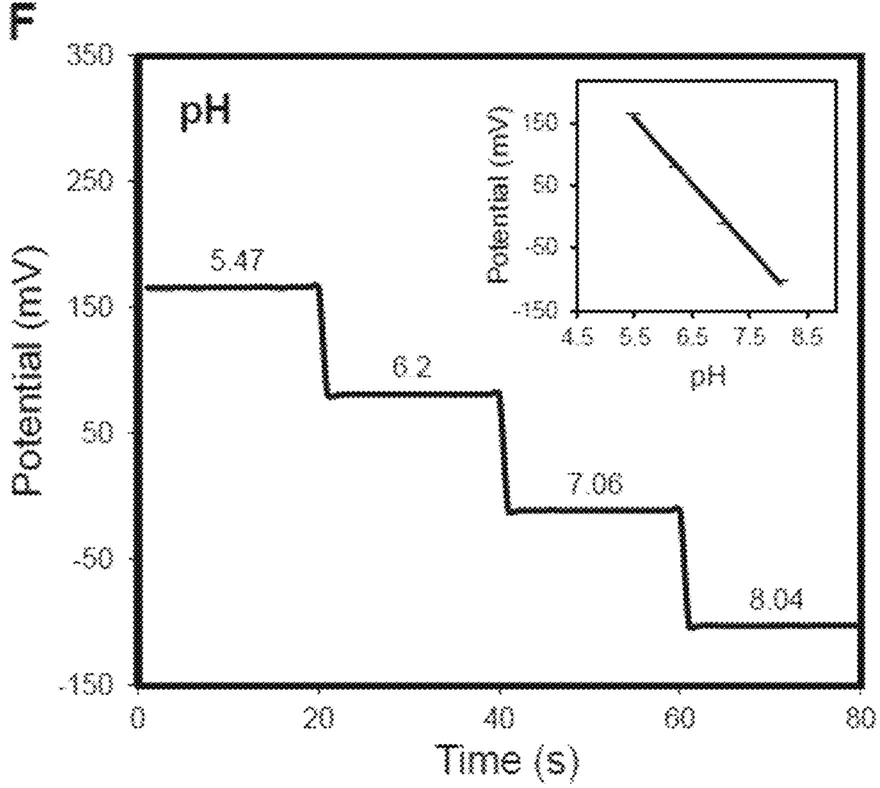
Figure 17E-F

THIN, FLEXIBLE WEARABLE IMMUNOSENSOR FOR DETECTION OF MULTIPLE BIOMARKERS/TARGETS IN BODILY FLUIDS

FIELD OF THE INVENTION

The present invention relates to a layered dressing comprising a biosensor sensing array configured to detect one or more markers in wound fluid.

BACKGROUND

Chronic wounds are debilitating disorders that can cause severe distress to afflicted patients. Globally, they pose an increasing social and financial burden to healthcare systems due to increasingly ageing populations. For example, venous ulcers require long-term therapeutics to heal, have a prevalence of up to 15% of people aged over 70 and recurrence rates varying from 54% to 78%. Chronic wounds result from failure to undergo the natural healing process due to multiple environmental and physiological factors. These factors are reflected in the composition of the wound exudate fluid, which exhibits a dynamic mixture of cytokines, growth factors, and microorganisms during the progression of wound healing.

Clinical assessment of wounds currently relies on planimetry to qualitatively score features such as slough reduction, granulation tissue formation and re-epithelialization. At present, quantitative profiling of the biochemical parameters is generally limited to downstream laboratory testing, such as enzyme-linked immunosorbent assays (ELISA). A non-invasive, point-of-care wound care device that is capable of in situ surveillance of the wound biomarkers would be able to provide timely analysis for more effective diagnosis and treatment. Current flexible sensors designed for wound care are capable of monitoring a limited set of parameters, such as pH, temperature, oxygen, moisture, uric acid, impedance and pressure. However, other markers are also of significant clinical value, such as indicators of inflammatory mediators and bioburdens. For example, cytokines and growth factors are well-established indicators of inflammation during ulcer formation. The microbial composition of a wound is also a key feature of chronic wounds, and is implicated in the inhibition of healing through sustained inflammation, proteolysis and endothelial dysfunction. Based on these indicators, there is a need for a wound sensor that is able to detect these additional biomarkers to allow for improved classifying of the healing status of wounds.

SUMMARY OF THE INVENTION

A wound sensor able to overcome the problems associated with existing sensors discussed above would be able to better guide clinical wound management as compared to just through visual inspection or single-marker measurement. Moreover, a wound sensor incorporated into a dressing would provide constant in situ monitoring of a wound and the wound healing process (e.g. monitoring of the wound microenvironment, inflammation and infection state).

The inventors have surprisingly found that a wound sensor capable of detecting multiple relevant biomarkers may be provided as described herein. The invention therefore provides a number of advantages over traditional single-marker sensors, including a biosensor sensing array that is able to simultaneously detect a wide variety of relevant biomarkers and can be tuned to novel biomarkers using aptamer-based sensors, effective and efficient delivery of wound fluid to the biosensor sensing array by use of capillary action, and the ability to wirelessly connect to controllers.

The invention therefore provides the following.

1. A layered dressing comprising:

a permeable wound contact layer for placing in contact with a wound;

a breathable barrier layer;

a fluid collection layer disposed between the wound contact layer and breathable barrier layer, the fluid collection layer comprising a biosensor housing portion and a fluid collection portion comprising a plurality of channels each having a terminus at the biosensor housing portion; and a biosensor sensing array comprising one or more electrodes, the biosensor sensing array being disposed between the biosensor housing portion of the fluid collection layer and the breathable barrier layer, wherein:

the channels within the fluid collection portion of the fluid collection layer are configured such that, when in use, the channels deliver wound fluid by capillary action from a wound in contact with the wound contact layer to the biosensor sensing array, and where the biosensor sensing array is configured to detect one or more markers in said wound fluid.

2. The layered dressing according to Clause 1, wherein the wound contact layer comprises a plurality of perforations.

3. The layered dressing according to Clause 1 or 2, wherein the fluid collection portion of the fluid collection layer has an annular shape having an outer surface, where annular shape defines a central portion, and where the biosensor housing portion of the fluid collection layer is located at the central portion.

4. The layered dressing according to Clause 3, wherein the fluid collection portion has an outer surface, and where the plurality of channels each run from the outer surface of the fluid collection portion to the biosensor housing portion.

5. The layered dressing according to any one of Clauses 1 to 4, wherein the plurality of channels are configured to allow the flow of fluid from a wound in only a single direction along the channels.

6. The layered dressing according to Clause 5, wherein the plurality of channels each comprise a plurality of interconnected half-open saw-tooth-shaped capillary channels.

7. The layered dressing according to any one of Clauses 1 to 6, wherein the plurality of channels do not have uniform width throughout their length.

8. The layered dressing according to Clause 7, wherein the channels comprise a first portion configured to draw fluid from a wound in contact with the wound contact layer, and a second portion proximal to the biosensor sensing array as compared to the first portion, where the width of the channels at the first portion is greater than the width of the channels at the second portion.

9. The layered dressing according to Clause 8, wherein the channels comprise a first end and a second end, and where the width of the channels at the first end is from about 180 μm to about 220 μm, and the width of the channels at the second end is from about 140 μm to about 180 μm.

10. The layered dressing according to any one of the preceding Clauses, wherein the biosensor sensing array comprises one or more electrodes, each electrode being configured to detect a marker selected from the group consisting of a healing biomarker and a bioburden biomarker.

11. The layered dressing according to Clause 10, wherein the healing biomarker is selected from the group consisting of TNF-α, IL-6, IL-8, TGF-$\beta_1$, and pH.

12. The layered dressing according to Clause 10, wherein the bioburden biomarker comprises a biomarker for *S. aureus*.

13. The layered dressing according to any one of Clauses 10 to 12, wherein the biosensor sensing array comprises two or more electrodes, each electrode being configured to detect a marker selected from the group consisting of TNF-α, IL-6, IL-8, TGF-$\beta_1$, pH and a biomarker for *S. aureus*.

14. The layered dressing according to Clause 13, wherein the biosensor sensing array comprises six electrodes, each electrode being configured to detect a marker selected from the group consisting of TNF-α, IL-6, IL-8, TGF-$\beta_1$, pH and a biomarker for *S. aureus*, such that the biosensor sensing array is able to simultaneously detect TNF-α, IL-6, IL-8, TGF-$\beta_1$, pH and a biomarker for *S. aureus*.

15. The layered dressing according to any one of Clauses 12 to 14, wherein the biomarker for *S. aureus* is an epitope.

16. The layered dressing according to any one of the preceding Clauses, wherein the biosensor sensing array comprises one or more aptamer-based working electrodes, each comprising an aptamer bonded to an electrode, where the aptamer is suitable for detecting a marker in the wound fluid.

17. The layered dressing according to Clause 16, wherein the one or more aptamer-based working electrodes comprises an aptamer for IL-8, IL-6, TNF-α, TGF-$\beta_1$ and/or *S. aureus*.

18. The layered dressing according to Clause 17, wherein any one of the following applies:

(a) the aptamer for IL-8 comprises the sequence 5'-/5ThioMC6-D/rGrGrGrGrGrCrUrUrArUrCrArUrUrCrCrArUrUrUrArGrUrGrUrUrArUrGrArUrArArCrC/3MeBIN/-3'; and/or (b) the aptamer for IL-6 comprises the sequence 5'-/5ThioMC6-D/GGTGGCAGGAGGACTATTTATTTGCTTTTCT/3MeBIN/-3'; and/or (c) the aptamer for TNF-α comprises the sequence 5'-/5MeBIN/rG*rG*rA*rG*rU*rA*rU*rC*rU*rG*rA*rU*rG*rA*rC*rA*rA*rU*rU*rC*rG*rG*rA*rG*rC*r U*rC*rC/3ThioMC3-D/-3'; and/or (d) the aptamer for TGF-$\beta_1$ comprises the sequence 5'-/5MeBIN/CG*CTCGG*CTTC*ACG*AG*ATT*CGTGT*CGTTGTGT*C*CTGT*A*C*C*CG*C*C TTG*A*C*C*AGT*C*ACT*CT*AG*AGC*AT*C*CGG*A*CTG/iSpC3/3ThioMC3-D/-3'; and/or (e) the aptamer for *S. aureus* comprises the sequence 5'-/5ThioMC6-D/TCGGCACGTTCTCAGTAGCGCTCGCTGGTCATCCCACAGCTACGTC/3MeBIN/-3'.

19. The layered dressing according to Clause 18, wherein:

(a) the aptamer for IL-8 comprises the sequence 5'-/5ThioMC6-D/rGrGrGrGrGrCrUrUrArUrCrArUrUrCrCrArUrUrUrArGrUrGrUrUrArUrGrArUrArArCrC/3MeBIN/-3'; and/or (b) the aptamer for IL-6 comprises the sequence 5'-/5ThioMC6-D/GGTGGCAGGAGGACTATTTATTTGCTTTTCT/3MeBIN/-3'.

20. The layered dressing according to any one of Clauses 16 to 20, wherein the aptamer comprises a first end region and a second end region, and where the aptamer is bonded to the electrode via the first end region.

21. The layered dressing according to Clause 20, wherein the surface of the one or more aptamer-based working electrodes comprises a layer of electrochemically exfoliated graphene-gold nanoparticles (AuNPs-GP) nanocomposite.

22. The layered dressing according to Clause 21, wherein the aptamer is bonded to the surface of the electrode by a gold-thiol bond.

23. The layered dressing according to any one of Clauses 16 to 22, wherein the aptamer is conjugated to a redox label, optionally wherein the redox label is methylene blue.

24. The layered dressing according to Clause 23, wherein the aptamer comprises a first end region and a second end region, where the aptamer is bonded to the biosensor via the first end region and the aptamer is conjugated to the redox label via the second end region.

25. The layered dressing according to any one of the preceding Clauses, wherein the biosensor sensing array comprises a polyaniline pH sensor.

26. The layered dressing according to any one of the preceding Clauses, wherein the biosensor sensing array comprises a temperature sensor, optionally wherein the temperature sensor comprises a Wheatstone bridge.

27. The layered dressing according to any one of the preceding Clauses, wherein the biosensor sensing array is capable of wirelessly transmitting measurement data to a paired device.

BRIEF DESCRIPTION OF THE FIGURES

FIG. 1A shows an illustration of a biomarker analytical dressing applied onto an open wound of venous ulcer patients for in situ wound surveillance.

FIG. 1B shows a layered dressing comprising a permeable wound contact layer 1011, a fluid collection layer 1012, a biosensor sensing array 1013, and a breathable barrier layer 1014. The fluid collection layer is inspired by the skin of the Texas horned lizard 1015 enabling pre-determined flow direction towards the lizard's snout defying gravity.

FIG. 2B shows the mechanism of a directional liquid transport system exploiting the interconnection of adjacent saw-tooth-shaped capillary channels.

FIGS. 2C-D together show a COMSOL simulation of liquid transport in the interconnected capillary channels with decreasing width in forward and reverse directions with time, respectively (black, liquid; white, air).

FIG. 4A shows the design of a wound monitoring study.

FIG. 4B shows a photograph of a freely moving mouse with an immunosensor mounted on a skin wound.

FIG. 4C shows a photograph of excisional wounds. The immunosensor is in direct contact with right wound while the left wound acts as control.

FIGS. 4E-F show images of the wounds (scale bar, 5 mm) and changes in wound area from Day 0 to 5. Error bars in F show standard deviation.

FIG. 4G shows a comparison of wound area on Day 1, 3 and 5 (cumulative total 2, 3 and 4 hours of sensor contact). Error bars show standard error.

FIGS. 4H-I show H&E images (20× stitches) of whole full-thickness wounds on Day 3, and wound edges on Day 1, 3 and 5, respectively (scale bars, 1000, 250 μm). Dotted lines show reepithelialization.

FIGS. 4J-K show comparisons of epidermal thickness and reepithelization distance, respectively. Error bars show standard error.

FIGS. 4L-N show H&E images of whole wounds on Day 5, dermis at wound edges on Day 1, 3 and 5, and area of granulation tissue on Day 5, respectively (scale bars, 1000, 250, 250 μm). Images are typical representations across all mice. Statistical comparisons use Wilcoxon signed-rank test (ns=Non-Significant Result).

FIG. 5B shows patient-specific correlation matrices of parameters assessed by the immunosensor (pH, *S. aureus*, IL-6, IL-8, TNF-α, TGF-β1) and the wound size over a five-week period. The total number and duration of wounds (in month) are shown in the table for each patient. Upper left, lower left and lower right are male, upper middle and upper right are female. Scale bar represents Pearson's correlation coefficient ($r_p$).

FIGS. 8A-8D show CV scans of AuNPs-GP/Au at different scan rates. (b) Variation of anodic and cathodic peak current with respect to the square root of scan rate. (c) EIS assessment of bare Au, AuNPs-GP/Au, Apt/AuNPs-GP/Au, MCH/Apt/AuNPs-GP/Au, and TNF-α/MCH/Apt/AuNPs-GP/Au. (d) CV analysis of bare Au, AuNPs-GP/Au, Apt/AuNPs-GP/Au, MCH/Apt/AuNPs-GP/Au, and TNF-α/MCH/Apt/AuNPs-GP/Au.

FIGS. 9A-9H show optimizations of aptasensors and reproducibility studies. (a) Comparison of the SWV scans of the TNF-α sensor with aptamer density of 10 μM and 1 μM. (b) The aptamer density effect on signal-noise-ratio of the TNF-α sensor. (c-g) Incubation duration effect on aptamer target binding equilibrium for the TNF-α, TGF-β1, IL-8, IL-6, and *S. aureus* sensors, respectively. (h) Reproducibility study on two separate TNF-α sensors. Error bars denote the standard deviation of the mean derived from three scans under same conditions.

FIG. 10 shows selectivity studies of the (a) TNF-α, (b) TGF-β1, (c) IL-8, and (d) IL-6 sensors. Error bars denote the standard deviation of the mean derived from three scans under same conditions.

FIGS. 11A-F show characterization, repeatability and reproducibility studies of the pH sensor. (a) Realtime OCP change in serum as the pH values alternated between acid and alkaline over three cycles. (b) Reproducibility study on four separate pH sensors in serum. (c) Real-time OCP toward different pH values. The inset of (c) shows the calibration of the OCP versus pH values in plasma. Error bars denote the standard deviation of the mean over a 20 s span under same conditions. (d) Real-time OCP change in plasma as the pH values alternated between acid and alkaline over three cycles. (e) Reproducibility study on four separate pH sensors in plasma. (f) Comparison of the calibrations in serum and plasma.

FIGS. 12A-C shows the ability of the biosensor to be resized. (a) Minimum volume required for the immunosensor under different sizes. (b) Optical images of the immunosensor with a larger sensing area (diameter of 16 mm) and a smaller sensing area (diameter of 8 mm), respectively. (c) Comparison of signal:noise ratio for 8 mm and 16 mm sensors.

FIG. 14 shows characterization of a mouse TNF-α sensor. The sensor showed decreasing peak current height with the increase of mouse TNF-α concentration (part A). The relative reduction of peak height normalized to peak height against no mouse TNF-α is shown in part B.

FIGS. 17A-17F show the performance of the aptamer-based sensors for varying analyte concentrations.

DETAILED DESCRIPTION

Figure 1C:
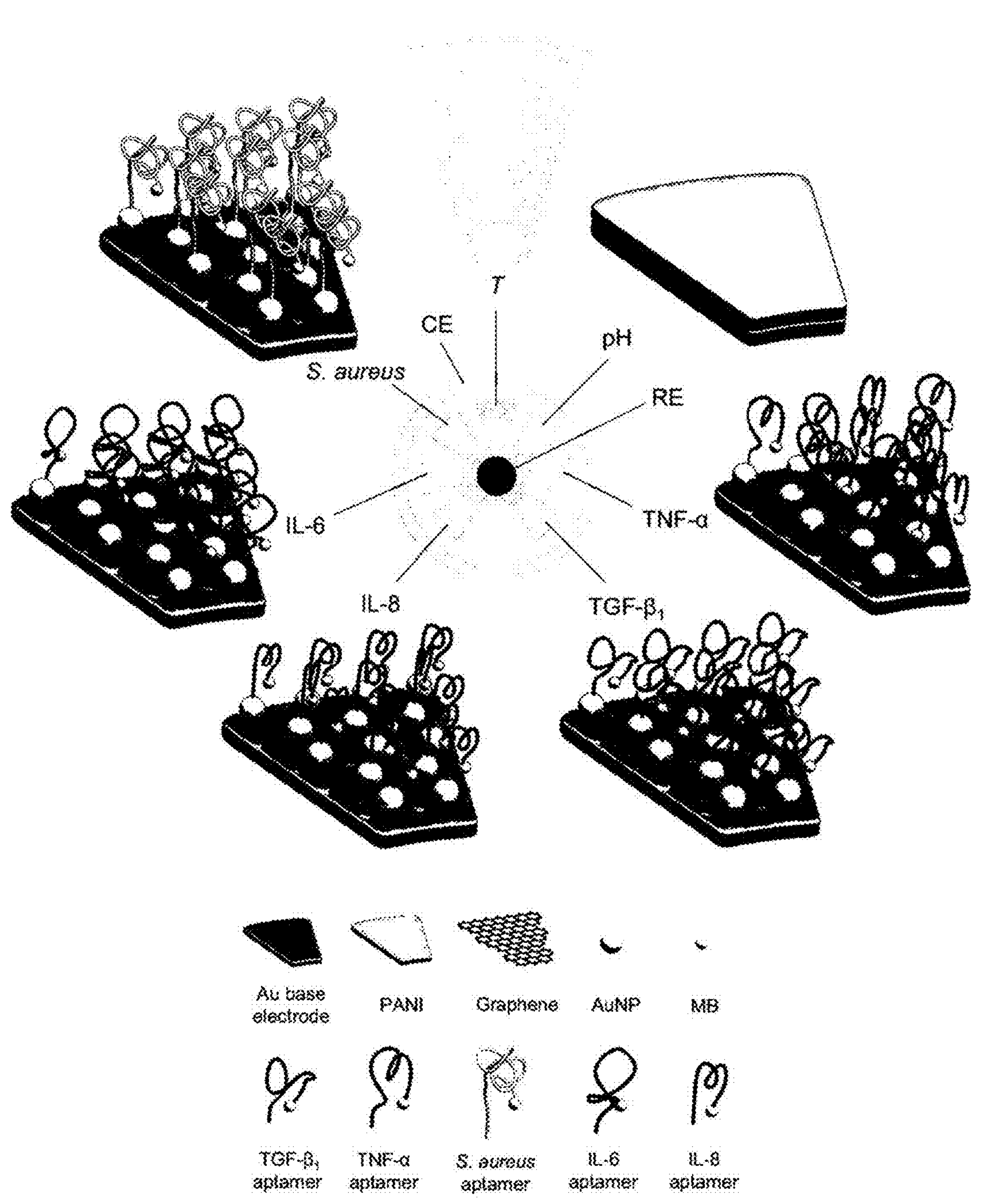
FIG. 1C shows a schematic of the biosensor sensing array configured for detection of TNF-α, IL-6, IL-8, TGF-β1, *S. aureus*, pH and temperature.

The invention provides a layered dressing comprising:

- a permeable wound contact layer for placing in contact with a wound;
- a breathable barrier layer;
- a fluid collection layer disposed between the wound contact layer and breathable barrier layer, the fluid collection layer comprising a biosensor housing portion and a fluid collection portion comprising a plurality of channels each having a terminus at the biosensor housing portion; and a biosensor sensing array comprising one or more electrodes, the biosensor sensing array being disposed between the biosensor housing portion of the fluid collection layer and the breathable barrier layer, wherein:

the channels within the fluid collection portion of the fluid collection layer are configured such that, when in use, the channels deliver wound fluid by capillary action from a wound in contact with the wound contact layer to the biosensor sensing array, and where the biosensor sensing array is configured to detect one or more markers in said wound fluid.

In embodiments herein, the word "comprising" may be interpreted as requiring the features mentioned, but not limiting the presence of other features. Alternatively, the word "comprising" may also relate to the situation where only the components/features listed are intended to be present (e.g., the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

In embodiments herein, various features may be described in the singular or the plural. It is herein explicitly contemplated that references to the singular are to be understood as including the plural, and references to the plural are to be understood as including the singular, unless such an interpretation would be technically illogical.

The permeable wound contact layer serves to protect the rest of the layered dressing from direct contact with the wound bed and minimises disruption of granulating tissue. The wound contact layer is permeable so that it allows the wound to breathe, and also allows moisture to escape. In addition, the permeable wound contact layer allows wound fluid to pass from a wound to the fluid collection layer. In some embodiments of the invention, the permeability may be provided by a plurality of perforations, i.e. the wound contact layer may comprise a plurality of perforations. Suitable materials for the wound contact layer are known to a person skilled in the art, and include polymers such as polyurethane and PDMS, (e.g. polyurethane such as perforated polyurethane).

The breathable barrier layer is in general the outermost layer of the layered dressing, and protects the layered dressing from the external environment whilst also allowing the skin to breathe and moisture to escape. In some embodiments, the breathable barrier layer may be a waterproof breathable barrier layer, which provides protection for the layered dressing and wound. The breathable barrier layer may be made from any suitable material, for example polymers such as polyurethane and PDMS (e.g. polyurethane).

The fluid collection layer performs the function of collecting wound fluid and directing it to the biosensor sensing array. In other words, the fluid collection layer serves to direct fluid that passes through the permeable wound contact layer towards the biosensor sensing array. Due to gravity, wound fluid may not inherently be directed towards a biosensor, and this may be overcome using capillary action. Thus, the fluid collection layer comprises a biosensor housing portion and a fluid collection portion comprising a plurality of channels each having a terminus at the biosensor housing portion. The channels within the fluid collection portion of the fluid collection layer are configured such that, when in use, the channels deliver wound fluid by capillary action from a wound in contact with the wound contact layer to the biosensor sensing array.

The fluid collection layer may have any shape/layout that allows fluid to be transported from a wound to the biosensor sensing array by capillary action (i.e. from the fluid collection portion to the biosensor housing portion). In some embodiments, the fluid collection portion of the fluid collection layer may have an annular shape having an outer surface, where annular shape defines a central portion, and where the biosensor housing portion of the fluid collection layer is located at the central portion. In this way, a large amount of wound fluid may advantageously be directed towards the biosensor housing portion, since wound fluid may be collected from 360° around the biosensor housing portion. In some aspects of this embodiment, the fluid collection portion may have an outer surface, where the plurality of channels each run from the outer surface of the fluid collection portion to the biosensor housing portion.

The fluid collection layer may be made from any suitable materials and by any appropriate method. For example, the fluid collection layer may be made by microfabrication processes or additive manufacturing methods. Suitable materials for the fluid collection layer include epoxy-based materials, such as SU-8 2150.

In some embodiments, the plurality of channels configured to allow the flow of fluid from a wound in only a single direction along the channels. This assists the flow of fluid towards the biosensor housing portion, advantageously increasing the supply of fluid to the biosensor sensing array. In some aspects of this embodiment, this single direction flow of fluid may be achieved when the plurality of channels each comprise a plurality of interconnected half-open saw-tooth-shaped capillary channels. The width of the channels may also vary along their length, since capillary action results in the passage of fluid from a wider width to a smaller width, but generally not in the reverse direction. Thus, some aspects of this embodiment, the channels may comprise a first portion configured to draw fluid from a wound in contact with the wound contact layer, and a second portion proximal to the biosensor sensing array as compared to the first portion, where the width of the channels at the first portion is greater than the width of the channels at the second portion. For example, the channels may comprise a first end and a second end, and where the width of the channels at the first end is from about 180 μm to about 220 μm, and the width of the channels at the second end is from about 140 μm to about 180 μm.

In some embodiments, the permeable wound contact layer, breathable barrier layer and fluid collection layer may all be transparent (or at least substantially transparent). This allows allow easy observation of a healing wound without removal of the layered dressing.

The biosensor sensing array comprises one or more electrodes, and is disposed between the biosensor housing portion of the fluid collection layer and the breathable barrier layer. Thus, the biosensor sensing array is located such that fluid flowing towards the biosensor housing portion of the fluid collection layer contacts the biosensor sensing array, allowing detection of biomarkers in the fluid. The biosensor sensing array is configured to detect one or more markers in said wound fluid. In some embodiments, the biosensor sensing array comprises one or more electrodes, each electrode being configured to detect a marker selected from the group consisting of a healing biomarker and a bioburden biomarker. For example, the healing biomarker may be selected from the group consisting of TNF-α, IL-6, IL-8, TGF-$\beta_1$, and pH. An example of a bioburden biomarker is a biomarker for *S. aureus*, but a skilled person will appreciate that it may be desirable to detect other pathogenic bioburdens.

In some embodiments, the biosensor sensing array may comprise two or more electrodes, with each electrode being configured to detect a relevant biomarker. For example, the biosensor sensing array may comprise two or more electrodes, with each electrode being configured to detect a marker selected from the group consisting of TNF-α, IL-6, IL-8, TGF-$\beta_1$, pH and a biomarker for *S. aureus*. In some embodiments, the biosensor sensing array may comprise six electrodes, with each electrode being configured to detect a marker selected from the group consisting of TNF-α, IL-6, IL-8, TGF-$\beta_1$, pH and a biomarker for *S. aureus*. In this way, the biosensor sensing array may be able to simultaneously detect TNF-α, IL-6, IL-8, TGF-$\beta_1$, pH and a biomarker for *S. aureus*.

Pathogens, such as bacteria (e.g. *S. aureus*) may be detected by detection of an epitope.

In some embodiments, the biosensor sensing array may comprise one or more aptamer-based working electrodes. As used herein, an aptamer-based working electrode means an electrode that is conjugated or otherwise bonded to an aptamer. An aptamer-based working electrode may comprise an aptamer for a biomarker that is desired to be detected, such as IL-8, IL-6, TNF-α, TGF-$\beta_1$ and/or *S. aureus*.

In some embodiments, the aptamer in an aptamer-based working electrode may be bonded to the surface of the electrode at its 5' or 3' end, or at another point in the aptamer. In some embodiments of the invention, the aptamer-based working electrode may be bonded to the surface of the electrode at its 5' or 3' end, for example at its 5' end. In more general terms, the aptamer may comprise a first end region and a second end region, where the aptamer is bonded to the electrode via the first end region.

Figure 3A:
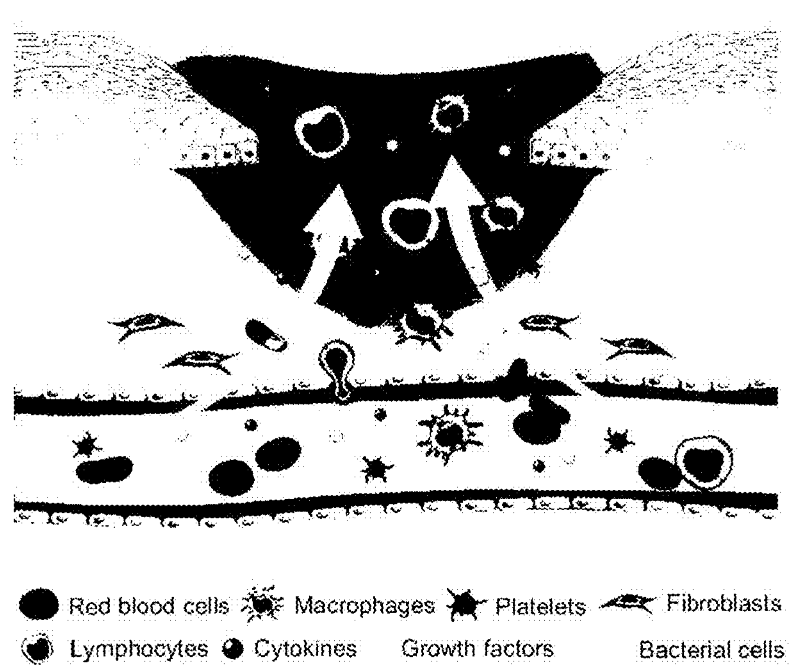
FIG. 3A shows an illustration of a microenvironment of venous ulcers.
Figure 3B:
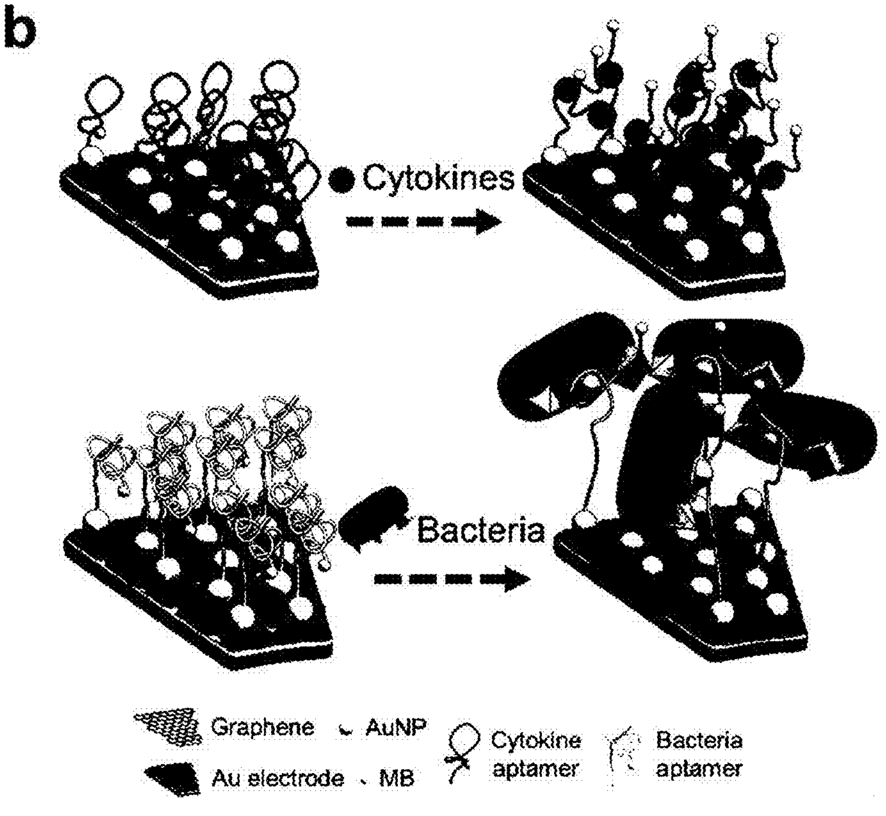
FIG. 3B shows a schematic of the sensing mechanism of the aptamber-based biosensors for cytokine and bacteria detection, respectively.

The aptamer-based working electrode may comprise a redox label, such as a redox label at the opposite end to that bonded to the electrode. For example, the aptamer may be bonded to the electrode via the first end region and conjugated to the redox label via a second end region. Thus, when the aptamer is bonded to the surface of the electrode at its 5' end, the aptamer may comprise a redox label at the 3' end. This may be advantageous since as illustrated in FIG. 3B, in the absence of the biomarker bound by the aptamer, the redox label may be in proximity to the surface of the electrode, allowing electron transfer. A Faradaic current may then be detected electrochemically. Upon binding of the aptamer to the biomarker, the hairpin structure of the aptamer may undergo a conformational change during which redox label moves away from the electrodes, causing a decreased redox current. Thus, the aptamer-based sensors require no additional reagent to accomplish the electrochemical measurement in a single step, which makes them appropriate for in situ analysis and independent from downstream analysis. A particular example of a suitable redox label that may be mentioned herein is methylene blue.

As will be appreciated by a person skilled in the art, the aptamer-based sensors may be applied to detect almost any relevant biomarker. Specific examples of aptamer sequences that may be useful in the invention are provided below, but a skilled person would understands that other aptamer sequences may be used within the invention.

A suitable aptamer for IL-8 comprises the sequence 5'-/5ThioMC6-D/rGrGrGrGrGrCrUrUrArUrCrArUrUrCr-CrArUrUrUrArGrUrGrUrUrArUrGrArUrArArCrC/3Me-BIN/-3'.

A suitable aptamer for IL-6 comprises the sequence 5'-/5ThioMC6-D/GGTGGCAGGAGGACTATTTAT-TTGCTTTTCT/3MeBIN/-3'.

A suitable aptamer for TNF-α comprises the sequence 5'-/5MeBIN/ rG*rG*rA*rG*rU*rA*rU*rC*rU*rG*rA*rU*rG*rA* rC*rA*rA*rU*rU*rC*rG*rG*rA*rG*rC*r U*rC*rC/ 3ThioMC3-D/-3'.

A suitable aptamer for TGF-$\beta_1$ comprises the sequence 5'-/5MeBIN/ CG*CTCGG*CTTC*ACG*AG*ATT*CGTGT* CGTTGTGT*C*CTGT*A*C*C*CG*C*C TTG*A*C*C*AGT*C*ACT*CT*AG*AGC*AT*C* CGG*A*CTG/iSpC3/3ThioMC3-D/-3'.

A suitable aptamer for *S. aureus* comprises the sequence 5'-/5ThioMC6-D/ TCGGCACGTTCTCAGTAGCGCTCGCTGGTCATCC-CACAGCTACGTC/3MeBIN/-3'.

In some embodiments of the invention:

(a) the aptamer for IL-8 comprises the sequence 5'-/5ThioMC6-D/rGrGrGrGrGrCrUrUrArUrCrArUrUrCr-CrArUrUrUrArGrUrGrUrUrArUrGrArUrArArCrC/3Me-BIN/-3'; and/or (b) the aptamer for IL-6 comprises the sequence 5'-/5ThioMC6-D/GGTGGCAGGAGGACTATTTAT-TTGCTTTTCT/3MeBIN/-3'.

The biosensor sensing array may comprise a pH sensor, for example a polyaniline pH sensor. The biosensor sensing array may comprise a temperature sensor, for example a temperature sensor comprising a Wheatstone bridge.

In embodiments of the invention in which the biosensor sensing array comprises one or more electrodes (such as two or more electrodes, that may be e.g. aptamer-based electrode sensors), the electrodes may comprise a layer of electrochemically exfoliated graphene. In further such embodiments, the surface of the electrode may comprise a layer of electrochemically exfoliated graphene-gold nanoparticles, such that the electrode is modified with a thin layer of electrochemically exfoliated graphene-gold nanoparticles (AuNPs-GP) nanocomposite. In such cases, and when the electrodes are aptamer-based electrode sensors, the aptamer may be bonded to the surface of the electrode by a gold-thiol bond. Without being bound by theory, electrochemically exfoliated graphene (which may also be referred to herein as 'graphene') possesses excellent properties such as high crystallinity, high conductivity, and low oxidation degree. In addition, the presence of the gold is believed to provide high current density, enhanced electron mobility and fast mass transport. The combination of AuNPs and graphene is believed to contribute to enhanced signal scale, high sensitivity and good stability for the aptamer based biosensors.

As explained herein, the biosensor sensing array may be capable of wirelessly transmitting measurement data to a paired device. This may advantageously provide clinicians with easy access to real-time updates of the wound microenvironment.

The layered dressing of the invention may interface directly with wounds (such as venous ulcers) in the form of a bioanalytical dressing that comprises a sensors for a broad panel of healing biomarkers, including inflammatory mediators, bacterial load, and physico-chemical parameters (FIG. 1C). The layered dressing is able to measure highly clinically relevant biomarkers such as tumour necrosis factor-α (TNF-α), interleukin-6 (IL-6) and interleukin-8 (IL-8), which are elevated in wound fluids obtained from non-healing ulcers as compared to healing ulcers. To assess the status of dermal healing in chronic skin lesions, the layered dressing may also detect transforming growth factor-beta1 (TGF-β1), which plays a key role in regulating dermal fibroblast phenotype and function and has been clinically observed in elevated concentrations in exudates from venous ulcers. The physico-chemical markers may additionally include pH, temperature, and bacterial load. The pH of wound exudate is an important biochemical indicator of wound healing status: hard-to-heal wounds generally exhibit alkaline pH, ranging from 7.15 to 8.93. Wound temperature provides information on inflammation and infection: wounds with elevated temperature tend to heal more slowly. *Staphylococcus aureus* (*S. aureus*), a predominant species in all types of chronic wound samples, can be a useful biomarker for bioburden on wounds.

The invention is described in more detail below with reference to the Figures in the below Examples, which are not to be construed as limitative.

EXAMPLES

Materials

Iron(III) chloride ($FeCl_3$), N,N-dimethylformamide (DMF), tetraalkylammonium (TAA), N-methyl-2-pyrrolidone (NMP), potassium hexacyanoferrate(III) ($K_3Fe(CN)_6$), potassium hexacyanoferrate(II) trihydrate ($K_4Fe(CN)_6 \cdot 3H_2O$), potassium chloride (KCl), tris(2-carboxyethyl)phosphine hydrochloride (TCEP), 6-mercapto-1-hexanol (MCH), hydrochloric acid (HCl), aniline, disodium phosphate ($Na_2HPO_4$), citric acid, buffer solution pH 10.00 Certipur®, human serum, and human plasma were purchased from Sigma-Aldrich. PET sheet (ST506) was purchased from MELINEX. Bulk graphite crystals (purity 99.9%) were purchased from HQ graphene. Organic spherical gold nanoparticles (diameter of 20 nm, dispersed in DMF) were purchased from Nanopartz Inc. The modified oligos and IDTE buffer (10 mM Tris, 0.1 mM EDTA) were purchased from Integrated DNA Technologies. Recombinant human TNF-α, IL-6, IL-8, TGF-β1, IL1β, IL-2, IL-7, IFN-γ, recombinant mouse TNF-α, and bovine serum albumin (BSA) were purchased from R & D systems. Phosphate buffered saline (PBS) (1×) without calcium and magnesium was purchased from Lonza. *S. aureus* HG001, was provided by the Department of Microbiology and Immunology at the National University of Singapore. UltraPure™ DNase/RNase-free distilled water, BD Difco™ LB broth, Miller (Luria-Bertani), and Oxoid tryptone soya agar (TSA) were purchased from Thermo Fisher Scientific. RAPID'Staph agar and egg yolk with potassium were purchased from Bio-Rad.

Example 1: Preparation of a Layered Dressing

FIG. 1A shows a biomarker analytical dressing containing an immunosensor applied onto an open wound of venous ulcer patients for in situ wound surveillance. The dressing comprises a permeable wound contact layer 1011, a fluid collection layer 1012, a biosensor sensing array 1013 (also described herein as an immunosensor), and a breathable barrier layer 1014 (FIG. 1B). The permeable wound contact layer comprises a plurality of perforations and is also referred to herein as a perforated wound contact layer. The function of the perforated wound contact layer is to protect the immunosensor from direct contact with the wound bed, minimizing disruption to the granulating tissue. The barrier allows normal skin function by letting oxygen in and moisture vapour out. The dressing substrates may be transparent, which allows convenient observation and evaluation of the wound in situ during application: surface area and colour of the exudate.

Figure 1D:
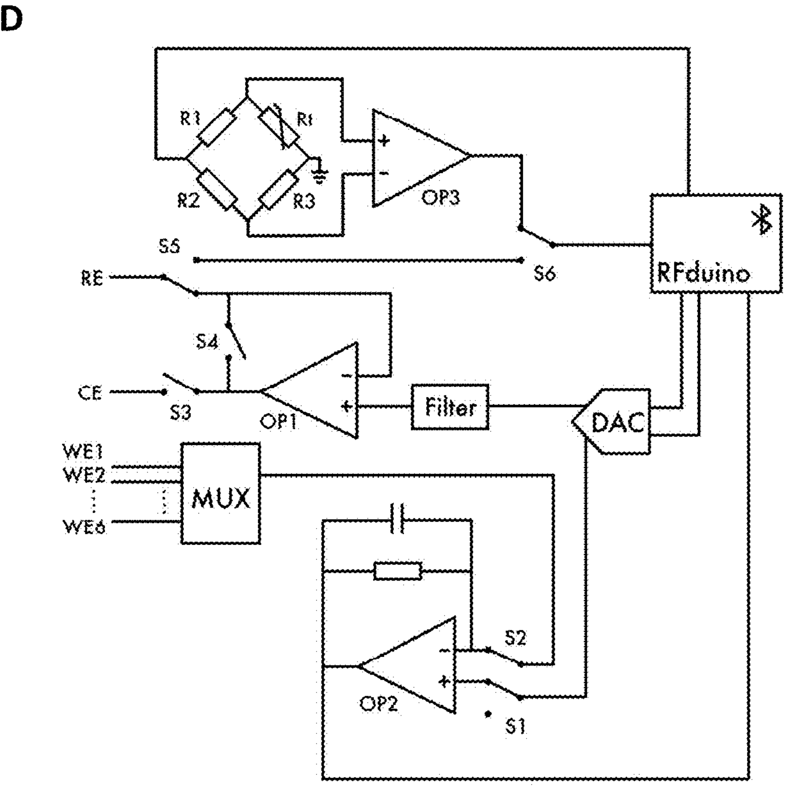
FIG. 1D shows a hardware block diagram for the prototype.

FIG. 1D illustrates the circuit block diagram describing the hardware design. The portable electrochemical analyzer is designed to manage signal transduction and perform electrochemical measurements. Measurement data is wirelessly transmitted to a paired mobile device using Bluetooth Low Energy (BLE). The mobile device may run an accompanying application, containing a GUI to assist the management of patient's profiles and medical records, while facilitating data collection, analysis and visualization (Methods).

Design of the Fluid Collection Layer

Figure 2A:
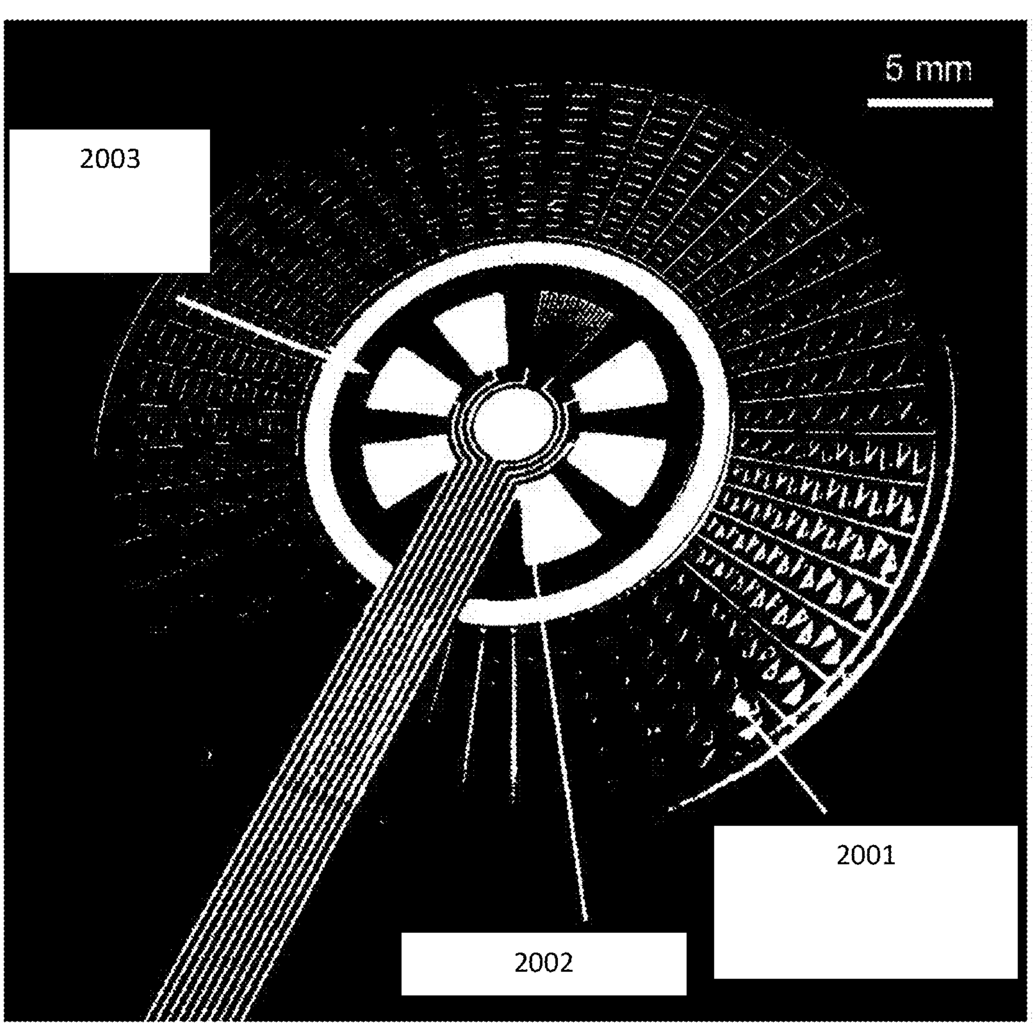
FIG. 2A shows a biomimetic passive microfluidic collector formed by a polar array of interconnected half-open, saw-tooth-shaped capillary channels 2001 with a decreasing width from 200 μm to 160 μm, fabricated on top of the base electrodes of a biosensor sensing array 2002. 2003 shows the direction of the liquid transport.

Efficient wound fluid capture and delivery is essential for accurate in situ biomarker detection. To ensure efficient wound fluid collection, the inventors incorporated a microfluidic layer capable of guiding the wound fluids to the sensing area. A fluid collection layer was designed based on the skin of the Texas horned lizard (*Phrynosoma cornutum*) that enables pre-determined directional fluid flow towards the lizard's snout defying gravity (FIG. 1B). The directional liquid transportability of *Phrynosoma cornutum*'s skin is ascribed to a network of microstructures that forms a special capillary system between the scales. Based on a theoretical model derived from this capillary network, a fluid collection layer was designed with an annular pattern (FIG. 2A). The pattern is composed of a polar array of interconnected half-open, saw-tooth-shaped capillary channels with a decreasing width from 200 μm to 160 μm (outer to inner). The interconnection of adjacent saw-tooth-shaped capillary channels facilitates continuous flow in the forward direction (i.e., towards the sensing area) but inhibits liquid transport in the reverse direction. Specifically, in the forward direction as shown in FIG. 2B, the liquid stops at capillary i due to abrupt widening with infinite meniscus radius, while continuously flowing to capillary ii, where it merges with the stopped fluid at capillary i and flows forward to capillary iv. Similarly, the merged liquid will coalesce with the stopped liquid at capillary iii and keep on flowing to subsequent capillaries. On the other hand, the liquid flow stops at widening sections v and vi in the reverse direction (FIG. 2B). Therefore, a directional liquid transport system is formed.

Figure 6:
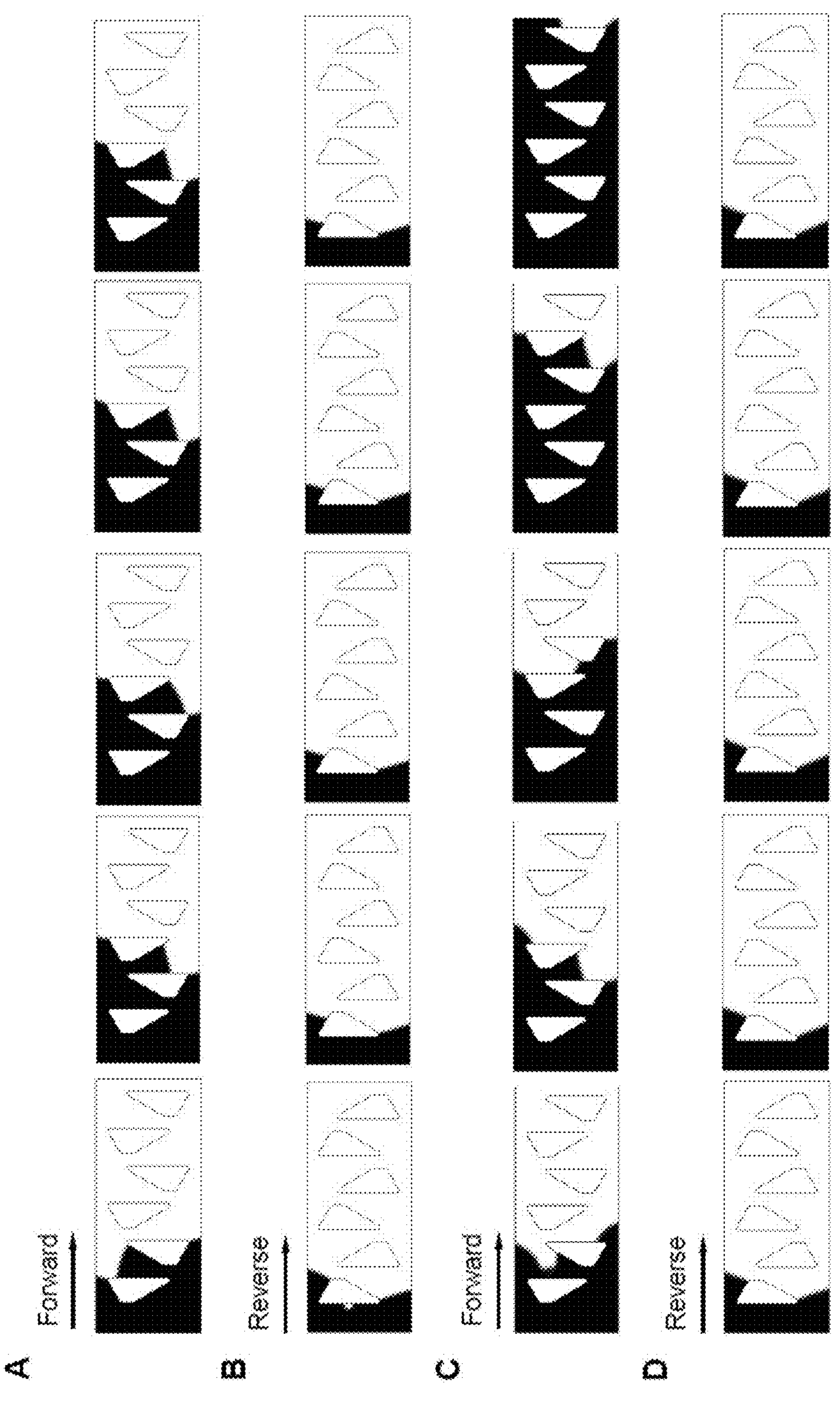
FIG. 6 shows a COMSOL simulation of liquid transport in the interconnected capillary channels with fixed width of (a, b) 200 μm and (c, d) 160 μm in the forward and reverse directions toward time, respectively (black, liquid; white, air).

To demonstrate this working principle, the directional liquid transport system models were built (Methods). Simulation of the liquid transport in the interconnected capillary channels with decreasing width was conducted in both forward and reverse directions, as shown in FIG. 2C-2D. The liquid passed through in the forward direction; it stopped completely at the starting point in the reverse direction. In addition, the liquid transport performance with respect to capillary channel of widths 160 μm and 200 μm were also simulated. It was observed that at width of 200 μm, the liquid failed to flow in the forward direction (FIG. 6 part a), while a continuous flow was observed under the width of 160 μm (FIG. 6 part c). On the other hand, the liquid failed to overcome the starting point in the reverse direction in both capillary channel widths (FIG. 6 parts b and d). Based on these simulation results, the capillary channel with decreasing width can ensure efficient and continuous directional liquid transport towards the sensing area.

Figure 2E:
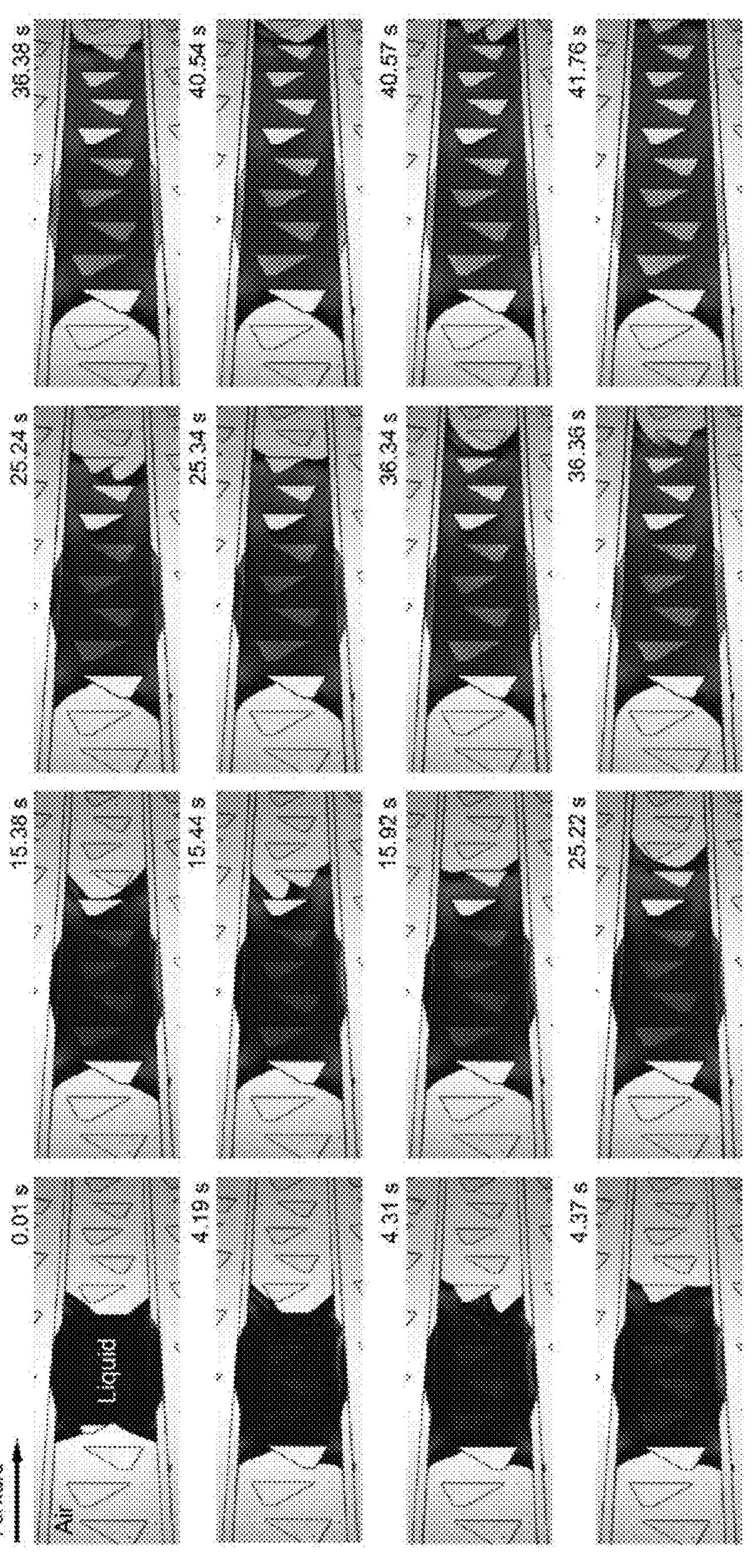
FIG. 2E shows the dynamics of liquid transport process of a biomimetic prototype at different time points (scale bar, 500 μm).
Figure 2F:
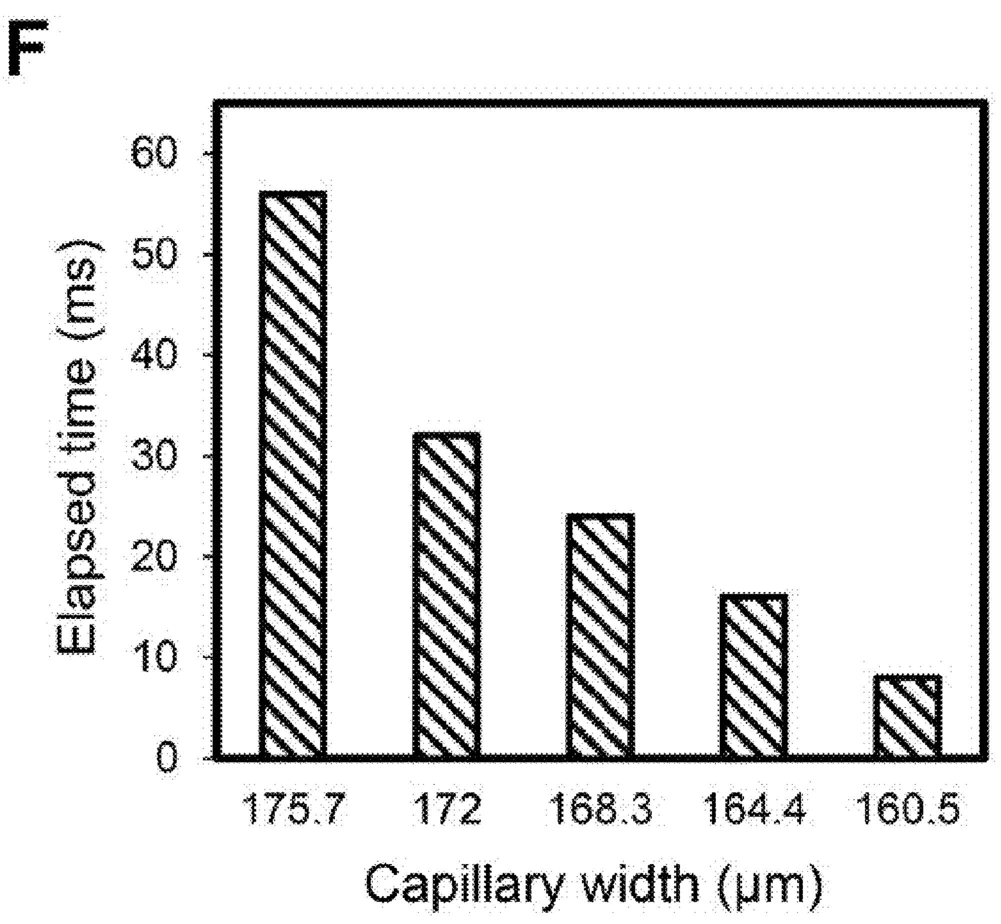
FIG. 2F shows the elapsed time of the liquid transport in capillary channels having consistent length and with decreasing width.

Experimental results obtained using a biomimetic prototype verified the simulation results. Specifically, a droplet (2 μL) of soapy water, which possesses a similar contact angle to human serum, was applied to the middle part of the directional liquid transport system. FIG. 2E illustrates the dynamic passive liquid transport process (Methods) at different times. By consecutively utilizing the interconnected capillary channels, the liquid was transported to the sensing area, whereas the movement in the reverse direction was inhibited. It was also observed that decreasing capillary channel width required shorter liquid transport time in the capillary channels (FIG. 2F). The average flow rate in the forward direction was ~0.43 $mm^3/s$. The design of the directional liquid transport system provided additional ~180% wound fluid capture and delivery to the sensor within 130 s, ensuring reliable sensing performance regardless of the ulcer shape or size.

The simulated experiments for testing the fluid collection layer were performed as follows. Computational Fluid Dynamics (CFD) module (COMSOL Multiphysics 5.3a, Two-Phase Flow, Level Set interface) was used to simulate the directional liquid transport system. The experimental process was recorded using a high-speed camera (FASTCAM Mini AX, Photron) mounted on an inverted microscope system (IX 71, Olympus) with the settings of 125 fps, 1024×1024 resolution.

The fluid collection layer was prepared by spin coating a layer of SU-8 2150 (~150 μm) on top of the breathable barrier layer (which was formed from a layer of medical grade polyurethane film, brand name Tegaderm™). The fluid collection layer was then patterned by photolithography. The wound contact layer was formed from a perforated medical-grade polyurethane film. The preparation of the layers is described in more detail in Methods below.

Design and Characterization of the Biosensor Sensing Array (Immunosensor)

The immunosensor was designed to measure multiple biophysicochemical parameters of sampled wound fluid based on an electrochemical system. It contained a polar array of petal-shaped working electrodes sharing one Ag/AgCl reference electrode at the centre and one Au counter electrode at the periphery (FIG. 1C, Methods), forming a compact circular layout ideal for microvolume analysis. The sensing elements of the TNF-α, IL-6, IL-8, and TGF-β1 electrodes were based on aptamer-analyte affinity, while the binding affinity of the *S. aureus* electrode was between the aptamer and specific epitopes at the surface of bacteria cell wall.

Previous biosensor functionalization methods relied on fabrication techniques specialized to each biomarker that did not allow straightforward integration of multiple sensing modalities. This was overcome using a micro-drop procedure with the aid of micro-wells to functionalize each working electrode with different sensing elements. An optimized height of the micro-well (20 μm) enabled independent drop-casting, aptamer immobilization, and passivation, while also protecting the immobilized aptamers and captured targets from being scratched off (Methods).

Figure 7:
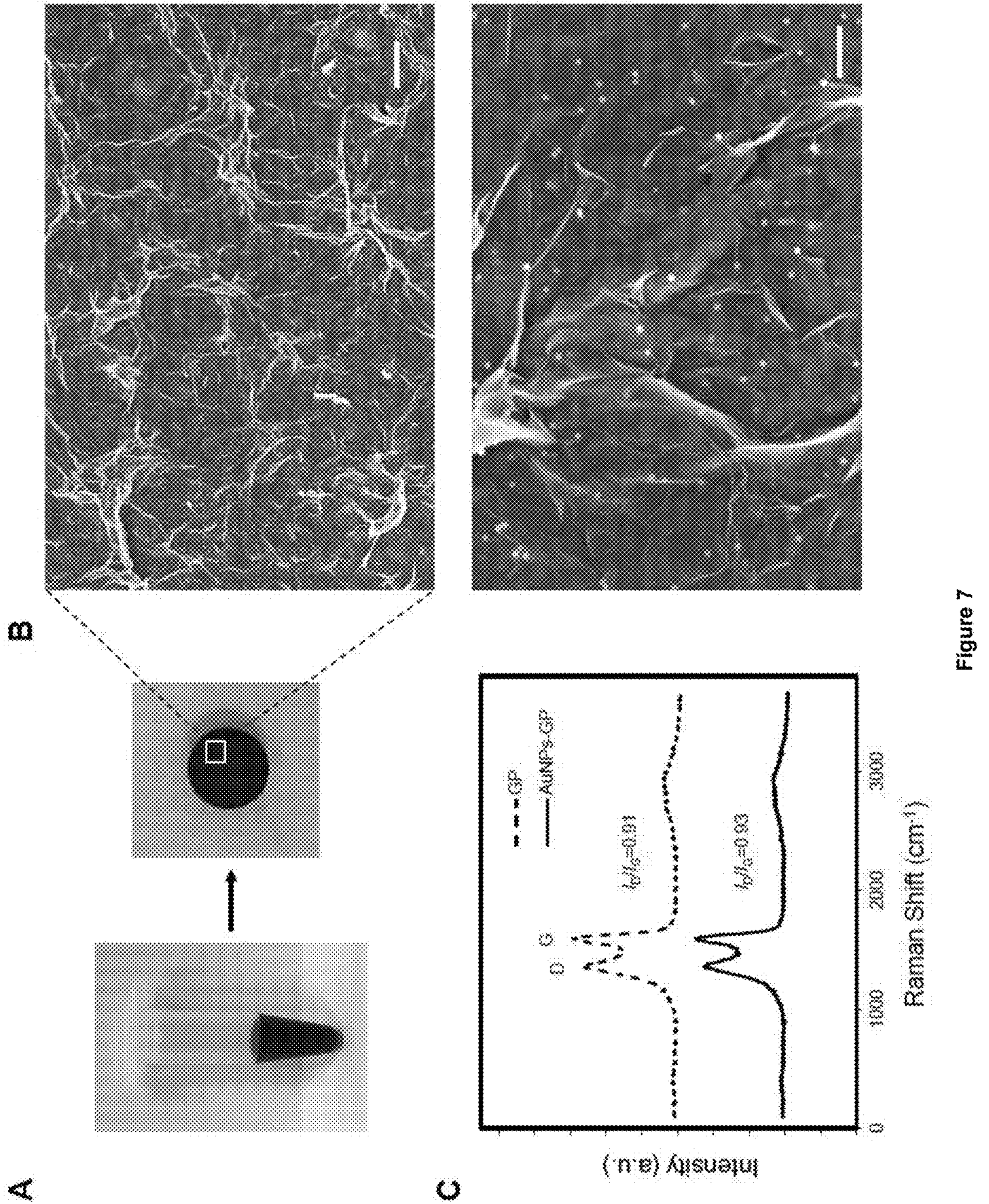
FIG. 7 shows characterization of the AuNPs-GP nanocomposite. (a) The AuNPs-GP dispersion (left) and its drop-casted film (right). (b) FESEM images of the drop-casted AuNPs-GP film (upper: scale bar, 2 μm; bottom: scale bar 200 nm). (c) Raman spectra of graphene and AuNPs-GP nanocomposite.

To optimize the performance of microelectrodes, each aptamer-based electrode was modified with a thin layer of electrochemically exfoliated graphene-gold nanoparticles (AuNPs-GP) nanocomposite (Methods). The morphology of the AuNPs-GP was characterized from Field Emission Scanning Electron Microscope (FESEM) images (FIG. 7 part b). The Raman spectra of graphene and AuNPs-GP nanocomposite are shown in FIG. 7 part c (Methods). The D to G band peak intensity ratio (ID/IG) reflects the degree of disorder in the graphitic material. The ID/IG value of AuNPs-GP (0.93) was slightly larger than that of graphene (0.91), indicating additional defects introduced by AuNPs to the nanocomposite.

Qualitative analysis of the AuNPs-GP modified electrodes was conducted using cyclic voltammetry (CV) at different scan rates, as illustrated in FIG. 8A. The anodic to cathodic peak current ratios (lpa/lpc) was in the range of 0.92-1.15, indicating the quasi-reversibility of the system. Theoretically, the peak current is proportional to the square root of the scan rate. FIG. 8B shows the variation of anodic and cathodic peak current with respect to the square root of the scan rate, with regression coefficients of 0.9867 and 0.9903, respectively. Good linearity indicated diffusion-controlled processes at the electrode.

Aptamer sequences were designed (Methods) modified with methylene blue (MB), a redox label, at one end and a thiol group at the other end for covalent binding to AuNPs. As illustrated in FIG. 3B, in the absence of an analyte, MB is in proximity to the AuNPs-GP modified electrodes, allowing electron transfer. A Faradaic current can be detected electrochemically. Upon target binding, the hairpin structure of the aptamer undergoes a conformational change during which MB moves away from the electrodes, causing a decreased redox current. Owing to the sensing mechanism, the aptamer-based sensors require no additional reagent to accomplish the electrochemical measurement in a single step, which makes it appropriate for in situ determination and independent from downstream analysis. Having advantages of chemical and thermal stability, high affinity and selectivity, and non-immunogenicity, the aptamer based sensor is able to provide a highly advantageous biocompatible molecular analytical dressing. Following aptamer immobilization, the electrode surface may be passivated with 6-mercapto-1-hexanol (MCH) to inhibit non-specific adsorption.

The stepwise assembly of different layers on the working electrode was validated by electrochemical impedance spectroscopy (EIS) (FIG. 8C, Methods). The AuNPs-GP modified electrode had a lower charge transfer resistance (Rct) (3.17 kΩ) than the bare gold electrode (5.29 kΩ), indicating enhanced electron transfer kinetics at the electrode interface with higher electroactive surface area. The immobilization of aptamer and MCH led to an increase of Rct to 14.4 kΩ and 17 kΩ, respectively. The electron mobility was hindered by the immobilized substance. The presence of an analyte further blocked the electron transfer indicated by a raised Rct of 18 kΩ. FIG. 8D reports the CV analysis of different steps where redox peak current is the indicator of conductivity. The results were consistent with those from EIS, verifying that the electrode preparation was successful and functional.

The aptamer-based sensors were characterized using square wave voltammetry (SWV) in order to monitor variations of peak current height associated with the MB redox tag distance to the electrode. Owing to its similar molecular composition to wound fluid, serum was used to mimic wound exudates. The aptamer density of 10 μM was applied to ensure distinguishable peak heights (FIG. 9A) and optimize signal-to-noise ratio (FIG. 9B), where the signal denotes the peak height and noise denotes the standard deviation of the signal. Studies on the incubation process revealed that approximately 30 min is required for the aptamer-target binding to establish equilibrium (FIG. 9C-G). The performance of each aptasensor against analyte with different concentrations is shown in the inset of FIG. 3D-H (Methods). The peak current height was observed to decrease with increased target concentration. The relative reduction of peak height normalized to peak height against no analyte with analyte concentration are exhibited in FIG. 3D-H. Quadratic regression lines exhibit good monotonicity of the TNF-α ($R^2$=0.9798), TGF-β1 ($R^2$=0.9931), IL-8 ($R^2$=0.9958), IL-6 ($R^2$=0.9882), and *S. aureus* ($R^2$=0.9712) sensors. Notably, the concentration ranges of TNF-α (0-2 ng $mL^{-1}$), TGF-β1 (0-150 μg $mL^{-1}$), IL-8 (0-30 ng $mL^-$ and IL-6 (0-30 ng mL-1) were based upon levels reported in wound fluids from venous ulcer patients, combined with ELISA results from clinical samples used for this study. Similarly, the range of *S. aureus* (0-1E+09 CFU mL-1) was selected based on microbial loads reported in wounds, together with CFU enumerations from this study. The cytokine sensors were demonstrated to have good selectivity, minimal interference (FIG. 10), and good reproducibility (FIG. 9H).

Figure 3C:
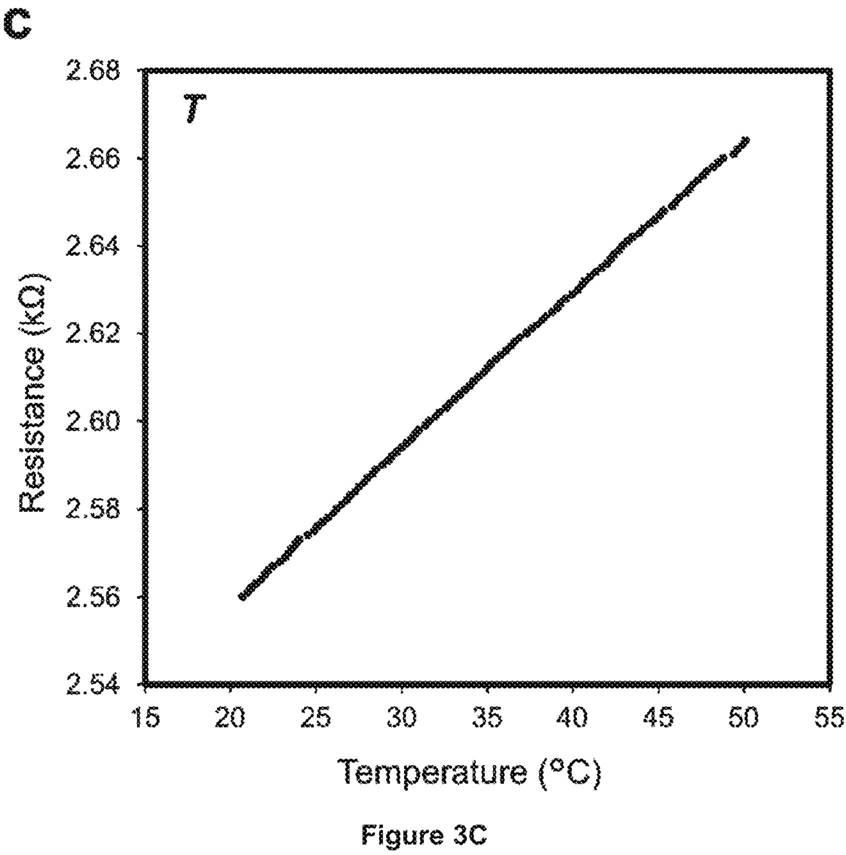
FIG. 3C shows calibration of the resistance of the temperature sensor versus the temperature.
Figure 3D:
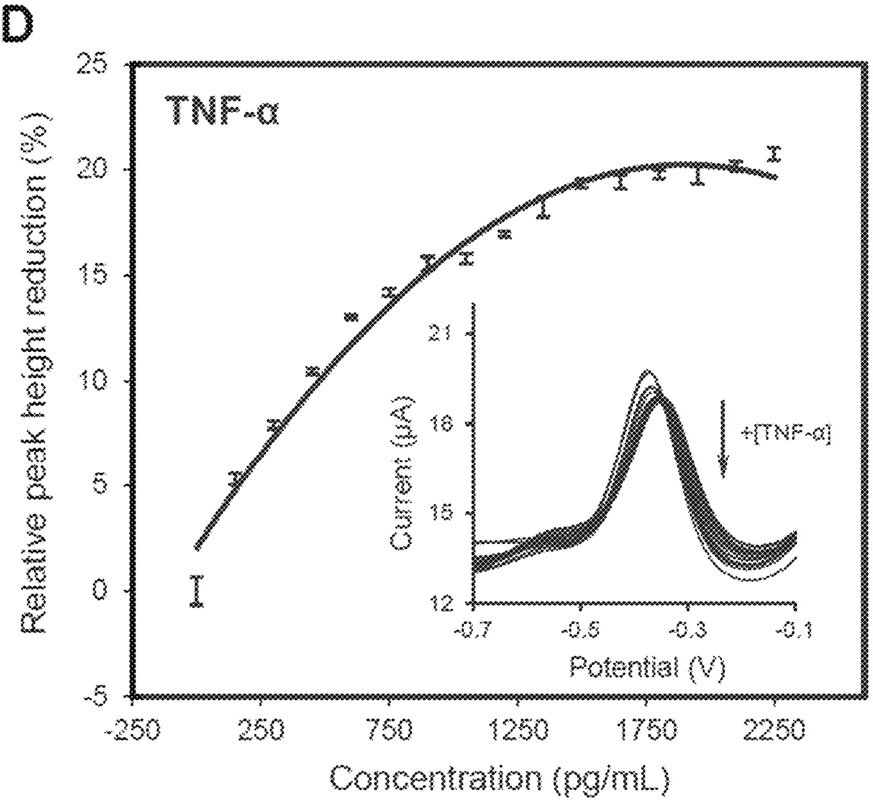
FIGS. 3D-3H show variations in relative peak height reduction of the TNF-α, TGF-β1, IL-6, IL-8, and *S. aureus* sensors versus the concentration of corresponding targets in serum, respectively. Error bars denote the standard deviation of the mean derived from three scans under same conditions. The insets show SWV scans of the TNF-α, TGF-β1, IL-6, IL-8, and *S. aureus* sensors when challenged with different analyte concentrations, respectively
Figure 3E:
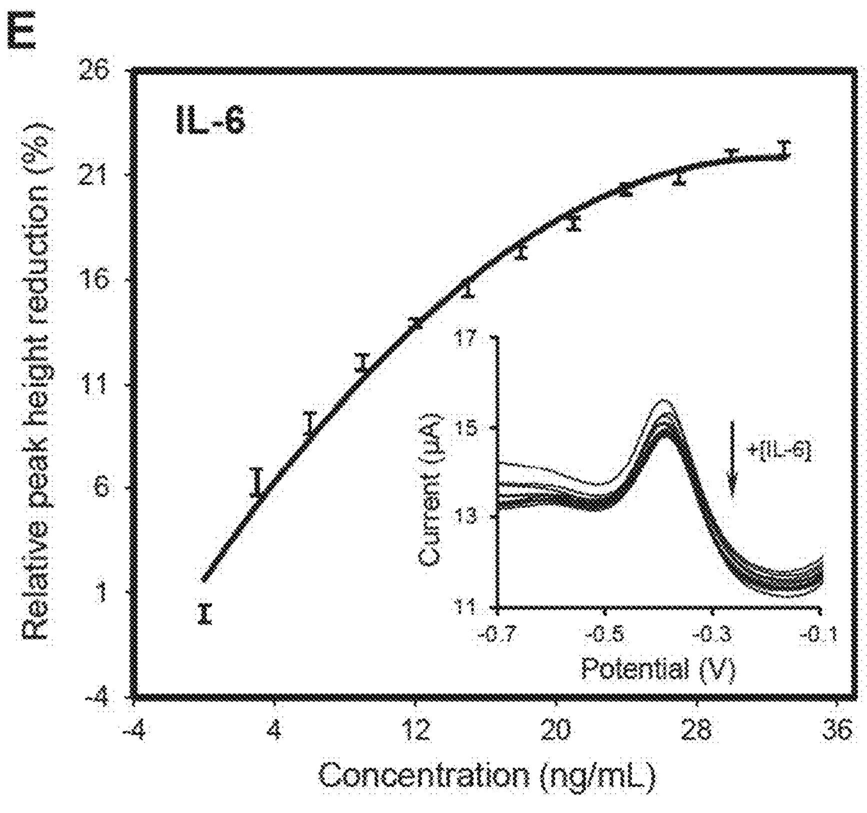
Figure 3F:
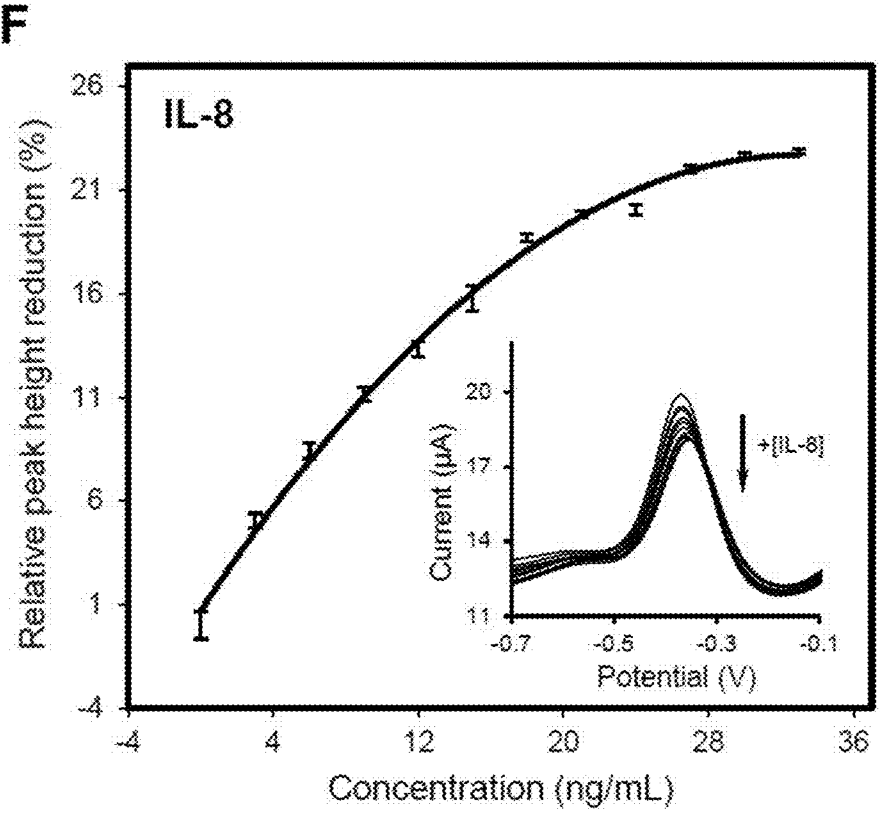
Figure 3G:
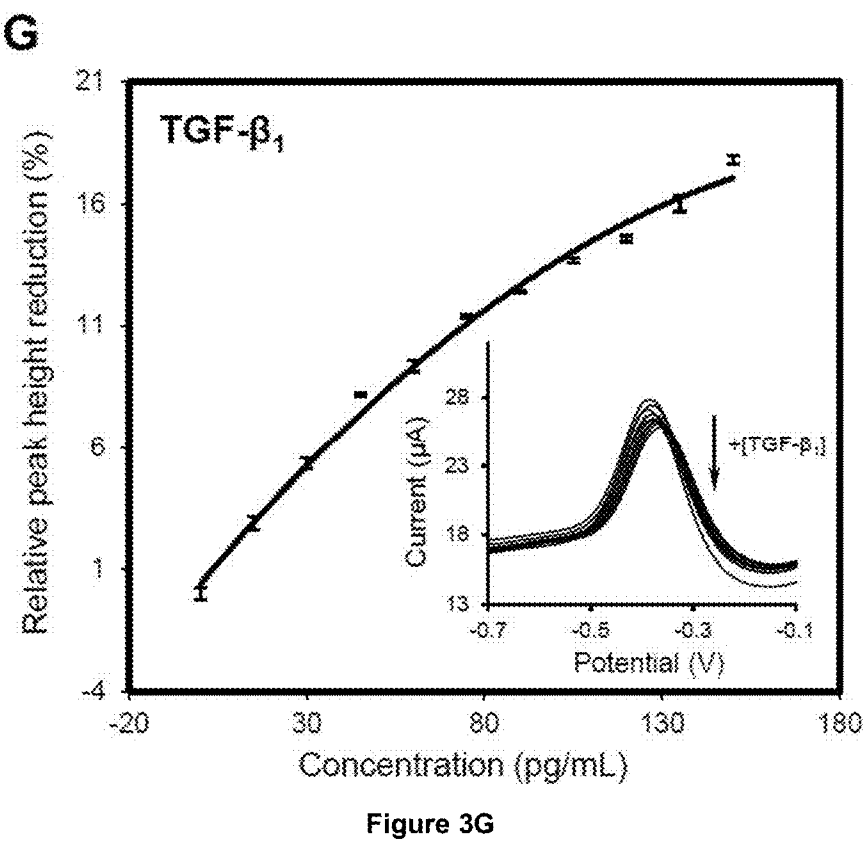
Figure 3H:
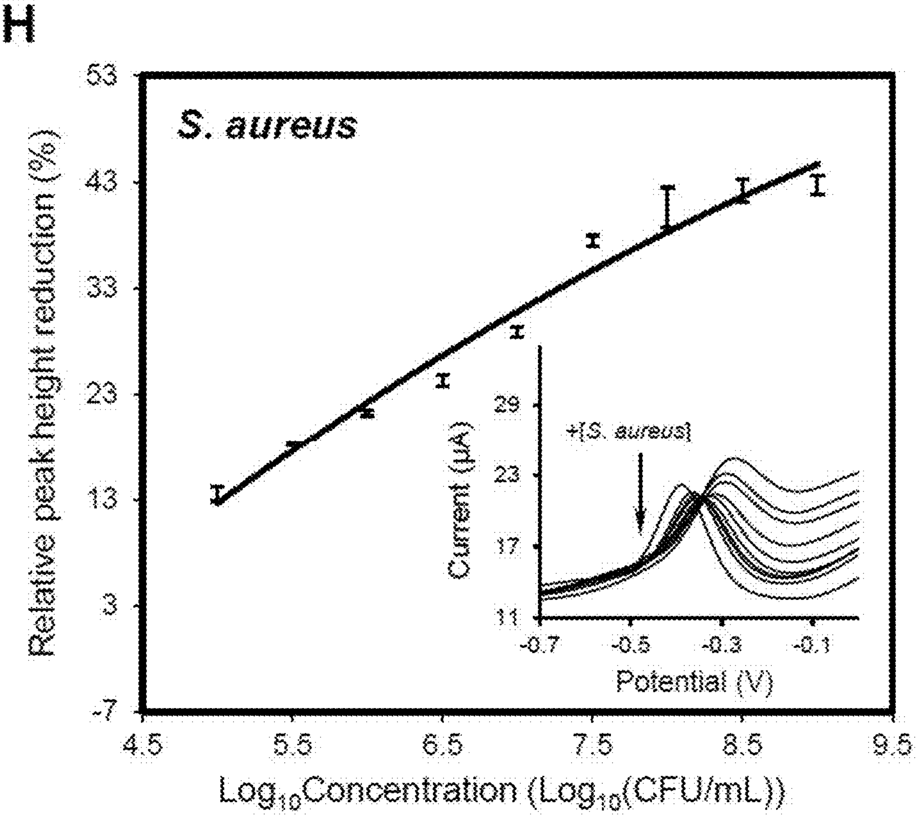
Figure 3I:
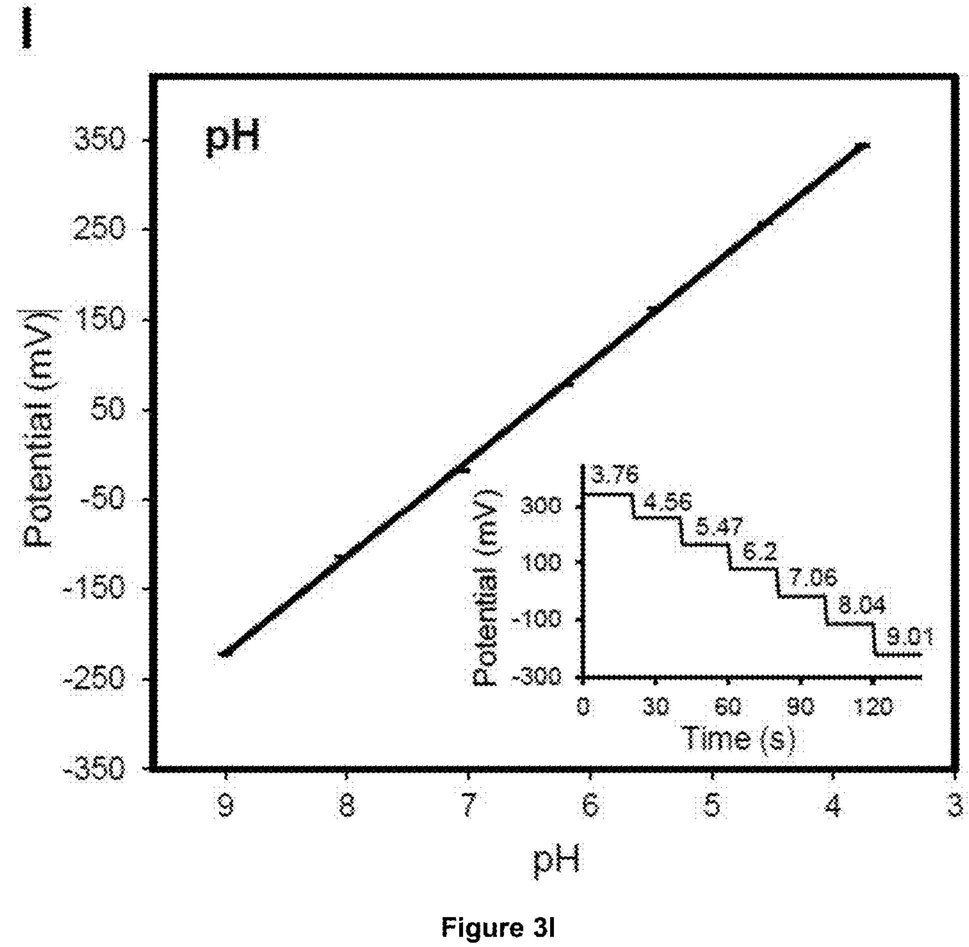
FIG. 3I shows calibration of the OCP of the pH sensor versus pH values in serum. Error bars denote the standard deviation of the mean over a 20 s span under same conditions. The inset shows the real-time OCP of the pH sensor for different pH values.
Figure 16:
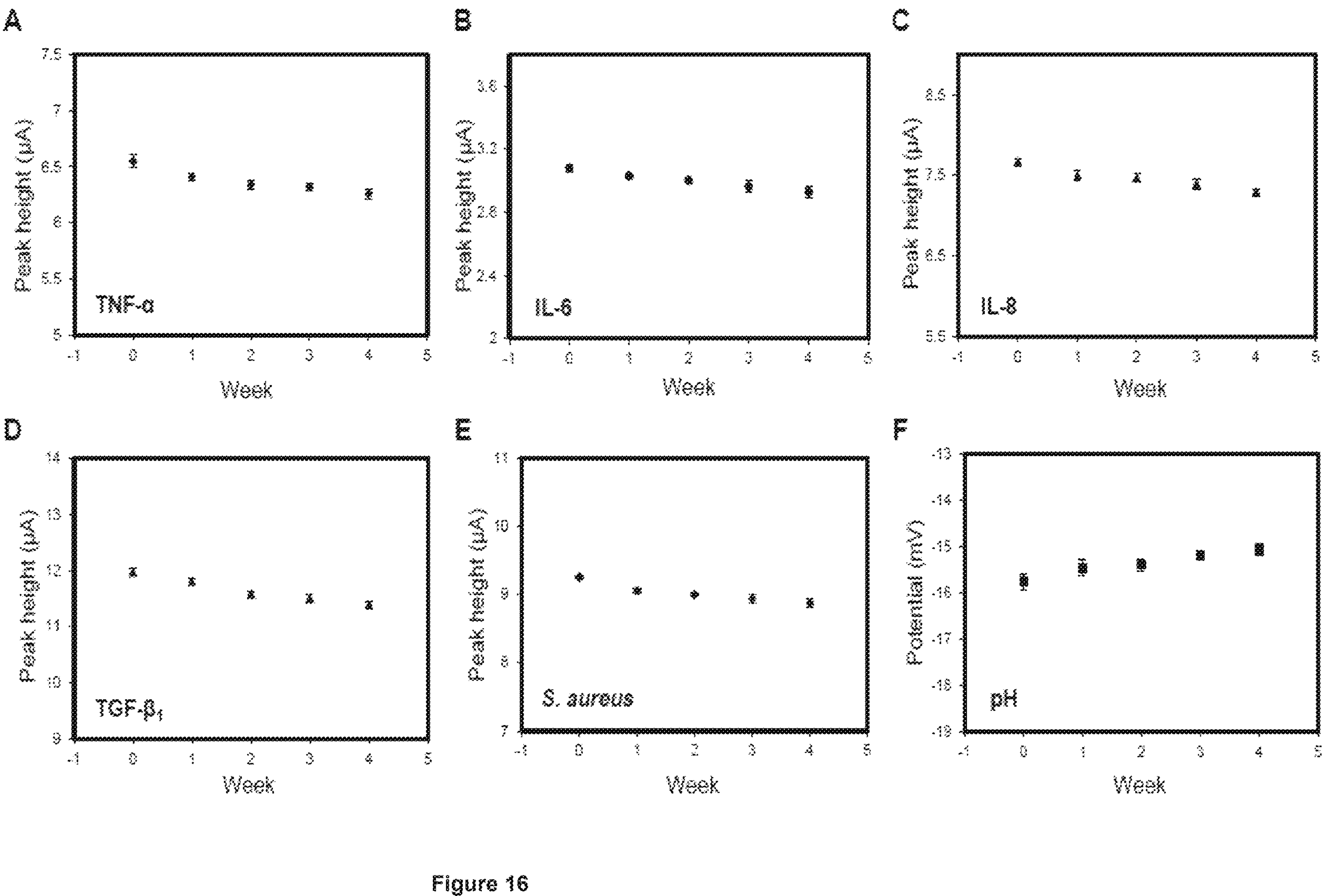
FIGS. 16A-16F show the stability of the aptamer-based sensors over a four-week period.

The working electrode for pH sensing is based on polyaniline (PANI) polymer (Methods). The open circuit potential (OCP) change was used to monitor pH variations. As shown in the inset of FIG. 3I, the potential of the pH sensor remains stable until the pH level changes. A decrease of potential was found with fluid samples changing from acid to alkaline. The characterization of the pH sensor in the serum is illustrated in FIG. 3I. The sensitivity, defined as the relative change in OCP per unit of pH values normalized to the OCP at pH 3.76, is −31.402% $[pH]^{-1}$. Having demonstrated good linearity ($R^2$=0.9997, derived from the linear regression line), the pH sensor is also characterized by good repeatability (FIG. 11A) and reproducibility (FIG. 11B). The performance of the pH sensor was also validated with plasma yielding similar results (FIG. 11C-F). The embedded temperature sensor is based on a thermally responsive resistor (Methods). The aptasensors and pH sensor showed good long-term stability over four weeks with drifts less than 5% (FIG. 16, Methods), offering the advantage over antibody based biosensors, which are easily inactivated due to antibody denaturation. The characterization of the temperature sensor is presented in FIG. 3C. The sensitivity, defined as the relative change in resistance per unit of temperature normalized to the resistance at 20° C., is 0.1384% $°C.^{-1}$ with good linearity of $R^2$=0.9998. Note that the working ranges of the pH sensor (pH 4-9) and the temperature sensor (20-50° C.) were considered to ensure coverage of the pH and temperature variations in a wound fluid environment.

Figure 12C:
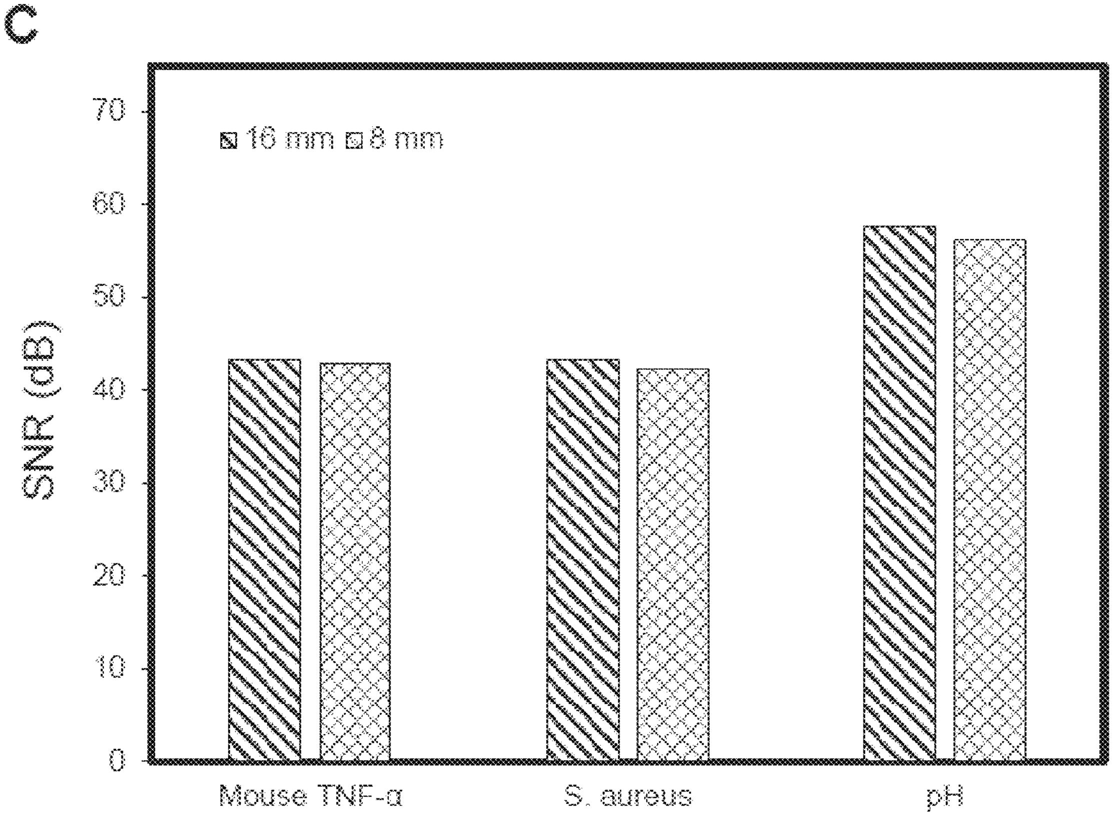

The immunosensor embedded in the biomarker analytical dressing is designed with a sensing area (diameter of 16 mm) appropriate for use with most venous ulcers. Nevertheless, the size of the immunosensor can be adjusted proportionally (FIG. 12) to fulfil a variety of other potential applications (e.g. acute trauma, surgical wounds, psoriasis, eczema). The minimum volume required for the immunosensors of different sizes is shown in FIG. 12. The limit of re-sizing was explored to be 8 mm diameter of the sensing area due to the limitation of volume a micro-well can hold for independent aptamer immobilization in the multiplexed aptasensing system. FIG. 12A shows the minimum volume required for the immunosensor under different sizes. The SNR loss when the sensor was re-sized to a smaller one (diameter of 8 mm) was observed to be less than 5% (FIG. 12C).

Methods

Micro Fabrication of Base Electrodes on Dressings

The base electrode patterns were designed using AutoCAD 2018. To fabricate the base electrodes on a dressing, a sacrificial layer of Ni (25 nm) was deposited on a Si wafer using a sputter (ATC-2200 UHV, AJA). A bottom insulation layer of SU-8 3025 (~20 μm) was spin coated on the Ni layer and patterned by photolithography. Following 02 plasma cleaning, a layer of S1818 was spin coated on the SU-8 layer and patterned by photolithography. Cr/Au (30 nm/50 nm) was deposited using a thermal evaporator (NANO 36, Kurt J. Lesker) followed by lifting up using acetone. Similarly, 200 nm Ag was deposited on the reference electrode area (diameter of 3 mm) using an E-beam evaporator (AJA). A top insulation layer of SU-8 3025 was spin coated followed by photolithography to expose the working area of the electrochemical electrodes, providing a micro-well for each working electrode. 0.1 M $FeCl_3$ solution was dropped on top of Ag for 1 min to generate the Ag/AgCl reference electrode. The microfluidic wound exudate collector was formed by spin coating a layer of SU-8 2150 (~150 μm) on top of the insulation layer and patterned by photolithography. The Ag/AgCl reference electrode was temporarily protected by a layer of 950 PMMA A4 (2 μm). The entire stack was released from the Si wafer after the Ni layer was etched by 30% $FeCl_3$ solution. Next, the PMMA layer was removed by acetone after the electrodes had been transfer-printed to a medical-grade polyurethane film (Tegaderm™). After the aptamer immobilization, the immunosensor was finally capsulated by a perforated medical-grade polyurethane film.

Micro Fabrication of Base Electrodes on PET

To fabricate the base electrodes on PET, Cr/Au (30 nm/50 nm) was directly deposited on an 02 plasma cleaned PET sheet (125 μm). The following procedures to build the stacked up layers (SU-8 insulation layer, Ag/AgCl reference electrode, microfluidic wound exudate collector) remain the same as above.

Preparation & Characterization of the AuNPs-GP Nanocomposite

The graphene flakes were firstly prepared via cathodic exfoliation. Briefly, the electrochemical exfoliation of bulk graphite was performed using an electrochemical workstation (CHI 760E) consisting of a two-electrode system. Bulk graphite crystals were placed as the working cathode, and a Pt wire was used as the counter electrode. A nonaqueous solution consisting of 0.01 M TAA salt and NMP was used as the electrolyte. The expansion of bulk graphite was achieved using a cathodic voltage of 8 V. The expanded graphene flakes were further exfoliated and isolated using centrifugation and dried. The dried graphene flakes were dispersed in DMF (1.4 mg $mL^{-1}$) followed by ultrasonication for 3 h using an ultrasonic cleaner (SW1, Sonoswiss AG). Excessive AuNPs dispersion was added into the graphene dispersion followed by sonication of 1.5 h to create well adsorption between graphene and AuNPs. The dispersion further underwent a centrifuge (Heraeus™ Pico™ 17, Thermo Scientific) at 13000 rpm for 5 min followed by washing with DMF. This step was repeated for several times to remove the unadsorbed AuNPs. The dispersion was finally sonicated for 5 min to obtain the AuNPs-GP nanocomposite. The composite is stored at 4° C. when not in use and was sonicated for 5 min before each use. The morphology images of the AuNPs-GP were acquired using a FESEM (Verios 460, FEI). The Raman spectra was measured using a Raman microscope (Alpha 300R, Witec).

Aptamer Sequences

The TNF-α aptamer sequence is: 5'-/5MeBIN/rG*rG*rA*rG*rU*rA*rU*rC*rU*rG*rA*rU*rG*rA*rC*rA*rA*rU*rU*rC*rG*rG*rA*rG*rC*rU*rC*rC/3ThioMC3-D/-3'. Specifically, the RNA oligo was modified with a disulfide (S—S) bond at the 3' terminus through a 3-carbon ($C_3$) spacer, and methylene blue (MB) at the 5' terminus through an amino modifier. Phosphorothioate bonds (marked with *) were introduced to inhibit RNA from RNase degradation.

The IL-6 aptamer sequence is: 5'-/5ThioMC6-D/GGTGGCAGGAGGACTATTTATTTGCTTTTCT/3MeBIN/-3'. Specifically, the DNA oligo was modified with a S—S bond at the 5' terminus through a 6-carbon ($C_6$) spacer, and MB at the 3' terminus through an amino modifier.

The IL-8 aptamer sequence is: 5'-/5ThioMC6-D/rGrGrGrGrGrCrUrUrArUrCrArUrUrCrCrArUrUrUrArGrUrGrUrUrArUrGrArUr ArArCrC/3MeBIN/-3'. Specifically, the RNA oligo was modified with a S—S bond at the 5' terminus through a C6 spacer, and MB at the 3' terminus through an amino modifier.

The TGF-β1 aptamer sequence is: 5'-/5MeBIN/CG*CTCGG*CTTC*ACG*AG*ATT*CGTGT*CGTTGTGT*C*CTGT*A*C*C*CG*C*CTTG*A*C*C*AGT*C*ACT*CT*AG*AGC*AT*C*CGG*A*CTG/iSpC3/3ThioMC3-D/-3'. Specifically, the DNA oligo was modified with a S—S bond at the 3' terminus through a C3 spacer, and MB at the 5' terminus through an amino modifier. An internal spacer C3 was incorporated to lengthen the spacer arm. Phosphorothioate bonds were introduced to inhibit DNA from DNase degradation.

The *S. aureus* aptamer sequence is: 5'-/5ThioMC6-D/TCGGCACGTTCTCAGTAGCGCTCGCTGGTCATCCCACAGCTACGTC/3 MeBIN/-3'. Specifically, the DNA oligo was modified with a S—S bond at the 5' terminus through a C6 spacer, and MB at the 3' terminus through an amino modifier.

The mouse TNF-α aptamer sequence is: 5'-/5ThioMC6-D/GCGCCACTACAGGGGAGCTGCCATTCGAATAGGTGGGCCGC/3MeBIN/-3'. Specifically, the DNA oligo was modified with a S—S bond at the 5' terminus through a C6 spacer, and MB at the 3' terminus through an amino modifier.

Preparation of the pH Sensor

The base electrodes were firstly cleaned with acetone and ethanol using the ultrasonic cleaner, respectively. To electropolymerize the PANI layer, 0.1 M aniline/0.1 M HCl solution was dropped on the entire electrochemical operation area, followed by CV from −0.2 V to 1 V for 25 cycles at 100 mV $s^{-1}$ using a potentiostat (CompactStat.h, Ivium, hereinafter the same).

Preparation of the Aptasensors

Following the pH sensor preparation, the electrodes were firstly rinsed with copious sterilized ultrapure (Milli-Q®) water (hereinafter referred to as 'ultrapure water') and dried under N2. Then AuNPs-GP dispersion was drop-casted onto each working electrode and dried. The AuNPs-GP modified working electrodes were rinsed with copious ultrapure water, followed by a second wash with DNase/RNase-free distilled water (hereinafter referred to as 'distilled water'). 100 μM oligos was reduced by 10 mM TCEP at room temperature for 1 h to cleave the S—S bond. Consecutively, the oligos were then diluted to 10 μM using IDTE buffer and vortexed for 10 s to help disperse. 10 μM TNF-α, IL-6, IL-8, TGF-β1, and *S. aureus* aptamer dispersion was dropped onto each working electrode respectively and incubated airtightly at room temperature for 6 h. The aptamer immobilized electrodes were subsequently rinsed with copious ultrapure water, followed by a second wash with distilled water. 3 mM MCH was dropped onto each working electrode and incubated airtightly at room temperature overnight. Finally, after being rinsed with copious ultrapure water, followed by a second wash with distilled water, the aptasensors were ready for use.

Qualitative Analysis & Characterization of the Aptamer Sensors

The qualitative assessment of aptasensors was conducted in 5 mM $K_3Fe(CN)_6/K_4Fe(CN)_6$ (1:1) containing 0.1 M KCl dropped on the entire electrochemical operation area. For CV measurement, the potential range is from −0.6 V to 0.6 Vat different scan rates (150-10 mV $s^{-1}$) for the quasi-reversibility analysis of the AuNPs-GP modified electrode, while the scan rate is fixed at 50 mV $s^{-1}$ for the stepwise assembly analysis. For EIS measurement, the applied potential is 0.2 V. Voltage frequencies range from 100 kHz to 0.01 Hz with an amplitude of 5 mV. The Randles circuit was used to fit the Nyquist plots. The cytokine sensors were characterized in human serum with spiked analytes (reconstituted in PBS). Bacteria culture and enumeration were conducted prior to the characterization of *S. aureus*. Briefly, a *S. aureus* colony from a streak plate was inoculated into 10 mL sterilized LB broth (hereinafter referred to as 'LB broth') and allowed to grow at 37° C. for 17 h at 200 rpm. 1 mL of the inoculum and its serial diluent were respectively mixed with 15 mL sterilized TSA medium for pour plate culture. After incubation, the plate with visible isolated colonies showing between 30-300 was used to estimate the *S. aureus* cell density in the original inoculum. Subsequently, *S. aureus* was pelleted after being centrifuged at 4000 rpm for 5 min and reconstituted in human serum for sensor characterization. The SWV measurement for aptasensors was scanned from −0.8 V to 0 V with a step potential of 4 mV. The frequency is 50 Hz with a pulse amplitude of 40 mV. In addition, the solutions with pH values of 3.76, 4.56, 5.47, 6.2, 7.06 and 8.04 used for pH sensor characterization were prepared by a mixture of serum and McIlvaine buffer, while the solution with pH 9.01 was obtained by a mixture of serum and pH 10.00 buffer. The temperature sensor was characterized in a glass beaker contained with water whose temperature was tuned by a hotplate underneath the beaker.

The long-term stability of the aptasensors or pH sensor was studied by observing the longitudinal weekly variations of the peak height against no analyte or OCP at pH 7.06 for four consecutive weeks. The immunosensor was stored airtight and at 4° C. in between each measurement.

Wireless Electrochemical Analyzer

Drawing inspiration from the open-source Universal Wireless Electrochemical Detector (UWED), a wireless electrochemical analyzer was designed and fabricated to carry out comprehensive chronic wound monitoring. Unlike the UWED which was designed to operate on a single channel with a commercial three-electrode cell, the device is a multi-channel design, capable of performing multiple analysis techniques with the 10-electrode sensor.

Hardware Design

The main components include the digital-to-analog converter (DAC), low-pass filter, potentiostat, analog switches, multiplexer, temperature sensing circuit, and lastly the microcontroller RFduino. The hardware was made to interface with the immunosensor described in previous sections. Using Autodesk Eagle 9.3.0, the circuit schematics were first designed. Subsequently, the component layouts and wires for the two-layer PCB prototype and the FPCB were designed. Both designs were fabricated and partially assembled using a turnkey PCB service (Interhorizon Corporation Pte. Ltd., Singapore). The PCBs were inspected with a microscope and a multimeter to ensure correct connections between all the components.

Microcontroller, DAC, Filter and Potentiostat

The microcontroller, DAC, filter and potentiostat were adopted from the UWED. The core of the device uses the microcontroller RFduino, which is a low-cost 32-bit ARM processor. The RFduino chip package incorporates many GPIO ports and an I2C bus for interfacing with peripheral components, as well as an on-board 10-bit analog-to-digital converter (ADC) for the sampling of measurement data. Furthermore, it is compatible with the Arduino developing environment and has an integrated BLE front-end to communicate with a BLE-enabled mobile device such as a phone or tablet. The DAC receives digital voltage input from the microcontroller via the I2C protocol and outputs analogue voltage to the WE and RE through 2 separate channels. A second order low-pass filter using operational amplifiers (op-amp) was included to minimize electrical noise in the RE potential. WE potentials are set directly from the second output of the DAC.

Analog Switches and Multiplexer

To achieve multi-technique and multi-channel operations, analog switches and a multiplexer integrated circuit (IC) component were utilised (Analog Devices Inc. triple 3-to-1 multiplexer IC, ADG793G) to realize the necessary hardware logic, controllable using general purpose input-output (GPIO) and 120 protocol, respectively. The analog switches are important to enable switching between different techniques. To support both amperometric (SWV) and potentiometric (OCP) measurements, a set of 2 switches (S1 and S2, FIG. 1D) was used to alternate the op-amp OP2 between a transimpedance amplifier and a voltage follower configuration. Additional switches are used to realize the necessary hardware logic to support switching between OCP, SWV and temperature measurement, while the multiplexer IC allows for a programmable selection of each WE channel.

Temperature Sensing Circuit

The temperature sensing circuit was designed based on the Wheatstone bridge differential amplifier configuration, which enables accurate measurement of resistance. The Wheatstone bridge makes use of two voltage divider paths to establish a balancing point, at which a small deviation in the resistance of the thermistor would produce a differential voltage at the output of the op amp. Since the thermistor resistance varies between 2.3 kΩ and 2.5 kΩ within the temperature range of interest, the balancing resistor was chosen to be 2.26 kΩ, and the instrumentation amplifier AD627ARZ configured to a gain of 25 was used.

Custom MATLAB Application

A mobile application was developed using MATLAB 2018b to accompany the layered dressing (VeCare), providing a GUI as well as comprehensive data processing and reporting. It can be run on any personal computer or mobile tablet that supports MATLAB 2018b, with the help of a BLE-to-USB adaptor. The application was designed as a one-stop patient management, data recording, data analysis and result visualization system, intended for use by the healthcare provider. Upon turning on the VeCare, a BLE connection was established to the application using Universally Unique Identifiers (UUID). Thereafter, the healthcare provider can use the application to manage patient profiles, collect sensor data, obtain visual feedback from the GUI in real-time, analyze the data and generate useful results, as well as record them to the respective profiles for monitoring over an extended time period.

Power Source

The hardware may be powered by a single rechargeable 3.7 V Lithium-ion polymer battery with the desired capacity. In our implementation, a battery pack of 190 mAh capacity was used, which provided an estimated 40 hours of continuous active operation. Being a point-of-care diagnostic device, the actual battery life may be significantly longer, depending on how often it needs to be active. Low-dropout regulator ICs (MICREL MIC5205-3.3YM5) were used to produce separate 3.3 V digital and analog power supplies, respectively serving the RFduino microcontroller and the analog peripheral components, creating separate digital and analog circuitry to prevent digital noise from degrading analog performance.

Example 2: In Situ Wound Monitoring & Biocompatibility Study in Mice Models

Results

Figure 4D:
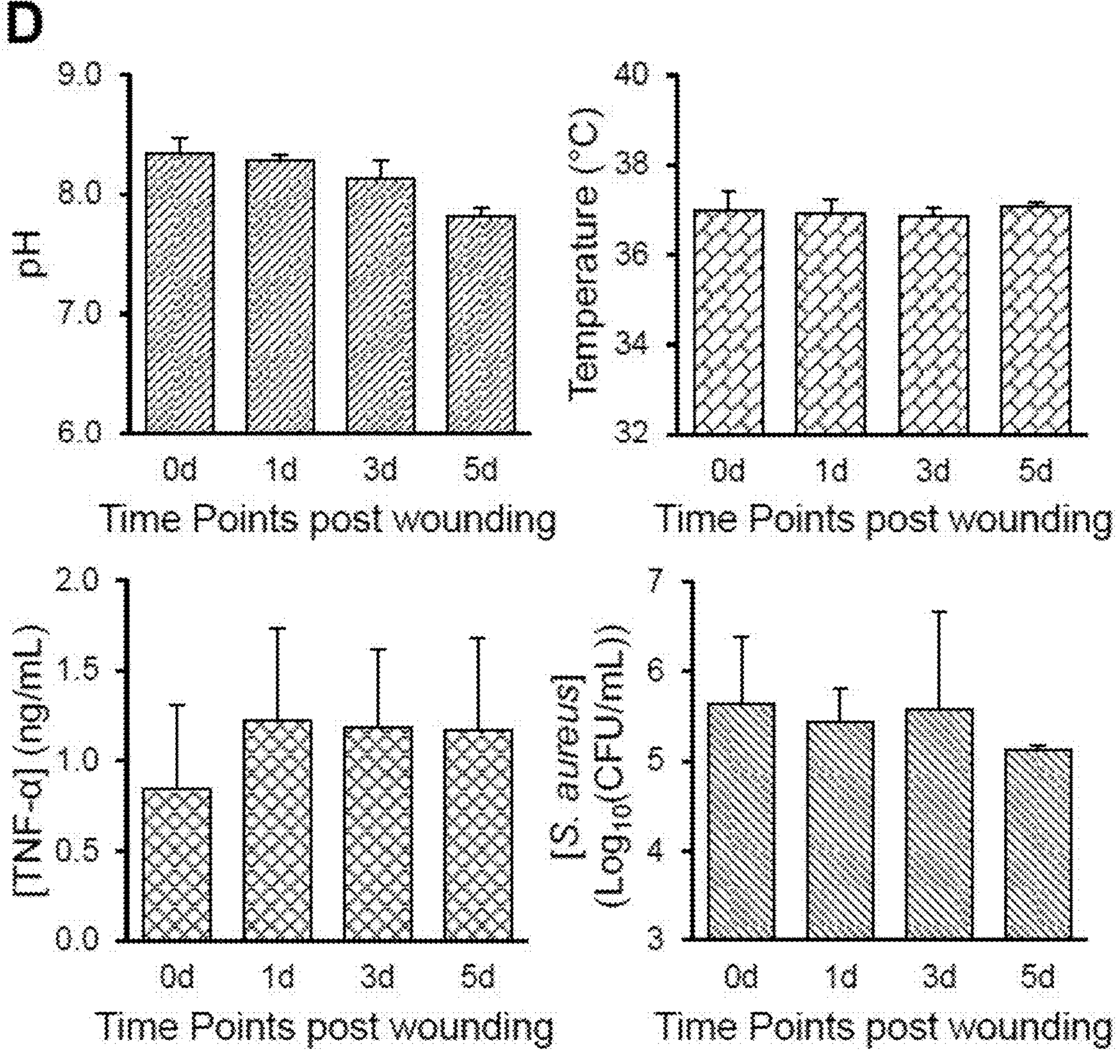
FIG. 4D shows in situ assessment of pH, temperature, mouse TNF-α, and *S. aureus* by the immunosensor. Error bars show standard deviation.

To demonstrate the utility of the platform for in situ wound monitoring, longitudinal wound monitoring was performed in mice models (Methods). Briefly, two bilateral full-thickness excisional wounds were made on Day 0, equidistant from the midline and spaced on either side of the dorsum (FIG. 4A). An immunosensor was in direct contact with the right wound (FIG. 4C), while the left wound was used as control. Subjects were allowed to freely move for 1 hour with the attached immunosensor, followed by in situ wound monitoring. The presence of the immunosensor appeared to be well-tolerated, with no observed signs of discomfort during freely-moving behaviour or any excessive scratching of the sensor-covered wound (FIG. 4B). In all cases, the immunosensor remained functional after 1-hour contact with the wound. FIG. 4D illustrates the longitudinal assessment of pH, temperature, mouse TNF-α, and *S. aureus* at time of wounding (Day 0 (N=9)) as well as at Day 1 (N=9), Day 3 (N=6) and Day 5 (N=3) post-wounding. Longitudinal pH measurements show that the pH at the wound site decreases by 6% on Day 5 compared to Day 0. This decrease corresponded with reepithelization of the wound, which is associated with hypoxia and lactic acid production. The immunosensor measurement also revealed a significant increase (give 44% increase) in TNF-α from Day 0 to Day 1 corresponding to the inflammatory response after wounding. In contrast, the temperature and level of *S. aureus* measured at the wound were constant throughout the healing duration, which is consistent with the absence of infection as assessed by visual inspection. These results demonstrated that the immunosensor allows for in situ multi-biomarker profiling of wound fluid over the duration relevant to wound healing.

Histological examination of the wound site further demonstrate the biocompatibility of the immunosensor. No apparent signs of adverse reactions (e.g., redness, swelling, degeneration) were observed on the skin surface that was in contact with the immunosensor over 5 days (FIG. 4E). FIG. 4F-G showed no cumulative effect of the sensor placement on the rate of wound closure. The reepithelialisation distance and nascent epidermal thickness were measured from hematoxylin and eosin (H&E) tissue section images (FIG. 4H, 4I) to assess the effect of sensor placement on wound healing. No significant difference was observed between control wounds and wounds that had sensor contact (FIG. 4J, 4K). Qualitative assessment of the immune cells in the dermis at the wound edge, identified by cell morphology and polymorphonuclear presence, suggested no difference in infiltration at all time points of sensor contact (FIG. 4L, 4M). FIG. 4N revealed no difference in granulation tissue maturation or levels of cellularity. The behavioural, visual and histological assessment in the wound healing mice models demonstrated the biocompatibility of the immunosensor for in situ wound surveillance.

Methods

Characterization of the Mouse TNF-α Sensor

The aptasensor showed decreasing peak current height with the increase of target concentration (FIG. 14 part a). The relative reduction of peak height normalized to peak height against no analyte with analyte concentration is exhibited in FIG. 14 part b. Notably, the concentration range of mouse TNF-α (0-1800 μg $mL^{-1}$) was based upon levels reported in wound tissues from mice models.

Animal Procedures

Mice were housed in individual ventilated cages over a 12-hour light/dark cycle. They were fed a standard laboratory diet and water ad libitum. In this study male ICR outbred mice (IcrTac:ICR, provided by InVivos, Singapore) 10-12 weeks of age, 25-35 g in weight were used. Inhaled isoflurane (5% mg/kg) was used to induce anaesthesia, which was checked by testing pedal reflex. The back of the animal was prepped by shaving with electric hair trimmer, with care not to induce any trauma with razor teeth. Depilatory cream was then applied to the shaved skin for 2 min. The hair and cream were removed with warm water and gauze. Clean dry gauze was used to wipe off all remaining hair remover cream, to insure no risk of skin irritation or lesions. Animals were injected subcutaneously with Buprenorphine (1.5 mg/kg) before wounding and daily for three days post wounding and on days of sensor placement. To produce full-thickness excisional wounds, the back skin of the mice was lifted away from the dorsum and a 6 mm biopsy punch used to incise and perform the wound through the panniculus carnosus. This technique was used to produce two bilateral wounds equidistant from the midline and spaced either side of the dorsum. A clean dry gauze was used to remove any blood resulted from the surgical procedure. Only when the bleeding stopped which happened quite quickly in the mice, was the gauze removed. An immunosensor (diameter of 8 mm) was placed on either wound while the other wound used as a control. The wound with sensor contact and the control were randomly assigned. The immunosensor or the control were dressed with small individual sections of a Tegaderm™ film. A large single dressing of OPSITE (Smith and Nephew) was then used to cover the whole back. The immunosensor was left in place for 1 hour with the animals allowed to recover in their normal housing, before readings were taken under anaesthesia. An estimated volume of 5 μL wound exudate was accumulated in a flow rate up to 0.43 $mm^3$ $s^{-1}$, which was sufficient for sensor readings (FIG. 12A). Before measurement, the stabilization of the signals was confirmed when the peak height variation of three continuous scans was under 1% (noise level). The immunosensor was then removed and the dressing replaced.

Tissue Processing Sectioning and Staining

Animals were euthanized via $CO_2$ inhalation, with cervical dislocation used as a secondary means to confirm death. Animals were culled at 1, 3 and 5 days post wounding (N=3 per time point). The back skin was excised in one large piece and laid flat on a smooth card. Wounds were excised and fixed in 4% paraformaldehyde for at least 24 hours and stored at 4° C. After fixation samples were transferred to 70% (v/v) ethanol for 24 hours before processing in a HistoCore PEARL (Leica) tissue processor. Tissues are put through an ethanol concentration gradient (70%, 80%, 95%, 100%×3, 45 min, 45° C.) followed by xylene (3×45 min, 45° C.) and paraffin (3×45 min, 62° C.). Then transferred to a paraffin wax tissue embedder (HistoCore Arcadia C and H, Leica). Then 4 μm tissue sections were produced using a Leica RM2245 microtome (Leica) and attached on Polysine® slides. These were dried at 40° C. for at least an hour before staining. Hematoxylin and eosin staining was achieved using a Leica Autostainer XL (Leica). Organo mounting medium (Sigma) was used to mount slides.

Brightfield Microscopy and Image Analysis

Images of the wounds were taken daily after sensor reading or during dressing changes using a camera (Nikon D5600) with a scale and colour reference. Wound area measurements were obtained using Image J (NIH). Hematoxylin and eosin (H&E) stained tissues were imaged using an AxioScan.Z1 slide scanner with 20× objective (Zeiss). Images were qualitatively examined and exported using ZEN (Zeiss). Further quantitative analysis was performed on exported images using Image J. Epidermal thickness was measured at 150 μm back from the leading edge on both sides of each wound and values averaged for each sample. Reepithelialization distance measurement for each sample was obtained by measuring the length of nascent epidermis outgrowing from the wound edge on both sides of each wound using ImageJ and averaged. Infiltrating immune cells were qualitatively assessed by looking at polymorphonuclear cells and macrophage cells in a region of interest in the dermis at the wound edge on both sides of each wound.

Example 3: Clinical Study on Wound Exudates from Venous Ulcer Patients

Results

Figure 5A:
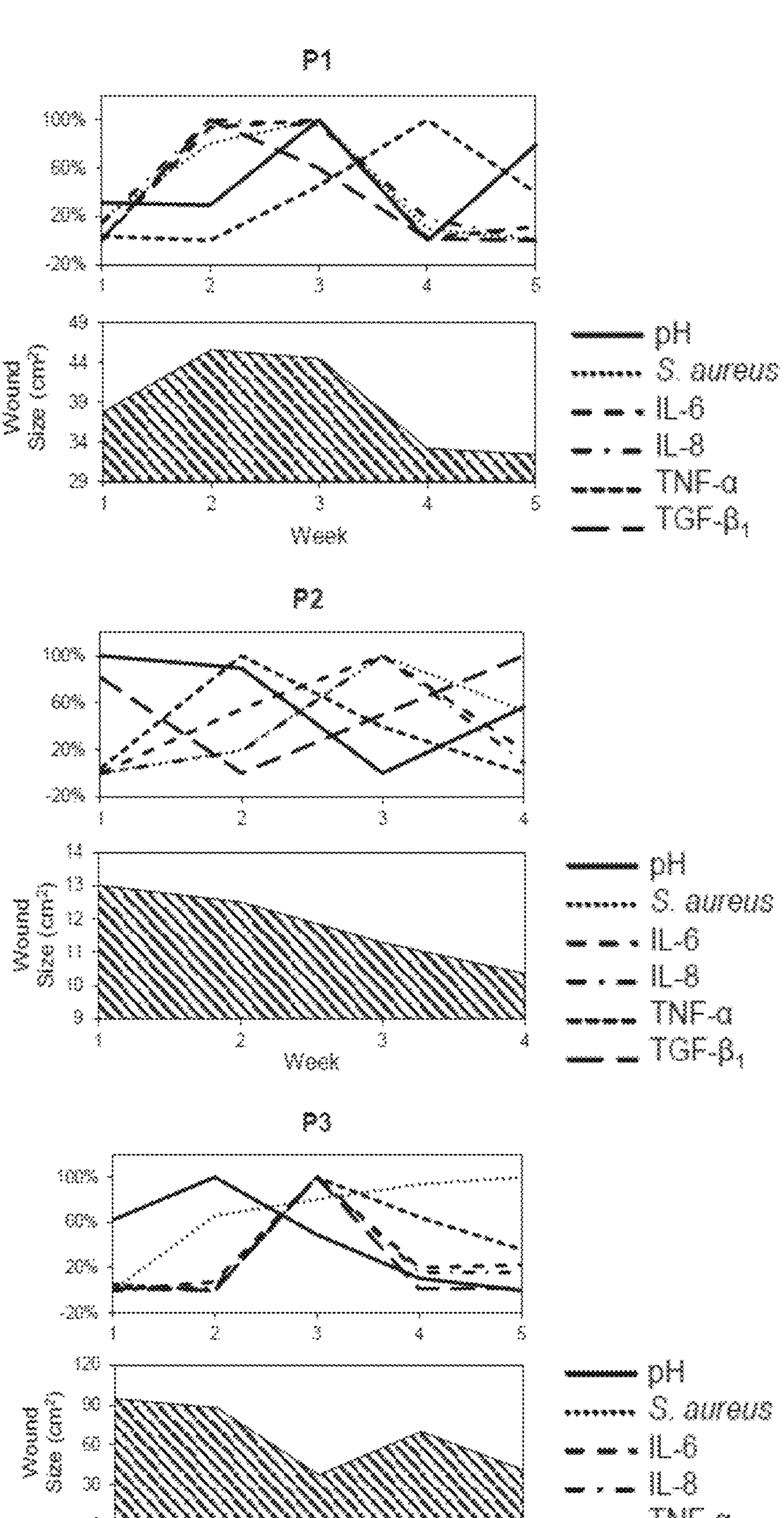
FIGS. 5Aa and 5Ab shows weekly assessment of pH, *S. aureus*, IL-6, IL-8, TNF-α, TGF-131 by the immunosensor for each patient. The axes represent independent scales for each of the quantified parameter, varying from 0% for the lowest level to 100% for the highest level. Weekly changes of the wound size are shown along with the biomarker assessment.
Figure 5A:
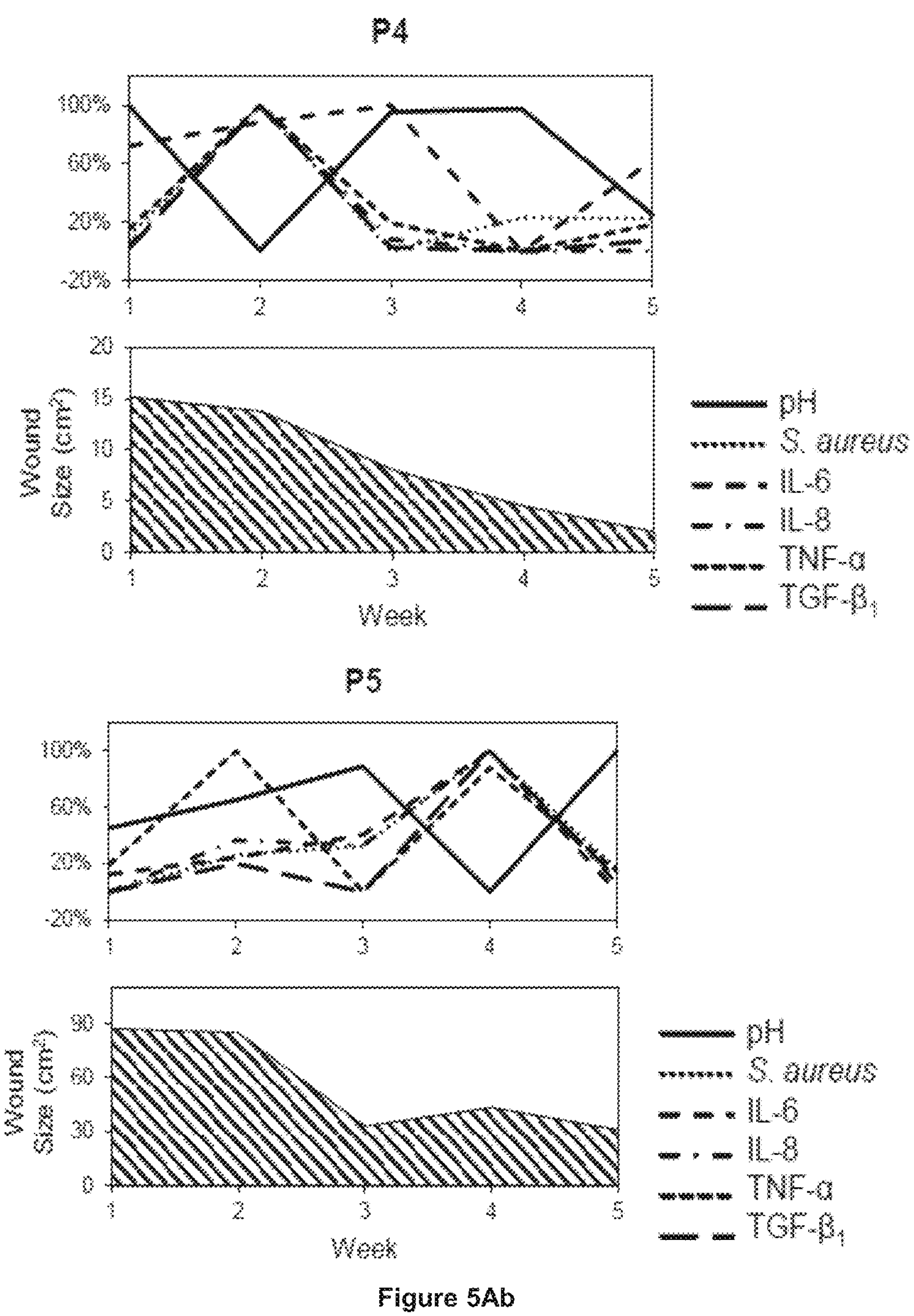

To assess the clinical application of the immunosensor, the platform was used to analyse wound exudate from venous ulcers in order to objectively observe wound bed characteristics and bioburden (Methods). Briefly, wound exudates from five patients (P1-P5) with clinically diagnosed non-healing venous ulcers were consecutively collected once a week for five weeks. The wound exudates were assessed using the platform described herein. FIGS. 5Aa and 5Ab illustrate the longitudinal changes of TNF-α, IL-6, IL-8, TGF-β1, *S. aureus*, pH and wound sizes. It is clear that the readings for each biomarker varied over the period of study. While each patient's wound fluids exhibited individually unique longitudinal profiles, some common features were evident. For example, wound fluids in P2 and P3 became less alkaline during week 1-3 and week 2-5, respectively, suggesting their wounds were positively responding to the therapies for those periods. P2 (week 3), P4 (week 2) and P5 (week 4) experienced elevated load of *S. aureus* and exhibited more alkali wound fluids in their subsequent week of visit. These observations were consistent with the reported associations between wound infection and pH. P2 who exhibited high levels of *S. aureus*; had corresponding elevated levels of IL-6 and IL-8 at week 3.

To assess the effect of wound exudates on the sensor performance, analytes with different high concentrations or pH values were used to challenge the immunosensor after use. FIG. 17A-E show the performance of each aptasensors, respectively. The peak current height of each aptasensor was observed to further decrease with increased target concentration, as shown in the insets of FIG. 17A-E, respectively. FIG. 17F exhibits consistent performance of the pH sensor with a newly prepared one. The performance of the immunosensor was shown not to be compromised after exposure to the wound exudates.

Figure 13A:
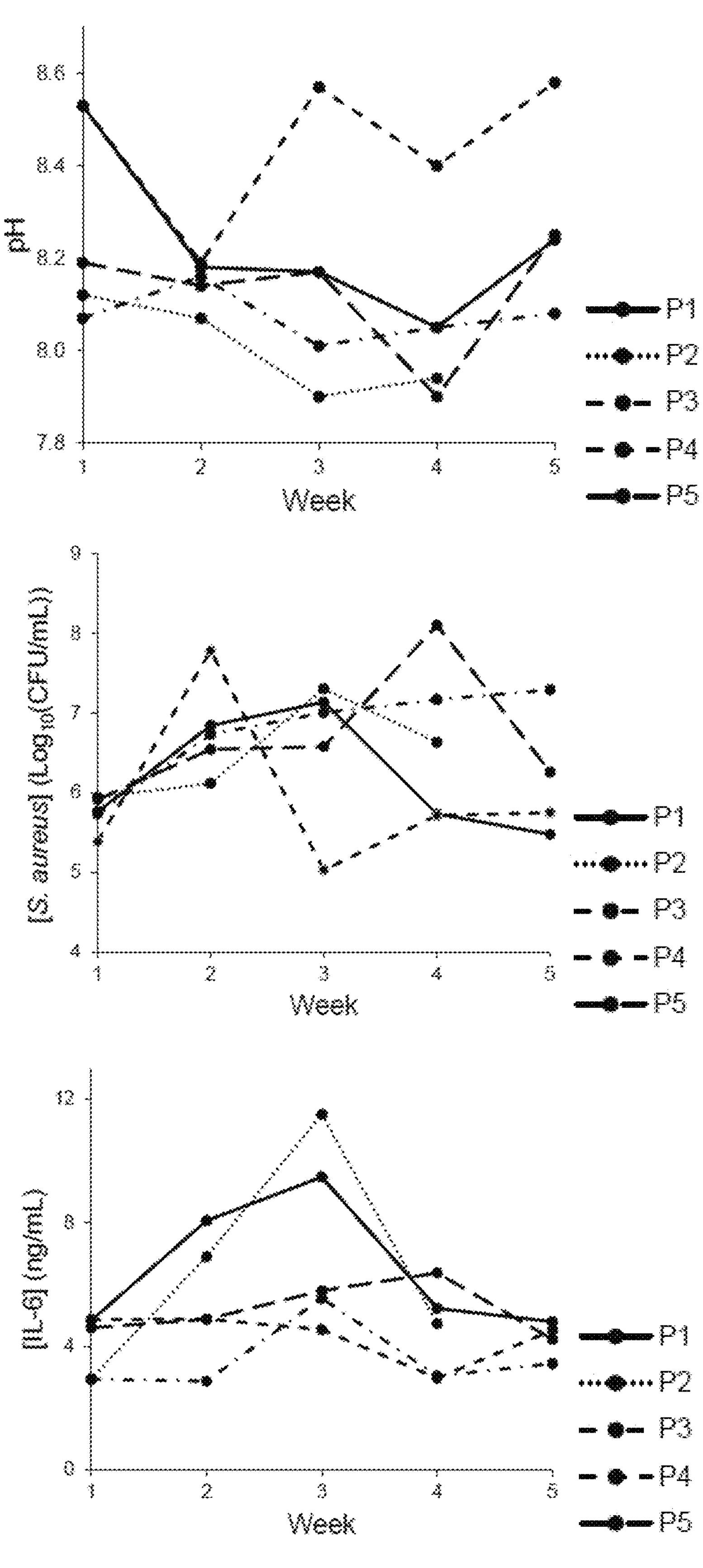
FIGS. 13A and 13B show weekly changes in the levels of pH, *S. aureus*, IL-6, IL-8, TNF-α and TGF-β1 from conventional assays.
Figure 13B:
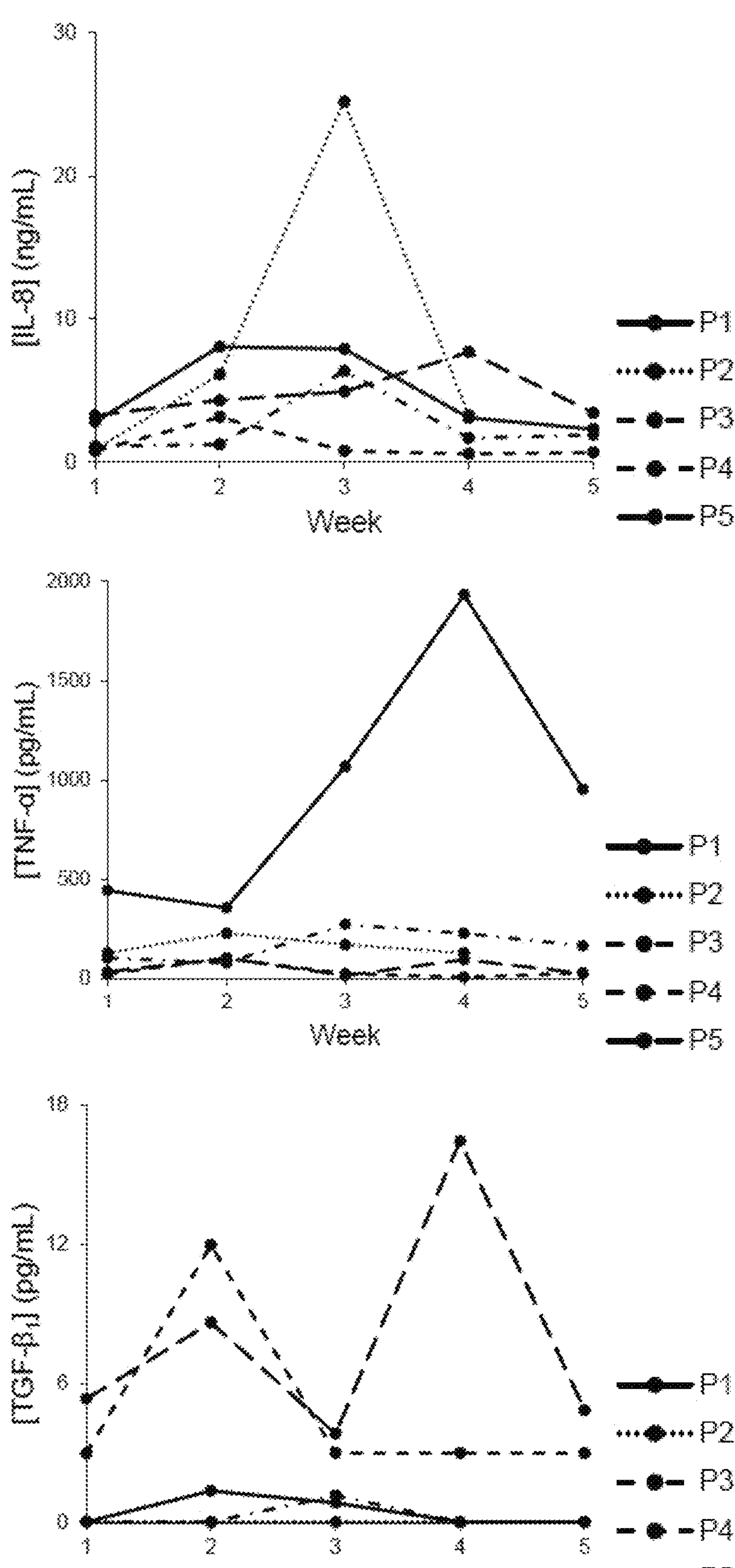
Figure 15A:
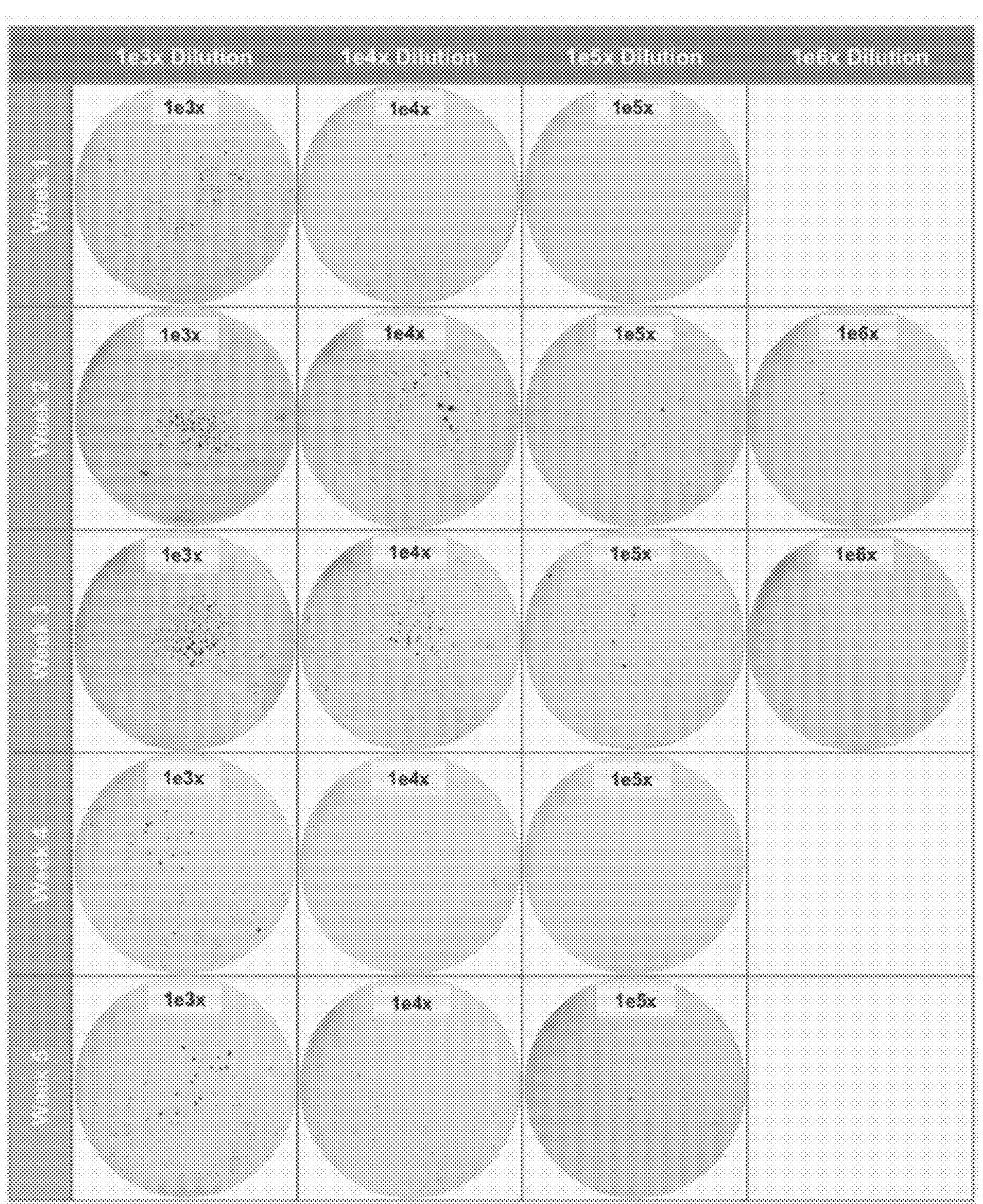
FIGS. 15A-15E show optical images of RAPID'Staph agar plates for *S. aureus* cell density estimation in the wound exudate sample of patients 1-5, respectively, over five consecutive weeks.
Figure 15B:
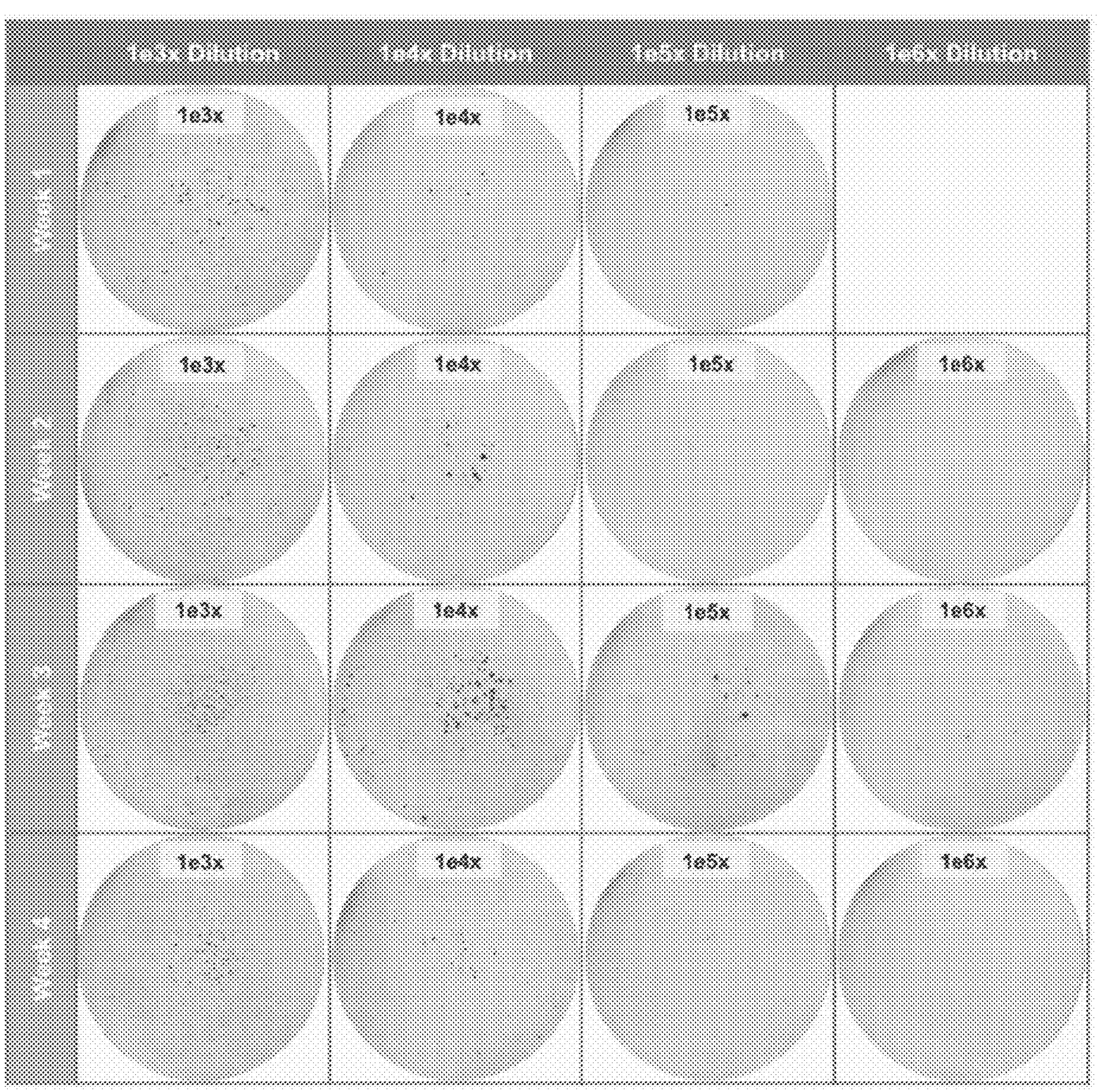
Figure 15C:
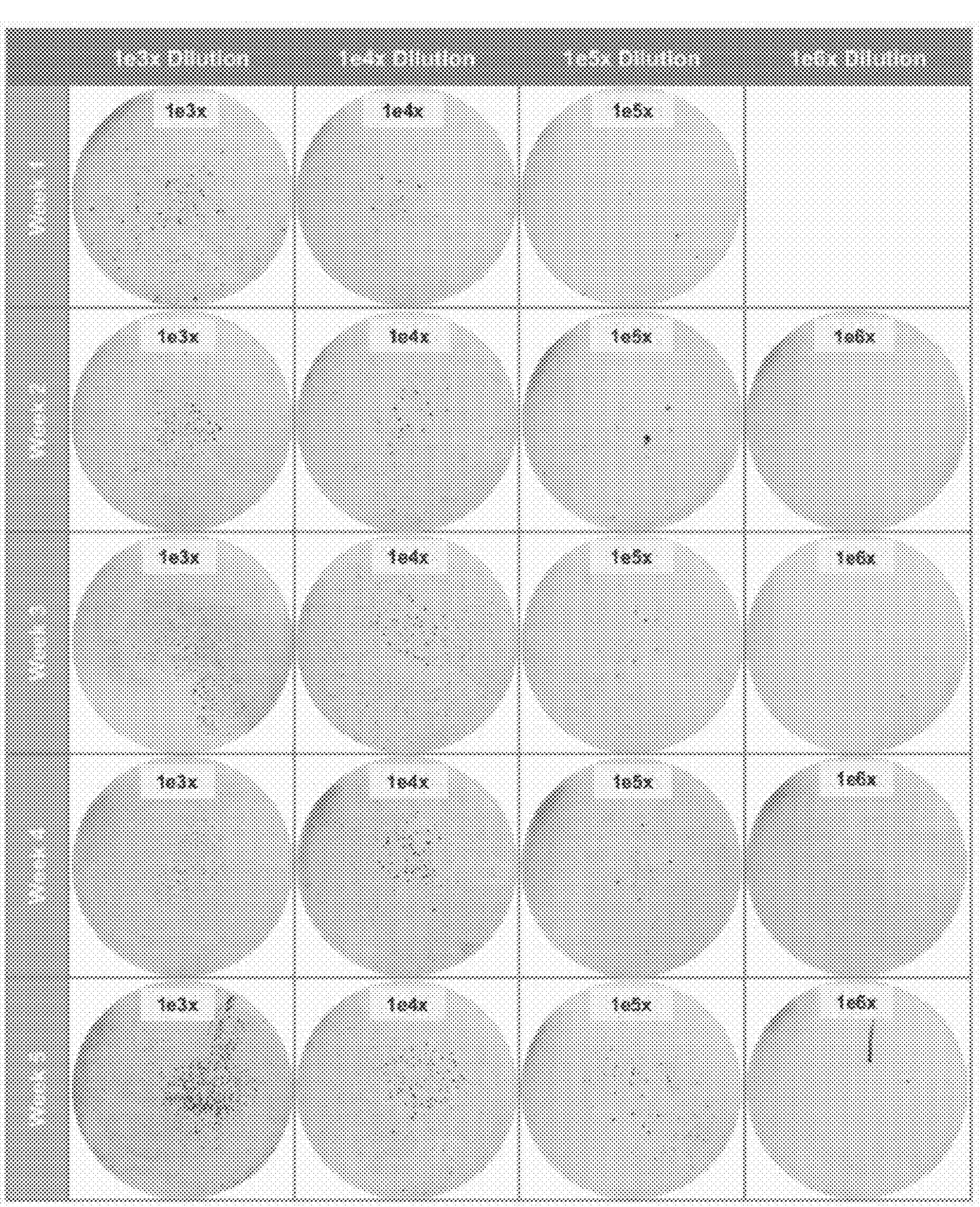
Figure 15D:
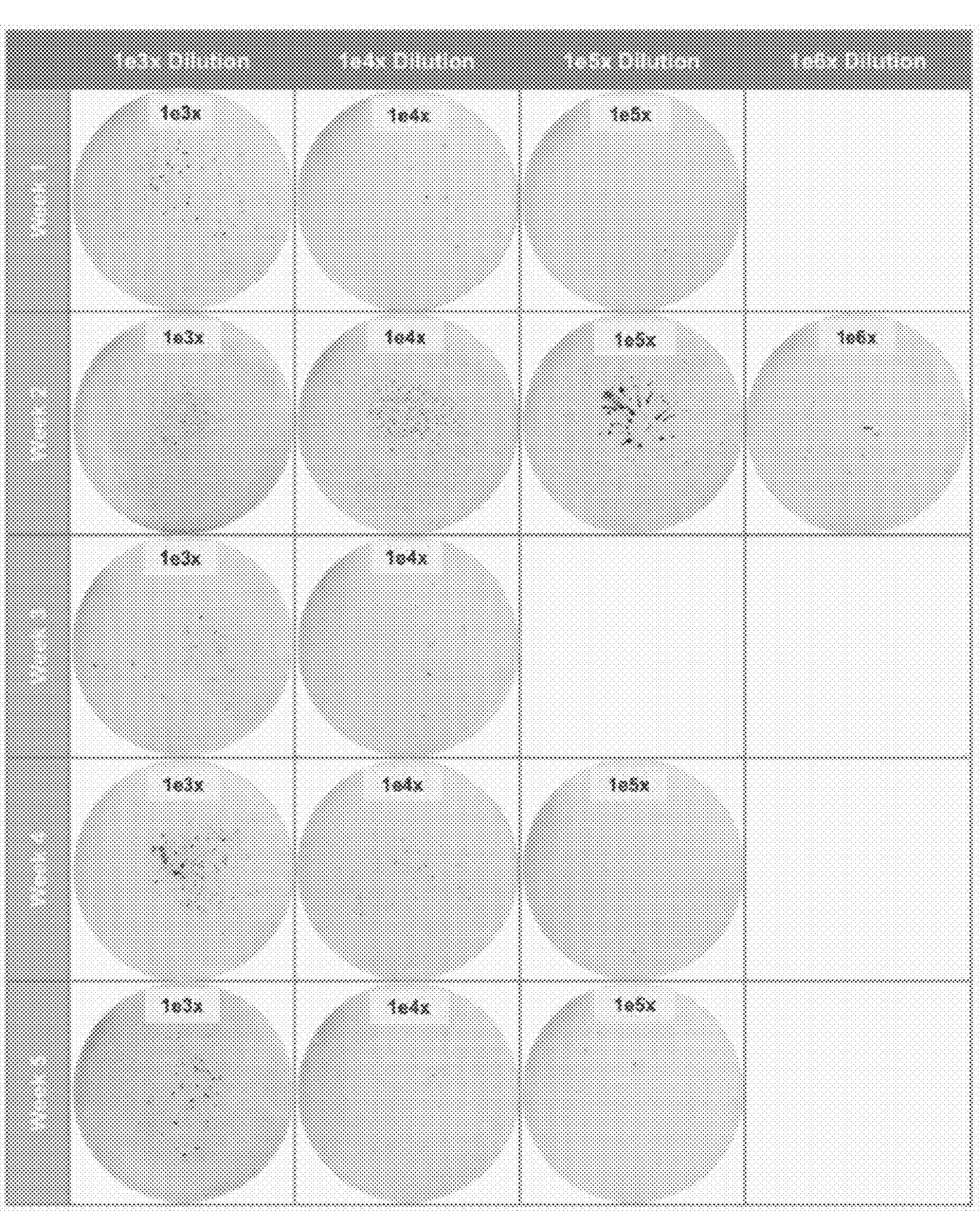
Figure 15E:
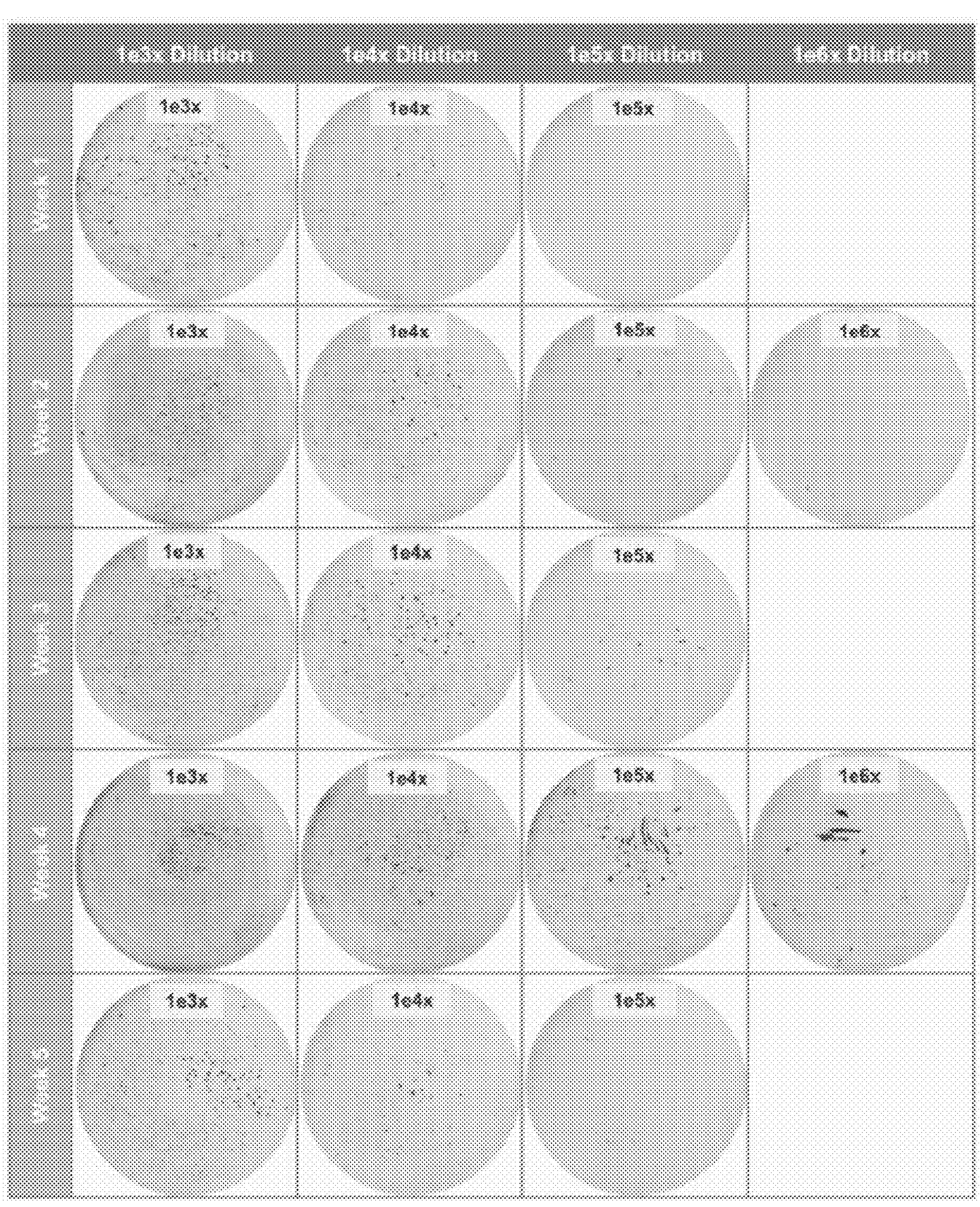

Similar responses were observed in P1 (week 3), P3 (week 3), P4 (week 2) and P5 (week 4) with elevated *S. aureus*, IL-6, IL-8 and TNF-α levels, consistent with the observations in keratinocytes. P1 (week 2) and P5 (week 4) who showed an increase of wound size were observed to have elevated levels of IL-6 and IL-8, consistent with the observations in a pilot study of 10 refractory venous ulcers. Apart from this, the inflammation and colonization tendencies in P1 (week 3), P2 (week 3), P4 (week 2) and P5 (week 4) were reduced in the following week, indicating that the clinical interventions (e.g., topical dressings impregnated with antiseptic) seem to be effective at reducing microorganism loads. These multi-biomarker profiles can provide comprehensive wound-specific parameters and inform clinical decisions on modality and duration of treatment. The biomarkers, as measured by the immunosensor, were further independently assessed using conventional approaches. The levels of cytokines, pH and *S. aureus* were determined using multiplex ELISA, pH meter, and coagulase-positive Staphylococci enumeration, respectively (Methods). FIG. 13A-B presents longitudinal changes in the level of each biomarker for each patient. These measurements exhibited similar features as the sensor readings, demonstrating the immunosensor is able to report objective quantitative data within clinically-relevant ranges.

The multimodal measurement capabilities of the platform also enables relationships between these wound bed characteristics and bioburden parameters to be assessed. FIG. 5B shows the patient-specific correlation matrices using Pearson's correlation coefficients between the levels of measured parameters including wound sizes. Statistically significant positive correlations between IL-6 and IL-8 levels were observed in all patients. Wound fluids reporting the presence of higher load of *S. aureus* were associated with elevated levels of IL-6 and IL-8, consistent with keratinocyte responses to *S. aureus*. The degree or extent of the correlation of wound sizes with the remaining biomarkers was patient-specific, possibly owing to the samples being derived from patients of different gender, age, and wound duration. A prospective randomized study in a larger patient cohort will further confirm the prognostic value of these biomarkers for predicting wound healing status. Providing measures of inflammation and microbial bioburden that are inaccessible by current single or few non-inflammatory marker sensors, the immunosensing system is anticipated to serve as a beneficial addition to the existing clinical armamentarium.

Methods

Clinical Study on the Wound Exudates from Venous Ulcer Patients

Participants were patients who were diagnosed with venous ulcers and treated with four-layer compression bandaging. Patients aged above 21 with an ankle-brachial pressure index (ABPI)>=0.8 and open ulceration between the ankle and knee that failed to reduce in the size for more than 12 weeks were considered eligible to participate. Five patients (3 male and 2 female, age range 57-77) were recruited from the vascular outpatient clinics and provided their consent to participate. The wound exudates were collected once a week at their scheduled weekly change of dressing for five consecutive weeks using a standard protocol. Briefly, upon the removal of the four-layer bandages, the wound was cleansed with normal saline and covered by a transparent film dressing. The corresponding leg was kept dependent in the seated position for ~40 min. The accumulated wound exudates from all wounds of the affected leg were aspirated out from the transparent film dressing using a hypodermic needle and syringe. In view of vascular leakage in post conservative debridement that might compromise biomarker profiling, wound fluid sampling was conducted before conservative debridement. The ulcer size was measured using a ruler method. Topical dressings impregnated with antiseptic (e.g., cadexomer iodine, nanocrystalline silver) were used for wounds with colonization. They were placed onto the wounds after conservative debridement and before fresh four-layer bandages were applied. Foam dressings were placed underneath the bandages for wounds with excessive exudates where applicable. Rapid and simultaneous assessment of the wound bed characteristics and bioburden biomarkers in the wound exudates were conducted using the layered dressing disclosed herein. On the other hand, the wound exudates were also analyzed using conventional methods. Briefly, to conduct the cytokines assessment, a multiplex ELISA kit was custom-made by ThermoFisher and was performed according to the manufacturer's instruction on neat samples. The reading was done using Luminex 200 with xPONENT 3.1, and the concentration of cytokines was determined using MasterPlex QT 2.0.0.59. In addition, the pH values of the wound fluid samples were measured using a commercial pH meter (LAQUAtwin pH-33, HORIBA). *S. aureus* was detected via coagulase-positive Staphylococci enumeration. Briefly, 10 μL wound exudate was first diluted in 10 mL LB broth, followed by serial dilution. 1 mL of the original diluent and its serial diluent were respectively mixed with 15 mL sterilized RAPID'Staph agar medium, a mixture of base medium and egg yolk with potassium, for pour plate culture. After incubation, *S. aureus* formed black colonies on the opaque medium with a clear halo around the colonies attributed to egg yolk proteolysis. The number of *S. aureus* colonies on a RAPID'Staph agar plate showing between 30-300 was used to estimate the *S. aureus* cell density in the wound exudate sample. Optical images of the RAPID'Staph agar plates for wound fluid assessment of patients 1-5 are as shown in FIG. 15A-E, respectively.

Statistical Analyses

GraphPad Prism 8 and R (version 3.6.1) were used to perform statistical tests and data visualization. When comparing two groups, Wilcoxon signed-rank test was used. A p-value of <0.05 was considered as significant. The R packages ggplot2 (version 3.0.0) and GGally (version 1.4.0) were used to plot the correlation matrices.

Summary of Results in Examples 1-3

Disclosed herein is the development of an integrated flexible microfluidic multiplexed immunosensing system (layered dressing) that allows for simultaneous monitoring of multi-biomarker profiles using advanced sensor layout, functionalization techniques and wireless, flexible electronics. Here, a platform was designed to perform in situ interrogation of wound healing of venous ulcers in patients. The platform incorporated a layered dressing consisting of a permeable (perforated) wound contact layer, a microfluidic fluid collection layer, a biosensor sensing array (immunosensor), and a breathable barrier layer into a small integrated unit that was suitable for direct application onto the skin wound. A biomimetic passive fluid collection layer was developed to facilitate accurate and efficient determination of clinically relevant fluids in situ. A directional liquid transport system formed by a polar array of interconnected half-open, saw-tooth-shaped capillary channels with decreasing width facilitated efficient wound fluid accumulation for wound fluid analysis. The immunosensor array delivered simultaneous quantitative assessment of multiple clinically relevant biomarkers (TNF-α, IL-6, IL-8, TGF-β1, pH, temperature), and also bioburden (*S. aureus*) within minutes. The cytokine sensors characteristically exhibited selectivity, specificity, and reproducibility with minimal interference. The pH sensor was characterized to exhibit linearity, repeatability and reproducibility. Importantly, the immunosensor array was scalable and readily adjusted to fulfil a variety of potential applications. The immunosensor revealed the capability of in situ multi-biomarker assessment and biocompatibility in wound mice models. A portable wireless analyzer was also designed to interface with the immunosensor. Finally, an accompanying application containing a GUI to assist the management of patient's profiles and medical records while facilitating data collection, analysis and visualization were developed to integrate the immunosensing platform with existing patient records and enable rapid on-site clinical decisions to be made. As a proof of principle, the layered dressing was applied to assess wound exudates collected from patients with non-healing venous ulcers, once a week for five consecutive weeks. A graphical depiction of clinically relevant indicators of healing and bioburden served as a combined diagnostic/prognostic tool for better and more precise clinical management of the patient and their wounds. The layered dressing delivers rapid point-of-care delivery of the multiple quantitative clinical measurements. Without being bound by theory, it is believed that the platform represents first of its class of functioning of point-of-care devices, and able to deliver accurate and relevant personalized clinical diagnostic information to address the unmet need of the multitude of individuals suffering from non-healing chronic ulcers (e.g., venous ulcers, diabetic foot ulcers, pressure ulcers). Simplicity in design allows the layered dressing to be robust, adaptable and customizable. The layered dressing is readily reconfigured to detect other skin bacteria (e.g., *Enterococcus faecalis, Pseudomonas aeruginosa, Staphylococcus epidermidis, Corynebacterium* spp.) enabling pathogen-infected wounds to be stratified from wounds colonized by commensal organisms. Furthermore and without being bound by theory, the sensor technology is believed to allow alternative panel of biomarkers for a variety of applications requiring multiplexed analyses; for example, in diagnostic pathology and high content screening. The layered dressing discussed herein is readily reconfigurable to detect other skin bacteria (e.g., *Enterococcus faecalis, Pseudomonas aeruginosa, Staphylococcus epidermidis, Corynebacterium* spp.) enabling pathogen-infected wounds to be stratified from wounds colonized by commensal organisms.

The invention claimed is:

1. A layered dressing comprising:

a permeable wound contact layer for placing in contact with a wound;

a breathable barrier layer;

a fluid collection layer disposed between the wound contact layer and breathable barrier layer, the fluid collection layer comprising a biosensor housing portion and a fluid collection portion comprising a plurality of channels each having a terminus at the biosensor housing portion; and a biosensor sensing array comprising one or more electrodes, the biosensor sensing array being disposed between the biosensor housing portion of the fluid collection layer and the breathable barrier layer, wherein:

the channels within the fluid collection portion of the fluid collection layer are configured to allow the flow of fluid from a wound in only a single direction along the channels, where the channels each comprise a plurality of interconnected half-open saw-tooth-shaped capillary channels; and the channels comprise a first portion configured to draw fluid from a wound in contact with the wound contact layer, and a second portion proximal to the biosensor sensing array as compared to the first portion, where the width of the channels at the first portion is greater than the width of the channels at the second portion such that, when in use, the channels deliver wound fluid by capillary action from a wound in contact with the wound contact layer to the biosensor sensing array, and where the biosensor sensing array is configured to detect one or more markers in said wound fluid.

2. The layered dressing according to claim 1, wherein the wound contact layer comprises a plurality of perforations.

3. The layered dressing according to claim 1, wherein the fluid collection portion of the fluid collection layer has an annular shape having an outer surface, where annular shape defines a central portion, and where the biosensor housing portion of the fluid collection layer is located at the central portion.

4. The layered dressing according to claim 1, wherein the biosensor sensing array comprises one or more electrodes, each electrode being configured to detect a marker selected from the group consisting of a healing biomarker and a bioburden biomarker.

5. The layered dressing according to claim 4, wherein the healing biomarker is selected from the group consisting of TNF-α, IL-6, IL-8, TGF-$\beta_1$, and pH.

6. The layered dressing according to claim 1, wherein the biosensor sensing array comprises two or more electrodes, each electrode being configured to detect a marker selected from the group consisting of TNF-α, IL-6, IL-8, TGF-$\beta_1$, pH and a biomarker for *S. aureus*.

7. The layered dressing according to claim 6, wherein the biosensor sensing array comprises six electrodes, each electrode being configured to detect a marker selected from the group consisting of TNF-α, IL-6, IL-8, TGF-$\beta_1$, pH and a biomarker for *S. aureus*, such that the biosensor sensing array is able to simultaneously detect TNF-α, IL-6, IL-8, TGF-$\beta_1$, pH and a biomarker for *S. aureus*.

8. The layered dressing according to claim 1, wherein the biosensor sensing array comprises one or more aptamer-based working electrodes, each comprising an aptamer bonded to an electrode, where the aptamer is suitable for detecting a marker in the wound fluid.

9. The layered dressing according to claim 8, wherein the one or more aptamer-based working electrodes comprises an aptamer for IL-8, IL-6, TNF-α, TGF-$\beta_1$ and/or *S. aureus*.

10. The layered dressing according to claim 9, wherein any one of the following applies:

(a) the aptamer for IL-8 comprises the sequence 5'-/5ThioMC6-D/rGrGrGrGrGrCrUrUrArUrCrArUrUrCrCrArUrUrUrArGrUrGrUrUrArUrGrArUrArA rCrC/3MeBIN/-3';

(b) the aptamer for IL-6 comprises the sequence 5'-/5ThioMC6-D/GGTGGCAGGAGGACTATTTATTTGCTTTTCT/3MeBIN/-3';

(c) the aptamer for TNF-α comprises the sequence 5'-/5MeBIN/rG*rG*rA*rG*rU*rA*rU*rC*rU*rG*rA*rU*rG*rA*rC*rA*rA*rU*rU*rC*r G*rG*rA*rG*rC*rU*rC*rC/3ThioMC3-D/-3';

(d) the aptamer for TGF-1 comprises the sequence 5'-/5MeBIN/CG*CTCGG*CTTC*ACG*AG*ATT*CGTGT*CGTTGTGT*C*CTGT*A*C*C*CG*C*CTTG*A*C*C*AGT*C*ACT*CT*AG*AGC*AT*C*CGG*A*CTG/iSpC3/3ThioMC3-D/-3'; and for *S. aureus* comprises the sequence 5'-/5ThioMC6-(e) the aptamer D/TCGGCACGTTCTCAGTAGCGCTCGCTGGTCATCCCACAGCTACGTC/3MeBl N/-3'.

11. The layered dressing according to claim 10, wherein:

(a) the aptamer for IL-8 comprises the sequence 5'-/5ThioMC6-D/rGrGrGrGrGrCrUrUrArUrCrArUrUrCrCrArUrUrUrArGrUrGrUrUrArUrGrArUrArA rCrC/3MeBIN/-3'; or (b) the aptamer for IL-6 comprises the sequence 5'-/5ThioMC6-D/GGTGGCAGGAGGACTATTTATTTGCTTTTCT/3MeBIN/-3'.

12. The layered dressing according to claim 8, wherein the aptamer comprises a first end region and a second end region, and where the aptamer is bonded to the electrode via the first end region.

13. The layered dressing according to claim 12, wherein the surface of the one or more aptamer-based working electrodes comprises a layer of electrochemically exfoliated graphene-gold nanoparticles (AuNPs-GP) nanocomposite.

14. The layered dressing according to claim 8, wherein the aptamer is conjugated to a redox label, optionally wherein the redox label is methylene blue.

15. The layered dressing according to claim 1, wherein the biosensor sensing array comprises one or more of the following:

(a) a polyaniline pH sensor; and (b) a temperature sensor.

16. The layered dressing according to claim 1, wherein the biosensor sensing array is capable of wirelessly transmitting measurement data to a paired device.

* * * * *